US010273265B2

(12) United States Patent
Rothbauer et al.

(10) Patent No.: US 10,273,265 B2
(45) Date of Patent: Apr. 30, 2019

(54) EPITOPE TAG AND METHOD FOR DETECTION AND/OR PURIFICATION OF TAGGED POLYPEPTIDES

(71) Applicants: ChromoTek GmbH, Martinsried-Planegg (DE); NMI Naturwissenschaftliches und Medizinisches Institut an der Universität Tübingen, Reutlingen (DE)

(72) Inventors: Ulrich Rothbauer, Tübingen (DE); Oliver Poetz, Tübingen (DE); Tina Romer, Martinsried-Planegg (DE); Andrea Buchfellner, Martinsried-Planegg (DE); Larisa Yurlova, Martinsried-Planegg (DE); Kourosh Zolghadr, Martinsried-Planegg (DE); Jaqueline Bogner, Martinsried-Planegg (DE); Benjamin Ruf, Martinsried-Planegg (DE); Christian Linke-Winnebeck, Martinsried-Planegg (DE); Michael Metterlein, Martinsried-Planegg (DE)

(73) Assignees: NMI NATURWISSENSCHAFTLICHES UND MEDIZINISCHES INSTITUT AN DER UNIVERSITÄT TÜBINGEN, Reutlingen (DE); CHROMOTEK GMBH, Martinsried-Planegg (DE)

( * ) Notice: Subject to any disclaimer, the term of this patent is extended or adjusted under 35 U.S.C. 154(b) by 0 days.

(21) Appl. No.: 15/352,913

(22) Filed: Nov. 16, 2016

(65) Prior Publication Data
US 2017/0137467 A1 May 18, 2017

Related U.S. Application Data

(63) Continuation of application No. 14/996,903, filed on Jan. 15, 2016, now Pat. No. 10,125,166.

(30) Foreign Application Priority Data

Nov. 16, 2015 (EP) .................... 15194838

(51) Int. Cl.
A61K 39/00 (2006.01)
A61K 38/00 (2006.01)
A61K 38/16 (2006.01)
C07K 7/06 (2006.01)
C07K 1/22 (2006.01)
C07K 7/08 (2006.01)
C07K 14/47 (2006.01)
C07K 16/18 (2006.01)
G01N 21/64 (2006.01)
G01N 33/68 (2006.01)
C12N 15/62 (2006.01)
G01N 33/58 (2006.01)

(52) U.S. Cl.
CPC .................. *C07K 7/06* (2013.01); *C07K 1/22* (2013.01); *C07K 7/08* (2013.01); *C07K 14/47* (2013.01); *C07K 16/18* (2013.01); *C12N 15/62* (2013.01); *G01N 21/6428* (2013.01); *G01N 33/58* (2013.01); *G01N 33/68* (2013.01); *G01N 33/6803* (2013.01); *C07K 2317/34* (2013.01); *C07K 2317/565* (2013.01); *C07K 2317/567* (2013.01); *C07K 2317/569* (2013.01); *C07K 2317/92* (2013.01); *C07K 2319/40* (2013.01); *G01N 2021/6439* (2013.01)

(58) Field of Classification Search
CPC ......... A61K 38/04; A61K 38/10; A61K 38/16
USPC ............................................ 424/184.1, 185.1
See application file for complete search history.

(56) References Cited

U.S. PATENT DOCUMENTS

2009/0169503 A1* 7/2009 Felber .................. C07K 14/005
424/85.2
2017/0137464 A1 5/2017 Rothbauer et al.

FOREIGN PATENT DOCUMENTS

EP 3168306 5/2017
WO 2011147890 12/2011

OTHER PUBLICATIONS

Braun et al., "Peptides in headlock—a novel high-affinity and versatile peptide-binding nanobody for proteomics and microscopy," Scientific Reports, vol. 6, Jan. 21, 2016, 10 pages.
Jarvik et al., "Epitope Tagging," Annual Review of Genetics, vol. 32, Dec. 1998, pp. 601-618.
Terpe, "Overview of tag protein fusions: from molecular and biochemical fundamentals to commercial systems," Applied Microbiology and Biotechnology, Jan. 2003, pp. 523-533.
European Application No. 15194838.7, Extended European Search Report dated May 3, 2016, 8 pages.
Aberle et al., "Assembly of the cadherin-catenin complex in vitro with recombinant proteins," Journal of Cell Science, 107, (Pt 12), 3655-3663, 1994.

(Continued)

Primary Examiner — Rodney P Swartz
(74) Attorney, Agent, or Firm — Kilpatrick Townsend & Stockton LLP

(57) ABSTRACT

Provided herein is a novel epitope that can be used as a tag in methods for rapid and effective characterization, purification, and subcellular localization of polypeptides of interest, which comprise the tag. The tag is specifically recognized by an epitope specific antibody, which can be used to detect, capture, quantify, and/or purify polypeptides of interest that are tagged with the epitope. Also provided is novel epitope specific antibody.

3 Claims, 19 Drawing Sheets

Specification includes a Sequence Listing.

(56) References Cited

OTHER PUBLICATIONS

Adams et al., "PHENIX: a comprehensive Python-based system for macromolecular structure solution", Acta crystallographica. Section D, Biological crystallography, 2010, 66, 213-221.
Bauer et al., "Identification and quantification of a new family of peptide endocannabinoids (Pepcans) showing negative allosteric modulation at CB1 receptors," The Journal of Biological Chemistry, 2012, 287, 36944-36967.
Broisat et al., "Nanobodies targeting mouse/human VCAM1 for the nuclear imaging of atherosclerotic lesions", Circulation Research, 2012, 110, 927-937.
Chen et al., "MolProbity: all-atom structure validation for macromolecular crystallography", Acta crystallographica. Section D, Biological crystallography, 2010, 66, 12-21.
De Genst et al., "Molecular basis for the preferential cleft recognition by dromedary heavy-chain antibodies", Proceedings of the National Academy of Sciences of the United States of America, 2006, 103, 4586-4591.
De Genst et al., "Structure and properties of a complex of alpha-synuclein and a single-domain camelid antibody", Journal of Molecular Biology, 2010, 402, 326-343.
Emsley et al., "Model-building tools for molecular graphics", Acta crystallographica. Section D, Biological crystallography, 2004, 60, 2126-2132.
Ghahroudi et al., "Selection and identification of single domain antibody fragments from camel heavy-chain antibodies" FEBS Lett, 1997,414,521-526.
Govaert et al., "Dual beneficial effect of interloop disulfide bond for single domain antibody fragments", The Journal of Biological Chemistry, 2012, 287, 1970-1979.
Hilpert et al., "Anti-c-myc antibody 9E10: epitope key positions and variability characterized using peptide spot synthesis on cellulose", Protein Eng, 2001, 14, 803-806.
Huang et al., "SPECT imaging with 99mTc-labeled EGFR-specific nanobody for in vivo monitoring of EGFR expression", Molecular Imaging and Biology, MIB, 2008, 10, 167-175.
Kabsch et al., Acta crystallographica, Section D, Biological crystallography, 2010, 66, 125-132.
Kirchhofer et al., "Modulation of protein properties in living cells using nanobodies", Nature Structural & Molecular Biology, 2010, 17, 133-138, doi:10.1038/nsmb.1727.
Lee et al., "Ube3a, the E3 ubiquitin ligase causing Angelman syndrome and linked to autism, regulates protein homeostasis through the proteasomal shuttle Rpn10", Cellular and Molecular Life Sciences, 2014, CMLS, 71, 2747-2758.
Leonhardt et al., "Dynamics of DNA replication factories in living cells", The Journal of Cell Biology, 2000, 149, 271-280.
Luckert et al., "Snapshots of protein dynamics and post-translational modifications in one experiment-beta-catenin and its functions", Molecular & Cellular Proteomics: MCP 10, M110 007377, 2011.
Maier et al., "Real-time analysis of epithelial-mesenchymal transition using fluorescent single-domain antibodies", Scientific Reports, 2015, 5, 13402, doi:10.1038/srep13402.
McCoy et al., "Phaser crystallographic software," Journal of applied crystallography, 2007, 40, 658-674.
Murshudov et al., "Refinement of macromolecular structures by the maximum-likelihood method", Acta crystallographica. Section D, Biological crystallography, 1997, 53, 240-255.
Muyldermans, "Nanobodies: natural single-domain antibodies", Annual Review of Biochemistry, 2013, 82, 775-797.
Muyldermans, "Single domain camel antibodies: current status", Journal of Biotechnology, 2001, 74, 277-302.
Poetz et al., "Microsphere-based co-immunoprecipitation in multiplex." Analytical Biochemistry, 2009, 395, 244-248.
Ries et al., "A simple, versatile method for GFP-based super-resolution microscopy via nanobodies", Nature Methods, 2012, 9, 582-584.
Rothbauer et al., "A versatile nanotrap for biochemical and functional studies with fluorescent fusion proteins", Molecular & Cellular Proteomics, MCP 7, 2008, 282-289.
Rothbauer et al., "Targeting and tracing antigens in live cells with fluorescent nanobodies", Nature Methods, 2006, 3, 887-889.
Schembri et al., "The HA tag is cleaved and loses immunoreactivity during apoptosis", Nature Methods, 2007, 4, 107-108.
Stein et al., "CHAINSAW: a program for mutating pdb files used as templates in molecular replacement", Journal of Applied Crystallography, 2008, 41, 641-643.
Traenkle et al., "Monitoring interactions and dynamics of endogenous beta-catenin with intracellular nanobodies in living cells", Molecular & Cellular Proteomics, 2015, MCP, 707-723.
Vaneycken et al., "Preclinical screening of anti-HER2 nanobodies for molecular imaging of breast cancer," FASEB Journal, 2011, 25, 2433-2446.
Wegner et al., "Characterization and optimization of peptide arrays for the study of epitope-antibody interactions using surface plasmon resonance imaging", Analytical Chemistry, 2002, 74, 5161-5168.
Winn et al., "Overview of the CCP4 suite and current developments", Acta crystallographica. Section D, Biological crystallography, 2011, 67, 235-242.
Yoon et al., "Motile properties of vimentin intermediate filament networks in living cells", The Journal of Cell Biology,1998 143, 147-157.
U.S. Appl. No. 14/996,903, Non-Final Office Action dated Apr. 17, 2017, 8 pages.
U.S. Appl. No. 14/996,903, Restriction Requirement dated Nov. 3, 2016, 8 pages.

* cited by examiner

Figure 10
a
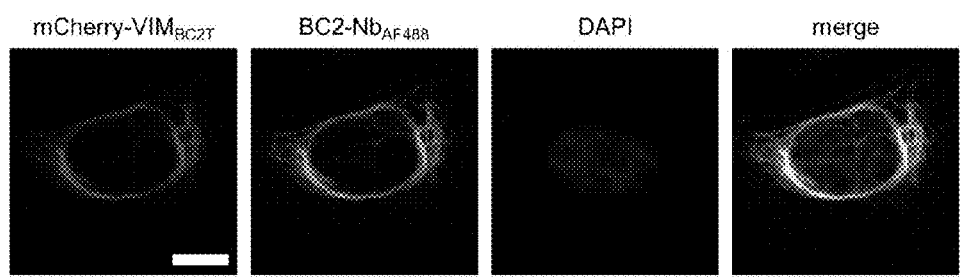
b
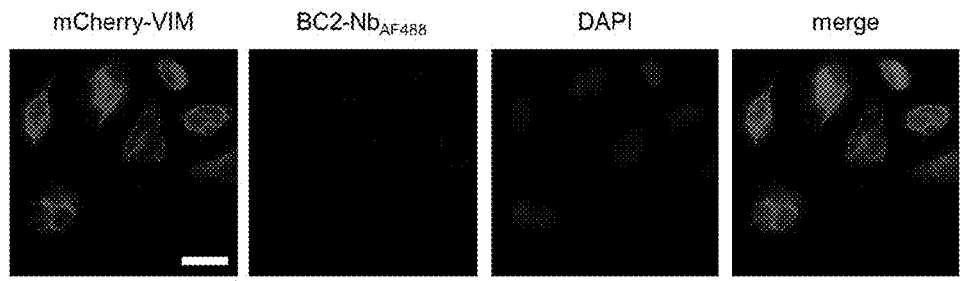
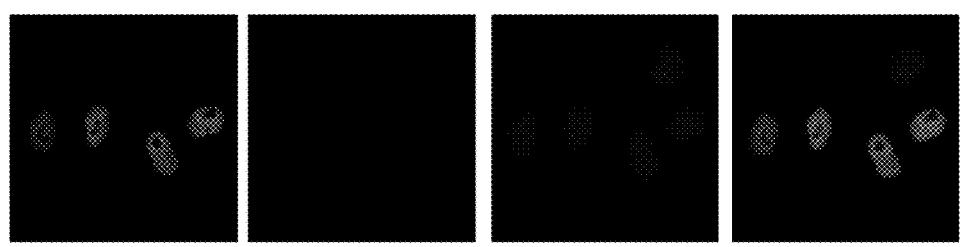

SEQUENCE LISTING

```
<160> NUMBER OF SEQ ID NOS: 66

<210> SEQ ID NO 1
<211> LENGTH: 8
<212> TYPE: PRT
<213> ORGANISM: Artificial sequence
<220> FEATURE:
<223> OTHER INFORMATION: Epitope peptide
<220> FEATURE:
<221> NAME/KEY: VARIANT
<222> LOCATION: (2)..(2)
<223> OTHER INFORMATION: K or a substitution
<220> FEATURE:
<221> NAME/KEY: VARIANT
<222> LOCATION: (3)..(3)
<223> OTHER INFORMATION: A or R, or a conservative substitution of A
      or R
<220> FEATURE:
<221> NAME/KEY: VARIANT
<222> LOCATION: (5)..(5)
<223> OTHER INFORMATION: V or a conservative substitution of V
<220> FEATURE:
<221> NAME/KEY: VARIANT
<222> LOCATION: (7)..(7)
<223> OTHER INFORMATION: H or a conservative substitution of H

<400> SEQUENCE: 1

Arg Xaa Xaa Ala Xaa Ser Xaa Trp
1               5

<210> SEQ ID NO 2
<211> LENGTH: 12
<212> TYPE: PRT
<213> ORGANISM: Artificial sequence
<220> FEATURE:
<223> OTHER INFORMATION: Epitope peptide
<220> FEATURE:
```

```
<221> NAME/KEY: VARIANT
<222> LOCATION: (2)..(2)
<223> OTHER INFORMATION: D or a conservative substitution of D
<220> FEATURE:
<221> NAME/KEY: VARIANT
<222> LOCATION: (4)..(4)
<223> OTHER INFORMATION: K or a substitution
<220> FEATURE:
<221> NAME/KEY: VARIANT
<222> LOCATION: (5)..(5)
<223> OTHER INFORMATION: A or R, a conservative substitution of A or R
<220> FEATURE:
<221> NAME/KEY: VARIANT
<222> LOCATION: (7)..(7)
<223> OTHER INFORMATION: V or a conservative substitution of V
<220> FEATURE:
<221> NAME/KEY: VARIANT
<222> LOCATION: (9)..(9)
<223> OTHER INFORMATION: H or a conservative substitution of H
<220> FEATURE:
<221> NAME/KEY: VARIANT
<222> LOCATION: (11)..(11)
<223> OTHER INFORMATION: Q or a conservative substitution of Q
<220> FEATURE:
<221> NAME/KEY: VARIANT
<222> LOCATION: (12)..(12)
<223> OTHER INFORMATION: Q or a conservative substitution of Q

<400> SEQUENCE: 2

Pro Xaa Arg Xaa Xaa Ala Xaa Ser Xaa Trp Xaa Xaa
1               5                   10

<210> SEQ ID NO 3
<211> LENGTH: 8
<212> TYPE: PRT
<213> ORGANISM: Artificial sequence
<220> FEATURE:
<223> OTHER INFORMATION: Epitope peptide 8 aa

<400> SEQUENCE: 3

Arg Lys Ala Ala Val Ser His Trp
1               5

<210> SEQ ID NO 4
<211> LENGTH: 12
<212> TYPE: PRT
<213> ORGANISM: Artificial sequence
<220> FEATURE:
<223> OTHER INFORMATION: Epitope peptide

<400> SEQUENCE: 4

Pro Asp Arg Lys Ala Ala Val Ser His Trp Gln Gln
1               5                   10

<210> SEQ ID NO 5
<211> LENGTH: 12
<212> TYPE: PRT
<213> ORGANISM: Artificial sequence
<220> FEATURE:
<223> OTHER INFORMATION: Epitope peptide

<400> SEQUENCE: 5

Pro Val Arg Ser Ala Ala Leu Ser Gln Trp Ser Ser
1               5                   10

<210> SEQ ID NO 6
<211> LENGTH: 122
<212> TYPE: PRT
<213> ORGANISM: Artificial sequence
<220> FEATURE:
<223> OTHER INFORMATION: BC2-Nb
```

<400> SEQUENCE: 6

Gln Val Gln Leu Val Glu Ser Gly Gly Gly Leu Val Gln Pro Gly Gly
1               5                   10                  15

Ser Leu Thr Leu Ser Cys Thr Ala Ser Gly Phe Thr Leu Asp His Tyr
            20                  25                  30

Asp Ile Gly Trp Phe Arg Gln Ala Pro Gly Lys Glu Arg Glu Gly Val
        35                  40                  45

Ser Cys Ile Asn Asn Ser Asp Asp Thr Tyr Tyr Ala Asp Ser Val
    50                  55                  60

Lys Gly Arg Phe Thr Ile Phe Met Asp Asn Ala Lys Asp Thr Val Tyr
65                  70                  75                  80

Leu Gln Met Asn Ser Leu Lys Pro Glu Asp Thr Ala Ile Tyr Tyr Cys
                85                  90                  95

Ala Glu Ala Arg Gly Cys Lys Arg Gly Arg Tyr Glu Tyr Asp Phe Trp
            100                 105                 110

Gly Gln Gly Thr Gln Val Thr Val Ser Ser
            115                 120

<210> SEQ ID NO 7
<211> LENGTH: 25
<212> TYPE: PRT
<213> ORGANISM: Artificial sequence
<220> FEATURE:
<223> OTHER INFORMATION: Framework region 1 of BC2-Nb

<400> SEQUENCE: 7

Gln Val Gln Leu Val Glu Ser Gly Gly Gly Leu Val Gln Pro Gly Gly
1               5                   10                  15

Ser Leu Thr Leu Ser Cys Thr Ala Ser
            20                  25

<210> SEQ ID NO 8
<211> LENGTH: 8
<212> TYPE: PRT
<213> ORGANISM: Artificial sequence
<220> FEATURE:
<223> OTHER INFORMATION: CDR1 of BC2-Nb

<400> SEQUENCE: 8

Gly Phe Thr Leu Asp His Tyr Asp
1               5

<210> SEQ ID NO 9
<211> LENGTH: 17
<212> TYPE: PRT
<213> ORGANISM: Artificial sequence
<220> FEATURE:
<223> OTHER INFORMATION: Framework region 2 of BC2-N

<400> SEQUENCE: 9

Ile Gly Trp Phe Arg Gln Ala Pro Gly Lys Glu Arg Glu Gly Val Ser
1               5                   10                  15

Cys

<210> SEQ ID NO 10
<211> LENGTH: 9
<212> TYPE: PRT
<213> ORGANISM: Artificial sequence
<220> FEATURE:
<223> OTHER INFORMATION: CDR2 of BC2-Nb

```
<400> SEQUENCE: 10

Ile Asn Asn Ser Asp Asp Asp Thr Tyr
1               5

<210> SEQ ID NO 11
<211> LENGTH: 39
<212> TYPE: PRT
<213> ORGANISM: Artificial sequence
<220> FEATURE:
<223> OTHER INFORMATION: framework region 3 of BC2-Nb

<400> SEQUENCE: 11

Tyr Ala Asp Ser Val Lys Gly Arg Phe Thr Ile Phe Met Asp Asn Ala
1               5                   10                  15

Lys Asp Thr Val Tyr Leu Gln Met Asn Ser Leu Lys Pro Glu Asp Thr
            20                  25                  30

Ala Ile Tyr Tyr Cys Ala Glu
        35

<210> SEQ ID NO 12
<211> LENGTH: 14
<212> TYPE: PRT
<213> ORGANISM: Artificial Sequence
<220> FEATURE:
<223> OTHER INFORMATION: CDR3 of BC2-Nb

<400> SEQUENCE: 12

Ala Arg Gly Cys Lys Arg Gly Arg Tyr Glu Tyr Asp Phe Trp
1               5                   10

<210> SEQ ID NO 13
<211> LENGTH: 10
<212> TYPE: PRT
<213> ORGANISM: Artificial sequence
<220> FEATURE:
<223> OTHER INFORMATION: Framework region 4 of BC2-Nb

<400> SEQUENCE: 13

Gly Gln Gly Thr Gln Val Thr Val Ser Ser
1               5                   10

<210> SEQ ID NO 14
<211> LENGTH: 10
<212> TYPE: PRT
<213> ORGANISM: Artificial sequence
<220> FEATURE:
<223> OTHER INFORMATION: Epitope peptide 10 aa

<400> SEQUENCE: 14

Pro Asp Arg Lys Ala Ala Val Ser His Trp
1               5                   10

<210> SEQ ID NO 15
<211> LENGTH: 28
<212> TYPE: DNA
<213> ORGANISM: Artificial sequence
<220> FEATURE:
<223> OTHER INFORMATION: GFP(BC2T) forward primer

<400> SEQUENCE: 15
gcaccatgga tggtgagcaa gggcgagg                                      28

<210> SEQ ID NO 16
<211> LENGTH: 31
<212> TYPE: DNA
```

```
<213> ORGANISM: Artificial Sequence
<220> FEATURE:
<223> OTHER INFORMATION: GFP(BC2T) reverse primer

<400> SEQUENCE: 16
gacgtcgact tactgctgcc agtgactaac a                              31

<210> SEQ ID NO 17
<211> LENGTH: 23
<212> TYPE: DNA
<213> ORGANISM: Artificial Sequence
<220> FEATURE:
<223> OTHER INFORMATION: His6-GFP(BC2T) forward primer

<400> SEQUENCE: 17
cagggatccg agtgagcaag ggc                                       23

<210> SEQ ID NO 18
<211> LENGTH: 29
<212> TYPE: DNA
<213> ORGANISM: Artificial Sequence
<220> FEATURE:
<223> OTHER INFORMATION: His6-GFP(BC2T) reverse primer

<400> SEQUENCE: 18
cagggtacct tactgctgcc agtgactaa                                 29

<210> SEQ ID NO 19
<211> LENGTH: 25
<212> TYPE: DNA
<213> ORGANISM: Artificial sequence
<220> FEATURE:
<223> OTHER INFORMATION: GFP BC2Tmut forward primer

<400> SEQUENCE: 19
ggatccgatg gtgagcaagg gcgag                                     25

<210> SEQ ID NO 20
<211> LENGTH: 65
<212> TYPE: DNA
<213> ORGANISM: Artificial sequence
<220> FEATURE:
<223> OTHER INFORMATION: GFP(BC2Tmut) reverse primer

<400> SEQUENCE: 20
ggtaccttag ctgctccact ggctcagcgc cgcgctccgg accggcttgt acagctcgtc   60
catgc                                                              65

<210> SEQ ID NO 21
<211> LENGTH: 30
<212> TYPE: DNA
<213> ORGANISM: Artificial sequence
<220> FEATURE:
<223> OTHER INFORMATION: His6-GFP(BC2T-10) forward primer

<400> SEQUENCE: 21
ccccggatcc gatggtgagc aagggcgagg                                30

<210> SEQ ID NO 22
<211> LENGTH: 64
<212> TYPE: DNA
<213> ORGANISM: Artificial sequence
<220> FEATURE:
<223> OTHER INFORMATION: His6-GFP(BC2T-10) reverse primer

<400> SEQUENCE: 22
```

```
cccggtacc ttaccaatgt gacaccgctg ctttgcggtc aggcttgtac agctcgtcca      60
tgcc                                                                   64

<210> SEQ ID NO 23
<211> LENGTH: 30
<212> TYPE: DNA
<213> ORGANISM: Artificial Sequence
<220> FEATURE:
<223> OTHER INFORMATION: His6-GFP(BC2T-8) forward primer

<400> SEQUENCE: 23
ccccggatcc gatggtgagc aagggcgagg                                       30

<210> SEQ ID NO 24
<211> LENGTH: 56
<212> TYPE: DNA
<213> ORGANISM: Artificial sequence
<220> FEATURE:
<223> OTHER INFORMATION: His6-GFP(BC2T-8) reverse primer

<400> SEQUENCE: 24
ccccggtacc ttaccagtgg gaaacggctg ctttacgctt gtacagctcg tccatg          56

<210> SEQ ID NO 25
<211> LENGTH: 27
<212> TYPE: DNA
<213> ORGANISM: Artificial sequence
<220> FEATURE:
<223> OTHER INFORMATION: eGFP(BC2T) forward primer

<400> SEQUENCE: 25
aagctagcgc taccggtcgc caccatg                                          27

<210> SEQ ID NO 26
<211> LENGTH: 62
<212> TYPE: DNA
<213> ORGANISM: Artificial Sequence
<220> FEATURE:
<223> OTHER INFORMATION: eGFP(BC2T) reverse primer

<400> SEQUENCE: 26
aaggtacctt attgctgcca gtgactaaca gccgcttttc tgtctggctt gtacagctcg      60
tc                                                                     62

<210> SEQ ID NO 27
<211> LENGTH: 51
<212> TYPE: DNA
<213> ORGANISM: Artificial sequence
<220> FEATURE:
<223> OTHER INFORMATION: NheI - BC2T - BglII

<400> SEQUENCE: 27
gctagcatgc ccgatcgtaa ggctgcggtc tctcattggc aacagagatc t               51

<210> SEQ ID NO 28
<211> LENGTH: 41
<212> TYPE: DNA
<213> ORGANISM: Artificial Sequence
<220> FEATURE:
<223> OTHER INFORMATION: mCherry-Vimentin(BC2T) forward primer

<400> SEQUENCE: 28
aaaagcttag gtggaggagg ttcttccacc aggtccgtgt c                          41
```

```
<210> SEQ ID NO 29
<211> LENGTH: 62
<212> TYPE: DNA
<213> ORGANISM: Artificial sequence
<220> FEATURE:
<223> OTHER INFORMATION: mCherry-Vimentin(BC2T) reverse primer

<400> SEQUENCE: 29
aaggtaccct attgctgcca gtgactaaca gccgcttttc tgtctggttc aaggtcatcg    60
tg                                                                  62

<210> SEQ ID NO 30
<211> LENGTH: 23
<212> TYPE: DNA
<213> ORGANISM: Artificial sequence
<220> FEATURE:
<223> OTHER INFORMATION: GFP-PCNA(BC2T) forward primer

<400> SEQUENCE: 30
gtatggcttc gtggggatcc ccg                                           23

<210> SEQ ID NO 31
<211> LENGTH: 78
<212> TYPE: DNA
<213> ORGANISM: Artificial Sequence
<220> FEATURE:
<223> OTHER INFORMATION: GFP-PCNA(BC2T) reverse primer

<400> SEQUENCE: 31
ggggtctaga ctaaaggtac cctattgctg ccagtgacta acagccgctt ttctgtctgg    60
agatccttct tcatcctc                                                 78

<210> SEQ ID NO 32
<211> LENGTH: 12
<212> TYPE: PRT
<213> ORGANISM: Artificial Sequence
<220> FEATURE:
<223> OTHER INFORMATION: Epitope peptide
<220> FEATURE:
<221> NAME/KEY: VARIANT
<222> LOCATION: (1)..(1)
<223> OTHER INFORMATION: P or A
<220> FEATURE:
<221> NAME/KEY: VARIANT
<222> LOCATION: (2)..(2)
<223> OTHER INFORMATION: D or a conservative substitution of D
<220> FEATURE:
<221> NAME/KEY: VARIANT
<222> LOCATION: (4)..(4)
<223> OTHER INFORMATION: K or a substitution
<220> FEATURE:
<221> NAME/KEY: VARIANT
<222> LOCATION: (5)..(5)
<223> OTHER INFORMATION: A or R, or a conservative substitution of A
     or R
<220> FEATURE:
<221> NAME/KEY: VARIANT
<222> LOCATION: (7)..(7)
<223> OTHER INFORMATION: V or a conservative substitution of V
<220> FEATURE:
<221> NAME/KEY: VARIANT
<222> LOCATION: (9)..(9)
<223> OTHER INFORMATION: H or a conservative substitution of H
<220> FEATURE:
<221> NAME/KEY: VARIANT
<222> LOCATION: (11)..(11)
<223> OTHER INFORMATION: Q or a conservative substitution of Q
<220> FEATURE:
<221> NAME/KEY: VARIANT
<222> LOCATION: (12)..(12)
```

<223> OTHER INFORMATION: Q or a conservative substitution of Q

<400> SEQUENCE: 32

Xaa Xaa Arg Xaa Xaa Ala Xaa Ser Xaa Trp Xaa Xaa
1               5                   10

<210> SEQ ID NO 33
<211> LENGTH: 12
<212> TYPE: PRT
<213> ORGANISM: Artificial sequence
<220> FEATURE:
<223> OTHER INFORMATION: Epitope peptide

<400> SEQUENCE: 33

Pro Asp Arg Val Arg Ala Val Ser His Trp Ser Ser
1               5                   10

<210> SEQ ID NO 34
<211> LENGTH: 12
<212> TYPE: PRT
<213> ORGANISM: Artificial sequence
<220> FEATURE:
<223> OTHER INFORMATION: Epitope peptide

<400> SEQUENCE: 34

Ala Asp Arg Val Arg Ala Val Ser His Trp Ser Ser
1               5                   10

<210> SEQ ID NO 35
<211> LENGTH: 50
<212> TYPE: DNA
<213> ORGANISM: Artificial Sequence
<220> FEATURE:
<223> OTHER INFORMATION: mCherry_BC2T_fw

<400> SEQUENCE: 35
gtacagtggt ccggatcgca aagcggcggt gagccattgg cagcagtaaa            50

<210> SEQ ID NO 36
<211> LENGTH: 50
<212> TYPE: DNA
<213> ORGANISM: Artificial Sequence
<220> FEATURE:
<223> OTHER INFORMATION: mCherry_BC2T_rv

<400> SEQUENCE: 36
agcttttact gctgccaatg gctcaccgcc gctttgcgat ccggaccact            50

<210> SEQ ID NO 37
<211> LENGTH: 50
<212> TYPE: DNA
<213> ORGANISM: Artificial Sequence
<220> FEATURE:
<223> OTHER INFORMATION: mCherry_SEQ33_fw

<400> SEQUENCE: 37
gtacagtggt ccggatcgcg tgcgcgcggt gagccattgg agcagctaaa            50

<210> SEQ ID NO 38
<211> LENGTH: 50
<212> TYPE: DNA
<213> ORGANISM: Artificial Sequence
<220> FEATURE:
<223> OTHER INFORMATION: mCherry_SEQ33_rv

<400> SEQUENCE: 38
agcttttagc tgctccaatg gctcaccgcg cgcacgcgat ccggaccact       50

<210> SEQ ID NO 39
<211> LENGTH: 50
<212> TYPE: DNA
<213> ORGANISM: Artificial Sequence
<220> FEATURE:
<223> OTHER INFORMATION: mCherry_SEQ34_fw

<400> SEQUENCE: 39
gtacagtggt gcggatcgcg tgcgcgcggt gagccattgg agcagctaaa       50

<210> SEQ ID NO 40
<211> LENGTH: 50
<212> TYPE: DNA
<213> ORGANISM: Artificial Sequence
<220> FEATURE:
<223> OTHER INFORMATION: mCherry_SEQ34_rv

<400> SEQUENCE: 40
agcttttagc tgctccaatg gctcaccgcg cgcacgcgat ccgcaccact       50

<210> SEQ ID NO 41
<211> LENGTH: 46
<212> TYPE: DNA
<213> ORGANISM: Artificial Sequence
<220> FEATURE:
<223> OTHER INFORMATION: mCherry_BC2T_fw2

<400> SEQUENCE: 41
tatgccggat cgcaaagcgg cggtgagcca ttggcagcag ggctcg          46

<210> SEQ ID NO 42
<211> LENGTH: 48
<212> TYPE: DNA
<213> ORGANISM: Artificial Sequence
<220> FEATURE:
<223> OTHER INFORMATION: mCherry_BC2T_rv2

<400> SEQUENCE: 42
gatccgagcc ctgctgccaa tggctcaccg ccgctttgcg atccggca        48

<210> SEQ ID NO 43
<211> LENGTH: 46
<212> TYPE: DNA
<213> ORGANISM: Artificial Sequence
<220> FEATURE:
<223> OTHER INFORMATION: mCherry_SEQ33_fw2

<400> SEQUENCE: 43
tatgccggat cgcgtgcgcg cggtgagcca ttggagcagc ggctcg          46

<210> SEQ ID NO 44
<211> LENGTH: 48
<212> TYPE: DNA
<213> ORGANISM: Artificial Sequence
<220> FEATURE:
<223> OTHER INFORMATION: mCherry_SEQ33_rv2

<400> SEQUENCE: 44
gatccgagcc gctgctccaa tggctcaccg cgcgcacgcg atccggca        48

<210> SEQ ID NO 45
<211> LENGTH: 46
<212> TYPE: DNA
<213> ORGANISM: Artificial Sequence

```
<220> FEATURE:
<223> OTHER INFORMATION: mCherry_SEQ34_fw2

<400> SEQUENCE: 45
tatggcggat cgcgtgcgcg cggtgagcca ttggagcagc ggctcg            46

<210> SEQ ID NO 46
<211> LENGTH: 48
<212> TYPE: DNA
<213> ORGANISM: Artificial Sequence
<220> FEATURE:
<223> OTHER INFORMATION: mCherry_SEQ34_rv2

<400> SEQUENCE: 46
gatccgagcc gctgctccaa tggctcaccg cgcgcacgcg atccgcca          48

<210> SEQ ID NO 47
<211> LENGTH: 23
<212> TYPE: DNA
<213> ORGANISM: Artificial sequence
<220> FEATURE:
<223> OTHER INFORMATION: CALL001 primer

<400> SEQUENCE: 47
gtcctggctg ctcttctaca agg                                     23

<210> SEQ ID NO 48
<211> LENGTH: 23
<212> TYPE: DNA
<213> ORGANISM: Artificial sequence
<220> FEATURE:
<223> OTHER INFORMATION: CALL002 primer

<400> SEQUENCE: 48
ggtacgtgct gttgaactgt tcc                                     23

<210> SEQ ID NO 49
<211> LENGTH: 39
<212> TYPE: DNA
<213> ORGANISM: Artificial sequence
<220> FEATURE:
<223> OTHER INFORMATION: SM017 primer

<400> SEQUENCE: 49
ccagccggcc atggctcagg tgcagctggt ggagtctgg                    39

<210> SEQ ID NO 50
<211> LENGTH: 39
<212> TYPE: DNA
<213> ORGANISM: Artificial sequence
<220> FEATURE:
<223> OTHER INFORMATION: SM018 primer

<400> SEQUENCE: 50
ccagccggcc atggctgatg tgcagctggt ggagtctgg                    39

<210> SEQ ID NO 51
<211> LENGTH: 33
<212> TYPE: DNA
<213> ORGANISM: Artificial sequence
<220> FEATURE:
<223> OTHER INFORMATION: reverse primer CALL002

<400> SEQUENCE: 51
catgccatga ctcgcggcca cgccggccat ggc                          33
```

<210> SEQ ID NO 52
<211> LENGTH: 35
<212> TYPE: DNA
<213> ORGANISM: Artificial sequence
<220> FEATURE:
<223> OTHER INFORMATION: reverse primer 38

<400> SEQUENCE: 52
ggactagtgc ggccgctgga gacggtgacc tgggt    35

<210> SEQ ID NO 53
<211> LENGTH: 10
<212> TYPE: PRT
<213> ORGANISM: Artificial sequence
<220> FEATURE:
<223> OTHER INFORMATION: Synthetic construct

<400> SEQUENCE: 53

Glu Gln Lys Leu Ile Ser Glu Glu Asp Leu
1               5                   10

<210> SEQ ID NO 54
<211> LENGTH: 16
<212> TYPE: PRT
<213> ORGANISM: Artificial sequence
<220> FEATURE:
<223> OTHER INFORMATION: Synthetic construct

<400> SEQUENCE: 54

Ala Met Glu Pro Asp Arg Lys Ala Ala Val Ser His Trp Gln Gln Gln
1               5                   10                  15

<210> SEQ ID NO 55
<211> LENGTH: 15
<212> TYPE: PRT
<213> ORGANISM: Artificial sequence
<220> FEATURE:
<223> OTHER INFORMATION: Synthetic construct

<400> SEQUENCE: 55

Asp Arg Lys Ala Ala Val Ser His Trp Gln Gln Gln Ser Tyr Leu
1               5                   10                  15

<210> SEQ ID NO 56
<211> LENGTH: 14
<212> TYPE: PRT
<213> ORGANISM: Artificial sequence
<220> FEATURE:
<223> OTHER INFORMATION: Synthetic construct

<400> SEQUENCE: 56

Met Glu Pro Asp Arg Lys Ala Ala Val Ser His Trp Gln Gln
1               5                   10

<210> SEQ ID NO 57
<211> LENGTH: 13
<212> TYPE: PRT
<213> ORGANISM: Artificial sequence
<220> FEATURE:
<223> OTHER INFORMATION: Synthetic construct

<400> SEQUENCE: 57

Met Glu Pro Asp Arg Lys Ala Ala Val Ser His Trp Gln
1               5                   10

<210> SEQ ID NO 58

```
<211> LENGTH: 12
<212> TYPE: PRT
<213> ORGANISM: Artificial sequence
<220> FEATURE:
<223> OTHER INFORMATION: Synthetic construct

<400> SEQUENCE: 58

Met Glu Pro Asp Arg Lys Ala Ala Val Ser His Trp
1               5                   10

<210> SEQ ID NO 59
<211> LENGTH: 11
<212> TYPE: PRT
<213> ORGANISM: Artificial sequence
<220> FEATURE:
<223> OTHER INFORMATION: Synthetic construct

<400> SEQUENCE: 59

Met Glu Pro Asp Arg Lys Ala Ala Val Ser His
1               5                   10

<210> SEQ ID NO 60
<211> LENGTH: 10
<212> TYPE: PRT
<213> ORGANISM: Artificial sequence
<220> FEATURE:
<223> OTHER INFORMATION: Synthetic construct

<400> SEQUENCE: 60

Met Glu Pro Asp Arg Lys Ala Ala Val Ser
1               5                   10

<210> SEQ ID NO 61
<211> LENGTH: 13
<212> TYPE: PRT
<213> ORGANISM: Artificial sequence
<220> FEATURE:
<223> OTHER INFORMATION: Synthetic construct

<400> SEQUENCE: 61

Glu Pro Asp Arg Lys Ala Ala Val Ser His Trp Gln Gln
1               5                   10

<210> SEQ ID NO 62
<211> LENGTH: 11
<212> TYPE: PRT
<213> ORGANISM: Artificial sequence
<220> FEATURE:
<223> OTHER INFORMATION: Synthetic construct

<400> SEQUENCE: 62

Asp Arg Lys Ala Ala Val Ser His Trp Gln Gln
1               5                   10

<210> SEQ ID NO 63
<211> LENGTH: 10
<212> TYPE: PRT
<213> ORGANISM: Artificial sequence
<220> FEATURE:
<223> OTHER INFORMATION: Synthetic construct

<400> SEQUENCE: 63

Arg Lys Ala Ala Val Ser His Trp Gln Gln
1               5                   10

<210> SEQ ID NO 64
<211> LENGTH: 9
```

```
<212> TYPE: PRT
<213> ORGANISM: Artificial sequence
<220> FEATURE:
<223> OTHER INFORMATION: Synthetic construct

<400> SEQUENCE: 64

Lys Ala Ala Val Ser His Trp Gln Gln
1               5

<210> SEQ ID NO 65
<211> LENGTH: 8
<212> TYPE: PRT
<213> ORGANISM: Artificial sequence
<220> FEATURE:
<223> OTHER INFORMATION: Synthetic construct

<400> SEQUENCE: 65

Ala Ala Val Ser His Trp Gln Gln
1               5

<210> SEQ ID NO 66
<211> LENGTH: 16
<212> TYPE: PRT
<213> ORGANISM: Artificial sequence
<220> FEATURE:
<223> OTHER INFORMATION: Synthetic construct

<400> SEQUENCE: 66

Glu Pro Asp Arg Lys Ala Ala Ser Val Ser His Trp Gln Gln Gln Ser
1               5                   10                  15
```

EPITOPE TAG AND METHOD FOR DETECTION AND/OR PURIFICATION OF TAGGED POLYPEPTIDES

This application claims priority to European Patent Application No. 15194838.7, filed on Nov. 16, 2015, and is a continuation-in-part application of U.S. patent application Ser. No. 14/996,903, filed on Jan. 15, 2016, both of which are incorporated herein by reference in their entireties.

FIELD OF THE INVENTION

Provided herein are compositions and methods related to the field of biomedical research, biochemistry and cell biology. A novel epitope is provided that can be used as a tag for use in rapid and effective characterization, purification, and in vivo localization of polypeptides of interest that comprise the tag. The tag is specifically recognized by a novel epitope specific antibody, which allows antibody-tag interaction.

BACKGROUND

In the post-genomic era the field of proteomics has grown dramatically. For a multitude of applications, ranging from mass spectrometry analysis to high-content imaging, affinity-based assays are indispensable. Affinity-based assays rely on the detection of protein-protein-interaction (PPI) between a receptor and a ligand, such as an antibody and an antigen. In the case of the monitoring of an antigen-antibody-interaction the assay is also called an immunoaffinity assay. Immunoaffinity assays are the method of choice for testing the identity, quantity, and/or location of a polypeptide of interest. However, there are cases in which no suitable antibody is available. This disadvantage of immunoaffinity-based assays can be overcome by a method called "epitope tagging", wherein a protein is tagged with an epitope, i.e. the binding part of an antigenic protein.

Epitope tagging is a technique in which a known epitope is fused to a recombinant protein by means of genetic engineering. By choosing an epitope for which an antibody is available, the technique allows the detection of proteins for which no antibody is available. Since the late 1980s epitope tagging has become a standard molecular genetics method for enabling rapid and effective characterization, purification, and in vivo localization of the protein products of cloned genes.

In the early days of proteomics the first commercially available tags were originally designed for protein purification. Examples of these early tags are FLAG, 6×HIS and the glutathione-S-transferase (GST) system. The 6×HIS tag relies on metal affinity and the GST system relies on affinity of GST to glutathione. FLAG is one of the first epitope tags used commercially.

Later on, the discovery of fluorescent protein reporters such as green fluorescent protein (GFP) made it possible to detect proteins intracellularly without the need of a secondary reagent. In this case, proteins of interest were tagged with the full-length protein sequence of GFP, rendering the tagged protein of interest fluorescent.

However, the problem with tags comprising full-length proteins such as GST maltose-binding protein (MBP) or GFP, is that they sometimes sterically interfere with subcellular protein localization or folding, which may compromise or abrogate the native function of the protein to be analyzed. Therefore numerous small peptide-based epitope-tags such as c-myc, V5, HA, CBP or FLAG have been developed.

Such tags have either a synthetic origin (FLAG) or are derived from viral (HA, V5) or endogenous mammalian (c-myc, CBP) proteins. They are characterized by a size of 8-26 amino acid residues and are detected by classical IgGs (poly- or monoclonal). One problem with tags derived from endogenous proteins is the fact that the tag-specific antibody generally also binds to the endogenous protein. If the interaction between the tag and the antibody is not specific, the assay may give false positives. Due to the competition between tagged protein and endogenous protein as binding partners for the antibody, the assay will be less efficient.

Although many immunoaffinity capture systems are available using tag-specific antibodies, there are still severe problems due to low affinity binding, unspecific interactions, batch to batch variations or reduced functionality of the antibodies upon covalent coupling to solid surfaces. Furthermore, a specific problem of known immunoaffinity detection and/or capture systems is their dependence on conventional antibodies evolved by the vertebrate immune system to detect the epitope-tagged protein.

SUMMARY

Provided herein is an immunoaffinity detection and/or capture system, which is characterized by high affinity, specificity and reproducibility.

Also provided is an epitope specific antibody, which can specifically, reliably, and reproducibly interact with an epitope tag. Nucleic acids encoding the antibody or fragments thereof are also provided. For example, provided herein is a nucleic acid encoding SEQ ID NO: 7, SEQ ID NO: 8, SEQ ID NO: 9, SEQ ID NO: 10, SEQ ID NO: 11, SEQ ID NO: 12 and/or SEQ ID NO: 13. Further provided is an epitope tag which can interact specifically, reliably, reproducibly, and with high affinity with the epitope specific antibody. For example, the epitope tag can be an isolated epitope peptide consisting of or comprising from about 8 to about 25 amino acids, wherein the amino acid sequence consists of or comprises a sequence as defined in SEQ ID NO: 1 ($RX_4X_5AX_7SX_9W$), wherein $X_4$ can be K or a substitution; wherein $X_5$ can be A or R or a conservative substitution of A or R; wherein $X_7$ can be V or a conservative substitution of V, and/or wherein $X_9$ can be H or a conservative substitution of H. Nucleic acids encoding the isolated epitope peptides are also provided.

Also provided is an isolated epitope peptide consisting of or comprising from 12 to 25 amino acids, wherein the amino acid sequence consists of or comprises a sequence as defined by SEQ ID NO:32 ($X_1X_2RX_4X_5AX_7SX_9WX_{11}X_{12}$), wherein $X_1$ can be P or A, wherein $X_2$ can be D or a conservative substitution of D, wherein $X_4$ can be K or a substitution; wherein $X_5$ can be A or R or a conservative substitution of A or R; wherein $X_7$ can be V or a conservative substitution of V, wherein $X_9$ can be H or a conservative substitution of H, wherein $X_{11}$ can be Q or a conservative substitution of Q and/or wherein $X_{12}$ can be Q or a conservative substitution of Q.

Also provided are the components for an immunoaffinity-based assay, which is suitable to detect a polypeptide of interest reliably, specifically and efficiently. This assay can be used for cellular imaging and/or direct antigen detection.

Also provided is an immunoaffinity-based assay, which is suitable to reliably, specifically and efficiently purify a polypeptide of interest.

Furthermore, provided herein is a system for capture and/or detection, in particular a system that can be used for different types of analysis, for combined analysis by microscopic and biochemical studies, among others.

Further provided is a robust purification method for recombinant proteins that allows the use of non-denaturing or denaturing conditions.

(a) shows the BC2-Nb/BC2T backbone interactions. The BC2-peptide (BC2T) folds into a β-strand that is part of a β-sheet structure formed by the complementarity determining region 3 (CDR3) and framework regions 2 and 3. Shown are 13 backbone-backbone hydrogen bonds (black dashed lines) of which one is mediated by water. The CDR3 contributes eight and the framework regions five of these interactions. The CDR1 and CDR2 are not participating in binding.

(b) shows the so called "Headlock" interaction. A charge-mediated interaction between Arg106 of the CDR3 and Glu44 in FR2 is stabilizing the BC2-Nb/BC2T complex. These amino acid side chains are reaching over the peptide, forming a salt bridge that locks the peptide into its binding site.

(c) shows specific BC2-Nb/BC2T interactions. In addition to the backbone interactions, a small number of interactions mediated by side chains generate specificity for the BC2T peptide sequence. BC2T residue W10 is involved in a CH-π interaction with Cys50 (dotted line). A water molecule is bound by peptide amino acids S8, Tyr109, two carbonyl groups and one amine group. The charge-mediated interaction between Arg106 (CDR3) and the side chain of Glu44 (FR2), reaching over the peptide, is also shown.

Figure 2:
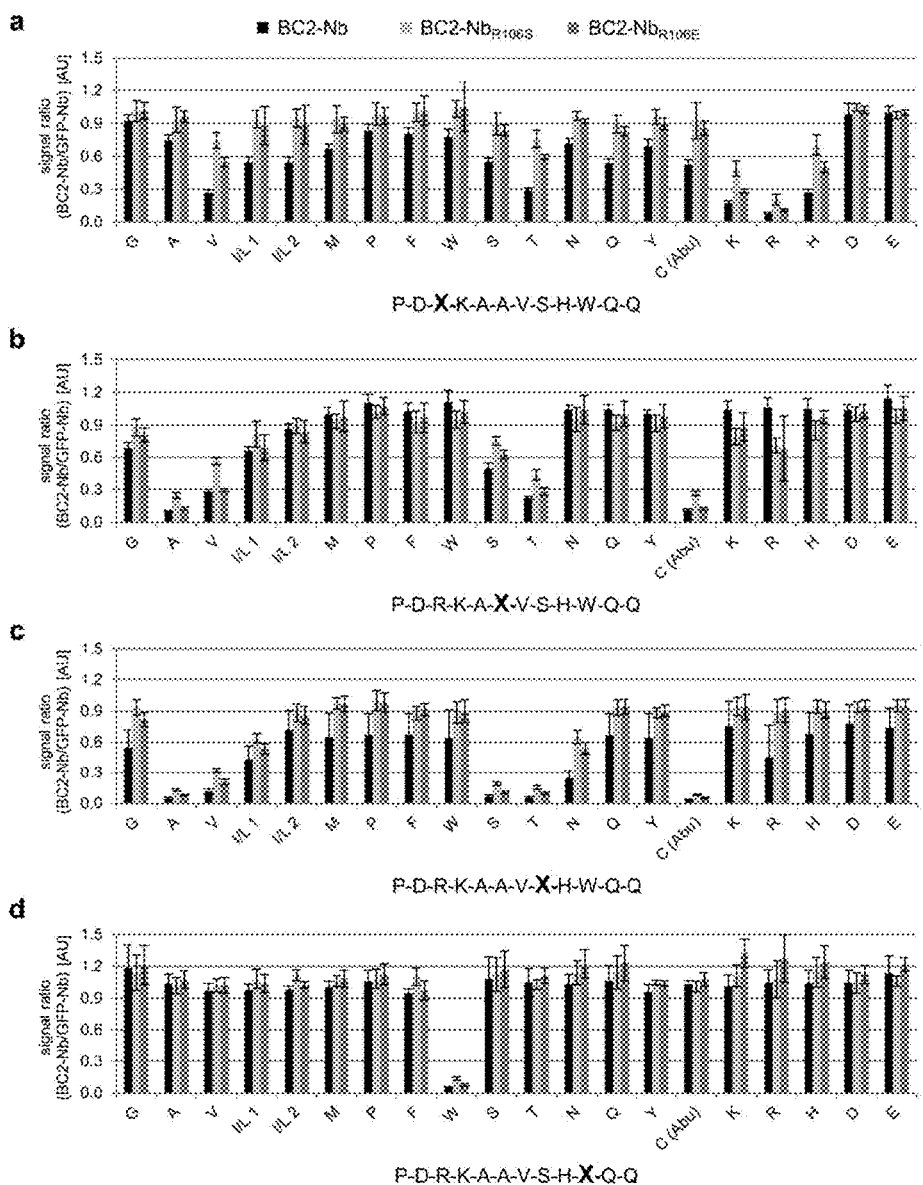

FIG. 2 shows identification of residues that mediate BC2T binding specificity. BC2T positional sequence variant libraries were incubated with BC2-Nb (black bars), BC2-Nb$_{R106S}$ and BC2-Nb$_{R106E}$ immobilized on sepharose (n=3). After precipitation the supernatants were subjected to liquid chromatography followed by mass spectrometry analysis. Specifically precipitated sequence variants were identified by calculating the ratio of signals produced by the peptides in the supernatant of BC2-Nb or indicated mutants and the supernatant of a non-BC2T-related control Nb (GFP specific Nb). Shown are results for the sequence variant libraries of (a) BC2T$_{R3X}$, (b) BC2T$_{A6X}$, (c) BC2T$_{S8X}$, and (d) BC2T$_{W10X}$ (see Table 1 for full results). Varied positions are indicated as an X in the BC2T sequence. Amino acids are grouped according to the physicochemical properties of their side chain: non-polar, polar, and charged. Gamma-amino butyric acid was used instead of cysteine in the library synthesis. Means and standard deviations (s.d.; error bars) of three independent experiments are shown.

Figure 3:
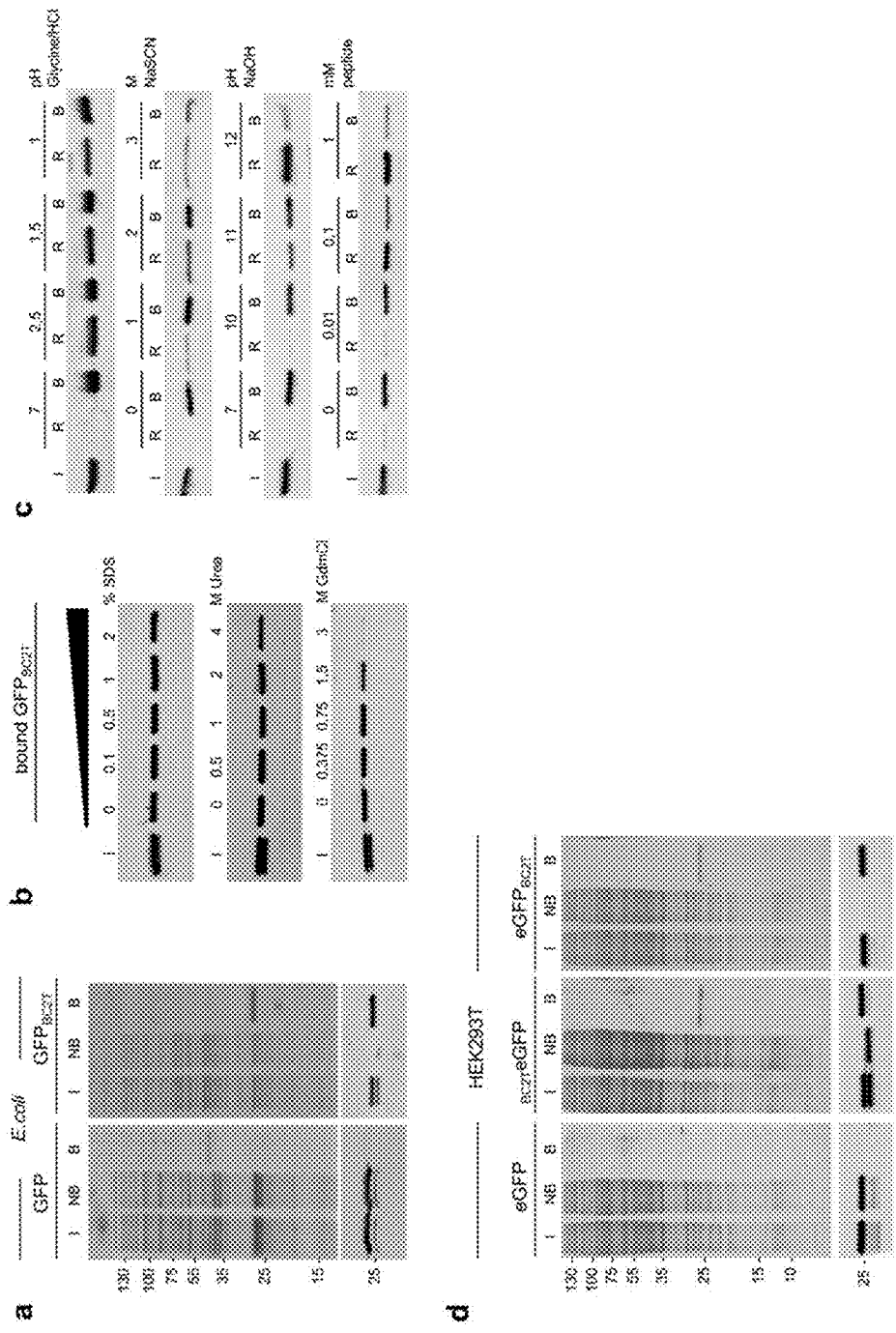

FIG. 3 shows one-step purification of BC2-tagged proteins using the BC2 nanotrap.

(a) For immunoprecipitation soluble proteins fractions of bacterial lysates either expressing GFP with a C-terminal BC2 tag (GFP$_{BC2T}$) or solely GFP were incubated with the BC2-Nb immobilized on agarose (BC2 nanotrap). Input (I), non-bound (NB) and bound fractions (B) were separated by SDS-PAGE and visualized either by Coomassie Blue (top) or by immunoblot analysis (bottom).

(b) The BC2 nanotrap efficiently binds its epitope under harsh conditions. GFP$_{BC2T}$ derived from bacterial extracts was incubated at increasing concentrations of SDS (0-2%), Urea (0-4 M) or guanidinium hydrochloride (0-3 M) and precipitated as described in (a). Shown are the Input (I) and bound fractions at indicated conditions.

(c) BC2-tagged proteins are efficiently released using alkaline pH or peptide elution. GFP$_{BC2T}$ bound to the BC2 nanotrap was subjected either to elution with sodium thiocyanate (NaSCN, 1-3 M), acidic elution (0.2 M glycine pH 1-2.5), alkaline elution (pH 10-12) or peptide elution (0-1 mM). Aliquots of released (R) and bound (B) fractions were analyzed by immunoblotting with an anti-GFP antibody.

(d) The BC2 nanotrap binds BC2-tagged proteins from human cell lysates irrespectively whether the BC2 tag is located at the N- or the C-terminus. For immunoprecipitation of BC2-tagged proteins soluble protein fractions of HEK293T cells expressing $_{BC2T}$eGFP, eGFP$_{BC2T}$ or solely eGFP were incubated with the BC2 nanotrap as described in (a). Input (I), non-bound (NB) and bound fractions (B) were separated by SDS-PAGE and visualized either by Coomassie Blue staining (top) or immunoblot analysis (bottom).

Figure 4:
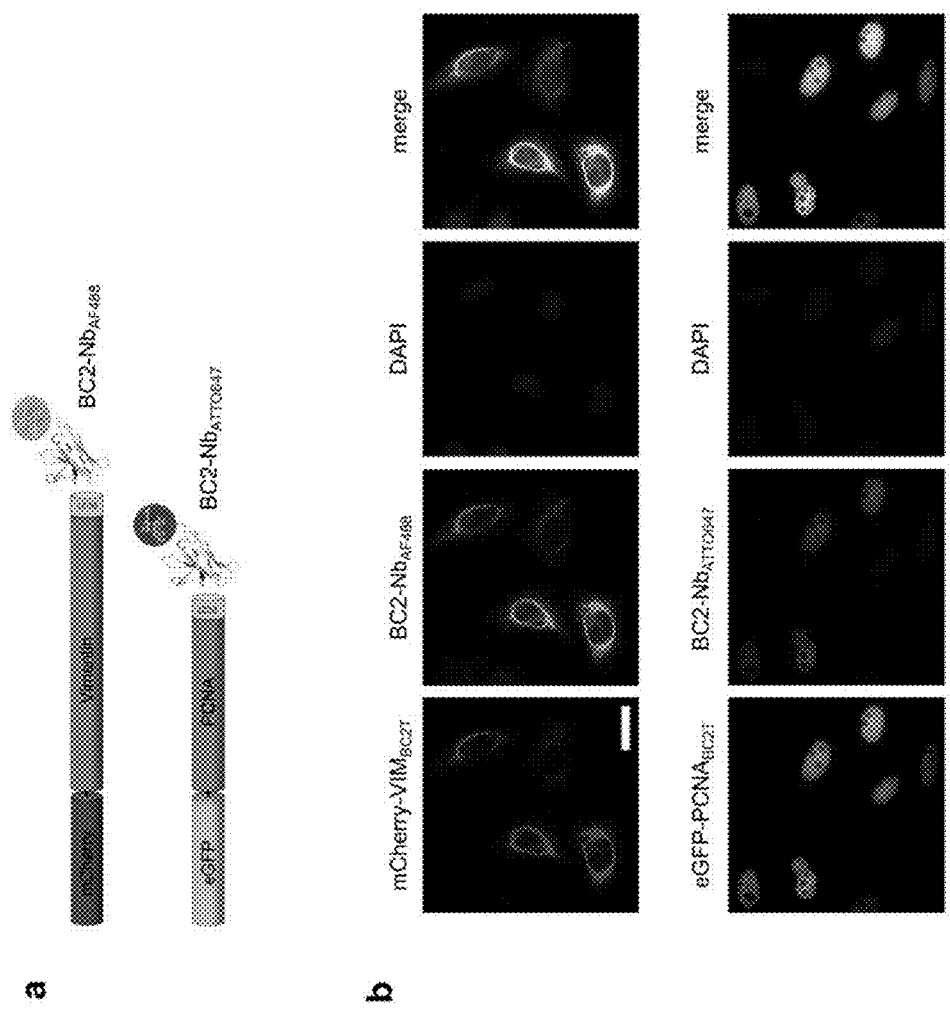

FIG. 4 shows results of immunocytochemistry experiments using a fluorescently labeled BC2 nanobody.

(a) shows a schematic representation of BC2-tagged fusion proteins and fluorescently labeled BC2-Nbs used for co-localization studies. The BC2T sequence was genetically fused to the C-terminus of mCherry-Vimentin (mCherry-VIM$_{BC2T}$) and eGFP-PCNA (eGFP-PCNA$_{BC2T}$)

(b) HeLa cells ectopically expressing mCherry-VIM$_{BC2T}$ or eGFP-PCNA$_{BC2T}$ were fixed either with methanol or PFA, respectively, followed by staining with the indicated fluorescently labeled BC2-Nbs and DAPI. Scale bar 25 µm.

Figure 5:
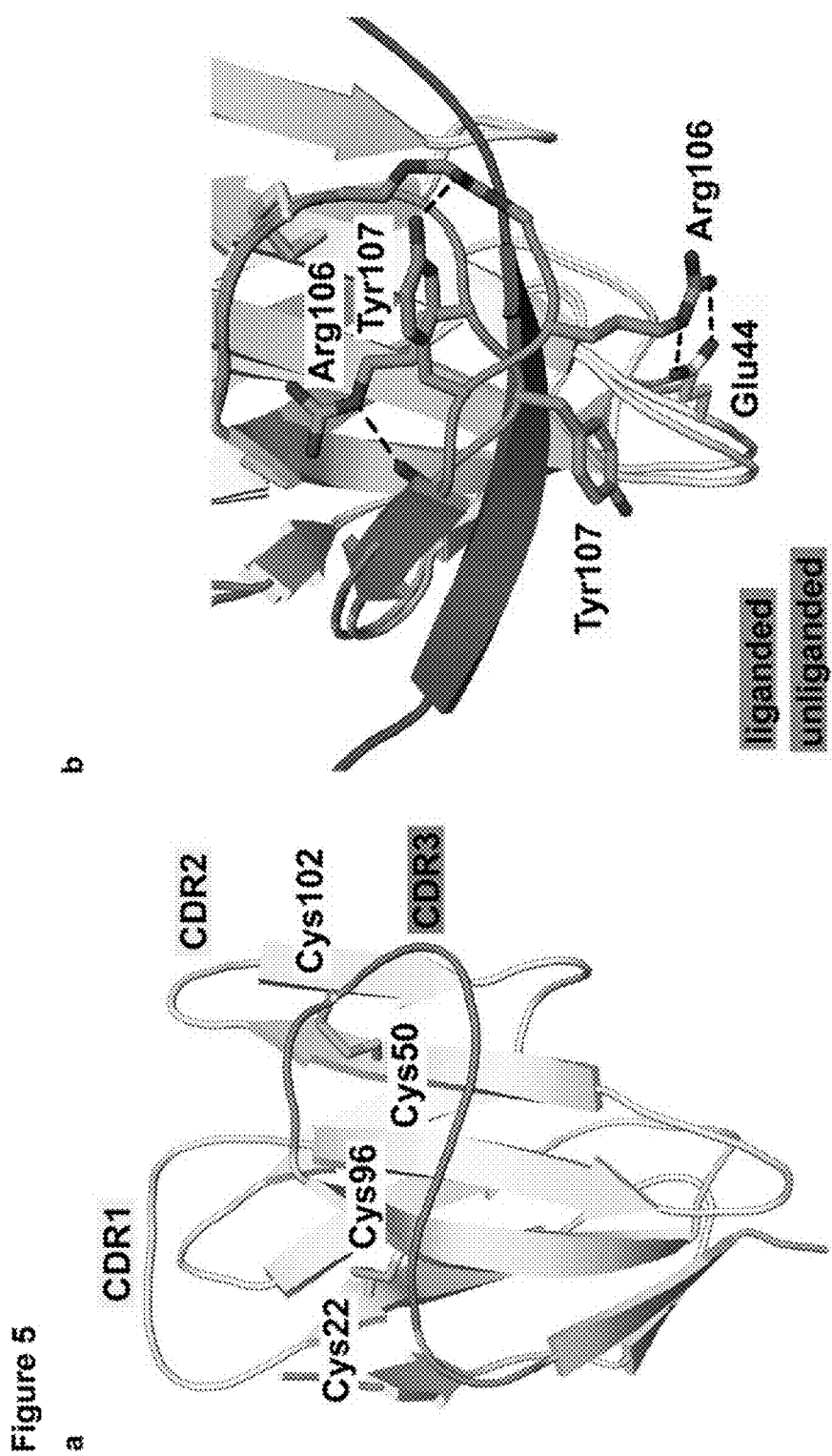

FIG. 5 shows the structure of unliganded BC2-Nb and the corresponding BC2-Nb/BC2T complex.

(a) shows a ribbon drawing of the unliganded BC2-Nb structure. The four cysteine residues forming two disulfide bonds are marked. CDR3, which contributes contacts with the peptide in the liganded structure and undergoes an amino acid flip upon binding, is highlighted.

(b) shows a superposition of unliganded and liganded BC2-Nb structures. Comparison of the two structures reveals a flip of 180 degrees by two amino acids. In the BC2-Nb structure, Arg106 is interacting with the carbonyl group of Glu108 and Tyr107 is involved in a cation π-interaction with Arg45. The β-carbon of Arg106 is orientated towards and Tyr107 away from the Nb. In the peptide bound complex structure it is the other way around. Arg106 is involved in the "headlock" binding and Tyr107 is forming a hydrogen bond to the carbonyl group of Arg104.

Figure 6:
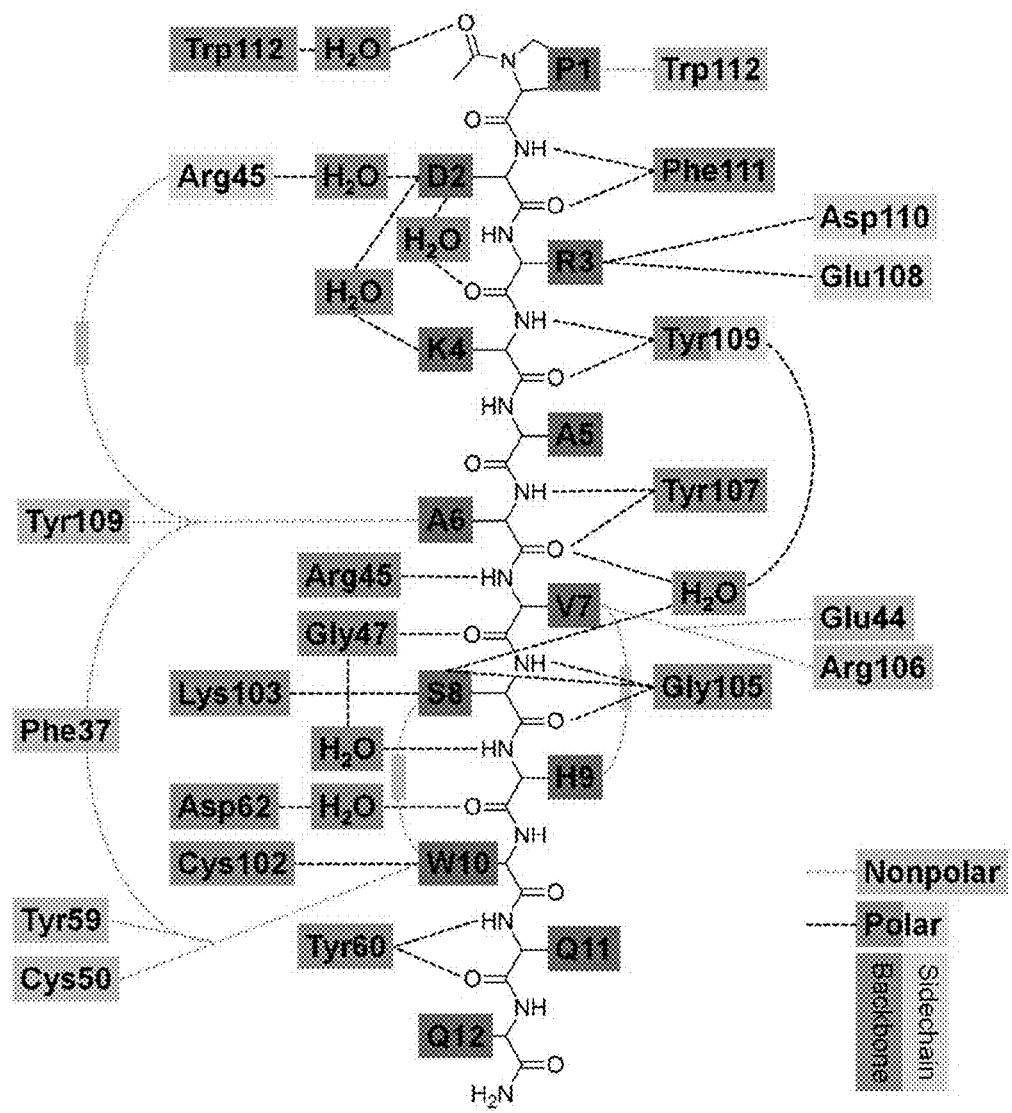

FIG. 6 shows a scheme of the interactions of the BC2-peptide with the BC2-Nb.

The BC2-peptide is shown with side chains. Its acetylated N-terminus is at the top and the amidated C-terminus is at the bottom. All polar interactions within 3.5 Å are represented with dotted black lines, with their interaction partners from the BC2-Nb for backbone and for side chain interactions. Water molecules are shown. Relevant hydrophobic interactions within 4.0 Å are represented with dotted lines.

Figure 7:
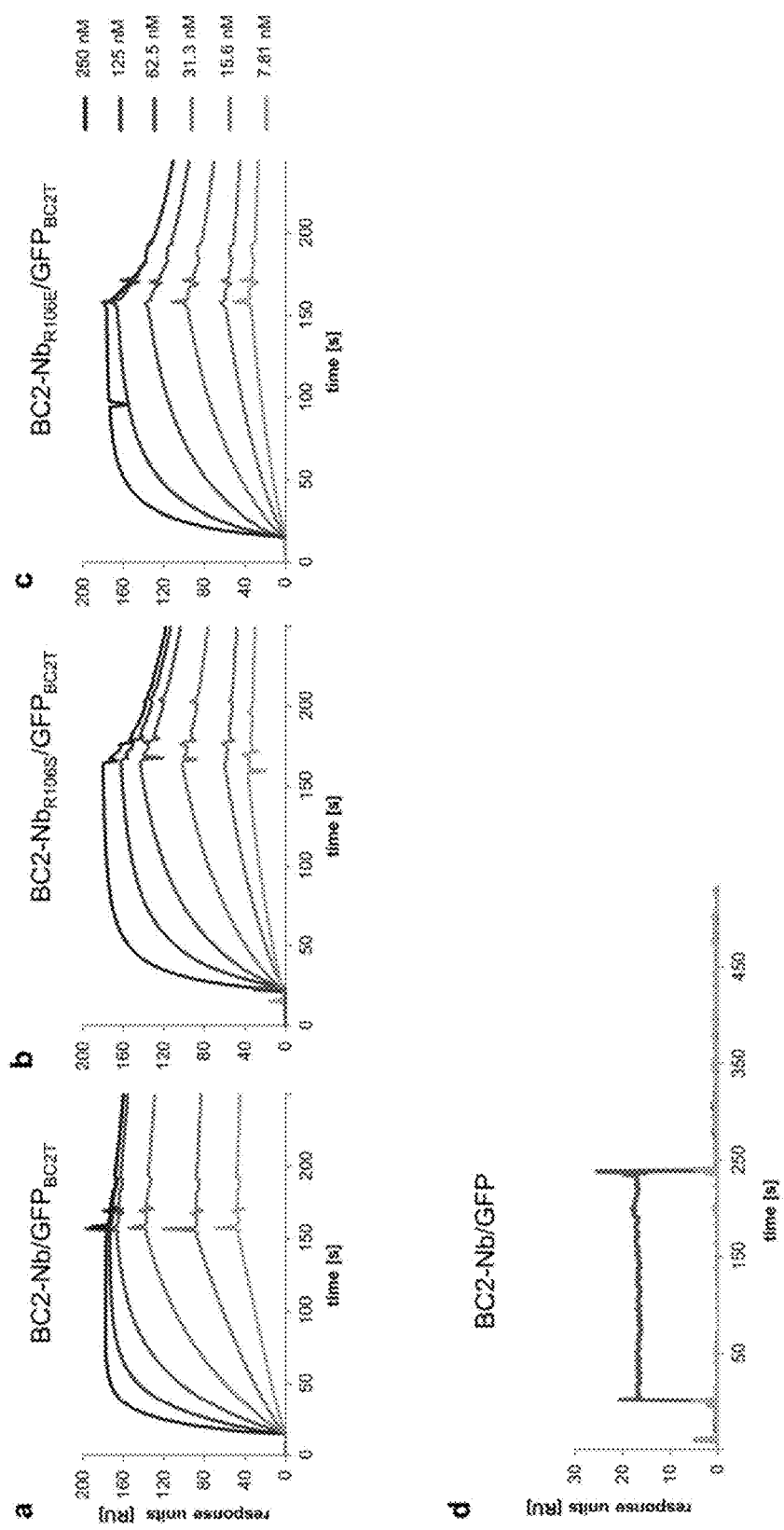

FIG. 7 shows that mutation of the headlock-motif leads to increased off-rates of the BC2 nanobody. For surface plasmon resonance spectroscopy (SPR)-based affinity measurements, GFP with a C-terminal BC2-tag (GFP$_{BC2T}$) (a-c) or solely GFP (d) was immobilized on a CMS-chip. Kinetic measurements were performed by injecting six concentrations of BC2-Nb (a), BC2-Nb$_{R106S}$ (b) or BC2-Nb$_{R106E}$ (c) ranging from 8 nM-250 nM. The obtained data sets were evaluated using the 1:1 Langmuir binding model with mass transfer. As a control, BC2-Nb was tested for binding to GFP only (d). The obtained affinities expressed in terms of the dissociation constant ($K_D$), and association ($k_{on}$) and dissociation rate constants ($k_{off}$) determined for BC2-Nb and the corresponding mutants are summarized in Table 3.

Figure 8:
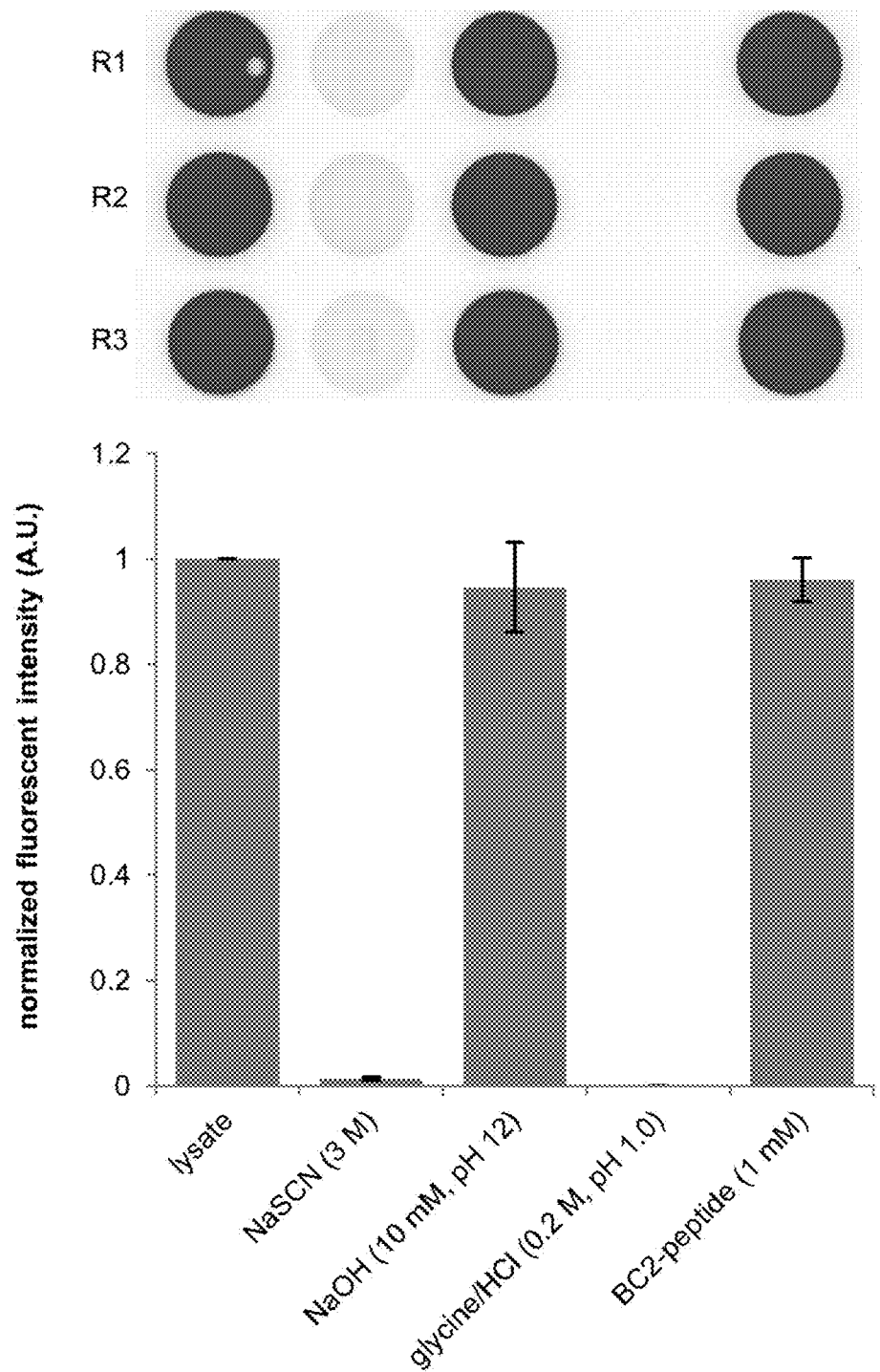

FIG. 8 shows that proteins captured by the BC2 nanotrap can be eluted under native conditions.

GFP$_{BC2T}$ derived from bacterial lysate was bound by the BC2 nanotrap and subjected to elution using buffer conditions as described in FIG. 3 *c*. The fluorescence signal intensity of released GFP$_{BC2T}$ was visualized and quantified using a laser scanner. Upper panel shows the fluorescent intensity of eluted GFP$_{BC2T}$ in comparison to the complete lysate. Lower panel: Quantification of GFP-fluorescence obtained for different elution conditions. GFP-fluorescence obtained from untreated lysate was set to 1. Means and s.d. (error bars) of three independent experiments are shown (R1-R3).

Figure 9:
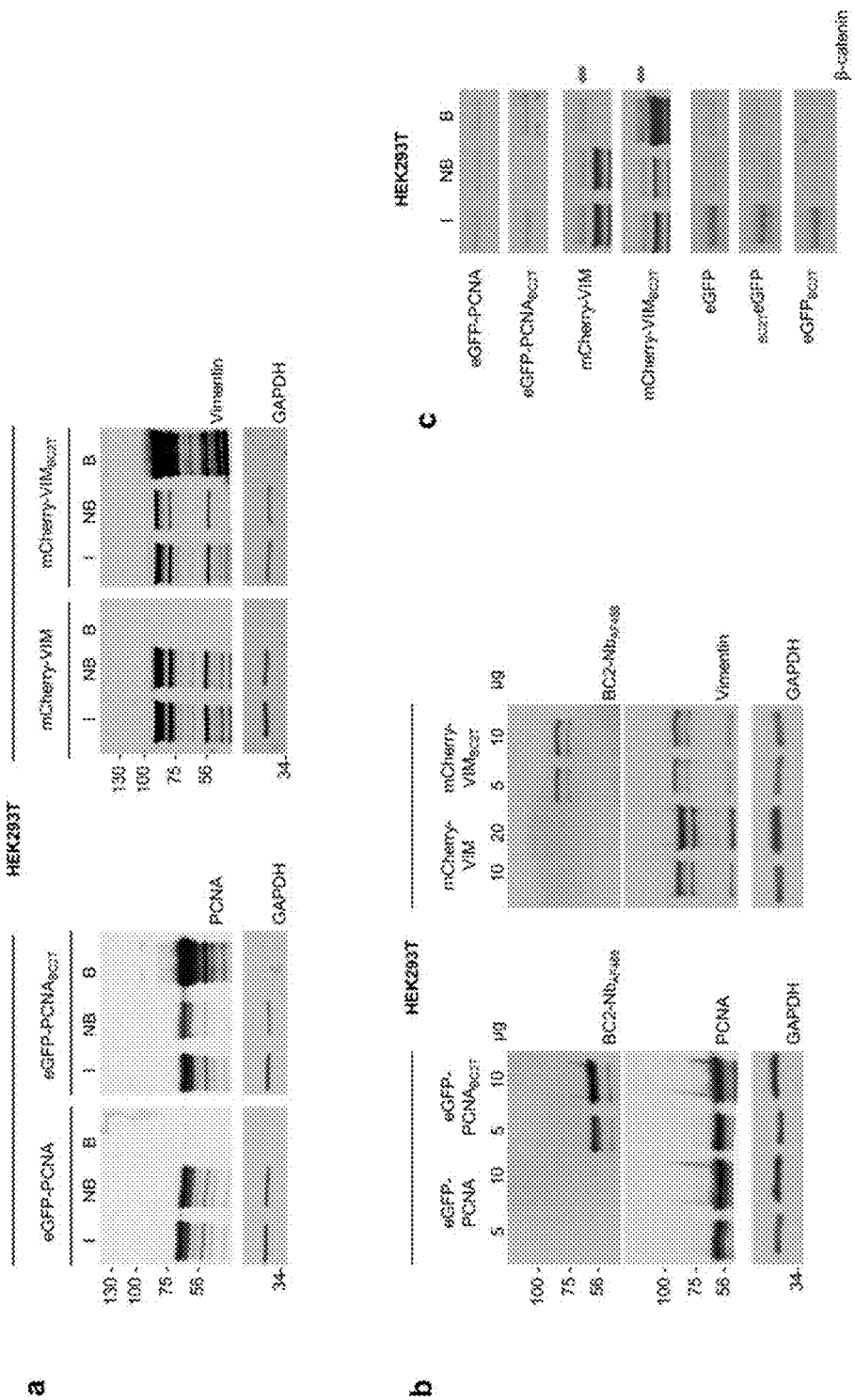

FIG. 9 shows that BC2-Nb is functional for immunoprecipitation and detection of BC2-tagged proteins.

(a) For immunoprecipitation soluble protein fractions of HEK293T cells either expressing eGFP-PCNA (control) or BC2-tagged eGFP-PCNA (eGFP-PCNA$_{BC2T}$) (left panel) or mCherry-Vimentin (mCherry-VIM, control) or BC2-tagged mCherry-VIM (mCherry-VIM$_{BC2T}$) were incubated with the BC2 nanotrap. Input (I), non-bound (NB) and bound fractions (B) were separated by SDS-PAGE and visualized either by immunoblot analysis using anti-PCNA or anti-Vimentin antibodies (upper panel). As loading control, blots were probed with an anti-GAPDH antibody (lower panel).

(b) For Western blot detection using fluorescently labeled BC2-Nb (BC2-Nb$_{AF488}$) indicated amounts of the input fractions (as shown in (a)) were subjected to SDS-PAGE and immunoblotting. The Western blots were probed with BC2-Nb$_{488}$ followed by detection with anti-PCNA (left panel) or anti-Vimentin (right panel) antibodies. As loading control blots were probed with an anti-GAPDH antibody (lower panel).

(c) shows that the BC2 nanotrap precipitates only minor amounts of endogenous β-catenin compared to overexpressed BC2-tagged proteins. Samples as described in (a) of FIG. 3 *d* were subjected to immunoblot analysis with an anti-β-catenin antibody. Arrows indicate β-catenin specific signals.

FIG. 10 shows results obtained by immunocytochemistry using fluorescently labeled BC2 nanobody.

(a) shows confocal imaging of mCherry-Vimentin$_{BC2T}$ with the BC2-Nb$_{AF488}$. HeLa cells ectopically expressing mCherry-VIM$_{BC2T}$ were fixed with methanol, followed by staining with fluorescently labeled BC2-Nb and DAPI. Shown is a maximum projection image (z-stack of 7 planes) of the cell in the lower left corner of the upper panel in FIG. 4 *b*. Scale bar 10 μm.

(b) shows specificity of BC2-Nb$_{AF488}$ and BC2-Nb$_{ATTO647}$. HeLa cells ectopically expressing untagged mCherry-VIM or eGFP-PCNA were fixed with methanol or PFA, respectively, and stained with the indicated fluorescently labeled BC2-Nbs and DAPI. Scale bar 25 μm.

Figure 11:
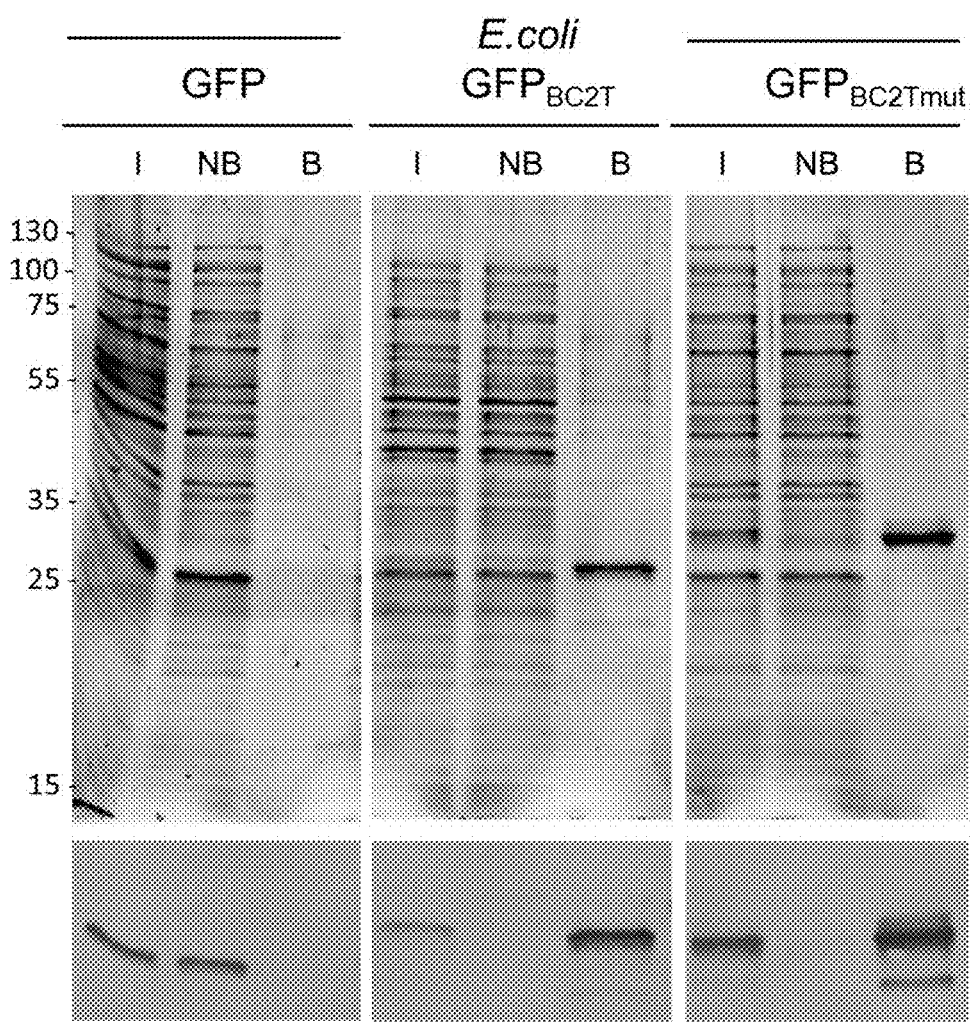

FIG. 11 shows a variation of the BC2 tag. The original BC2T sequence (PDRKAAVSHWQQ; SEQ ID NO:4) was modified in 50 percent of all positions, resulting in sequence PVRSAALSQWSS (BC2Tmut; SEQ ID NO:5).

Both the original and the modified version of the tag were C-terminally fused to GFP (GFP$_{BC2T}$; GFP$_{BC2Tmut}$). GFP without the BC2 tag was used as negative control. The proteins were expressed in *E. coli*. Lysate was prepared and 100 μg total lysate was immunoprecipitated with BC2 nanobody immobilized on agarose. Input (I), non-bound (NB) and bound (B) fractions were analyzed by SDS-PAGE followed by Coomassie staining (upper panel) or immunoblotting using an anti-GFP antibody (lower panel).

Figure 12:
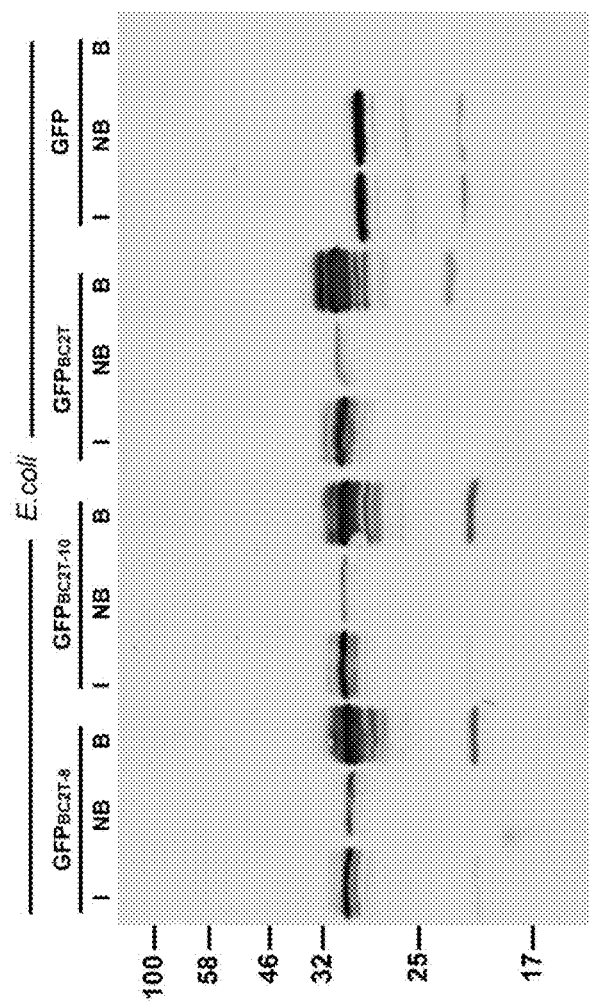

FIG. 12 shows length variations of the BC2 tag. The original BC2T sequence (PDRKAAVSHWQQ; SEQ ID NO:4) was shortened, resulting in sequence PDRKAAVSHW (BC2T-10; SEQ ID NO:14) and RKAAVSHW (BC2T-8; SEQ ID NO:3). The shortened and original versions of the tags were C-terminally fused to GFP (GFP$_{BC2T\text{-}10}$; GFP$_{BC2T\text{-}8}$, GFP$_{BC2T}$). As negative control, GFP without the BC2 tag was used. The proteins were expressed in *E. coli*. Lysate was prepared and 100 μg total lysate was immunoprecipitated with BC2 nanobody immobilized on agarose beads. Input (I), non-bound (NB) and bound (B) fractions were analyzed by SDS-PAGE followed by Western blotting using an anti-GFP antibody. The results show that the BC2T-10 sequence (PDRKAAVSHW; SEQ ID NO:14) or the BC2T-8 sequence (RKAAVSHW) (SEQ ID NO: 3) as C-terminal tag are efficiently recognized as the 12 amino acid of the original BC2T (PDRKAAVSHWQQ) (SEQ ID NO: 4) by the epitope specific BC2 nanobody.

Figure 13:
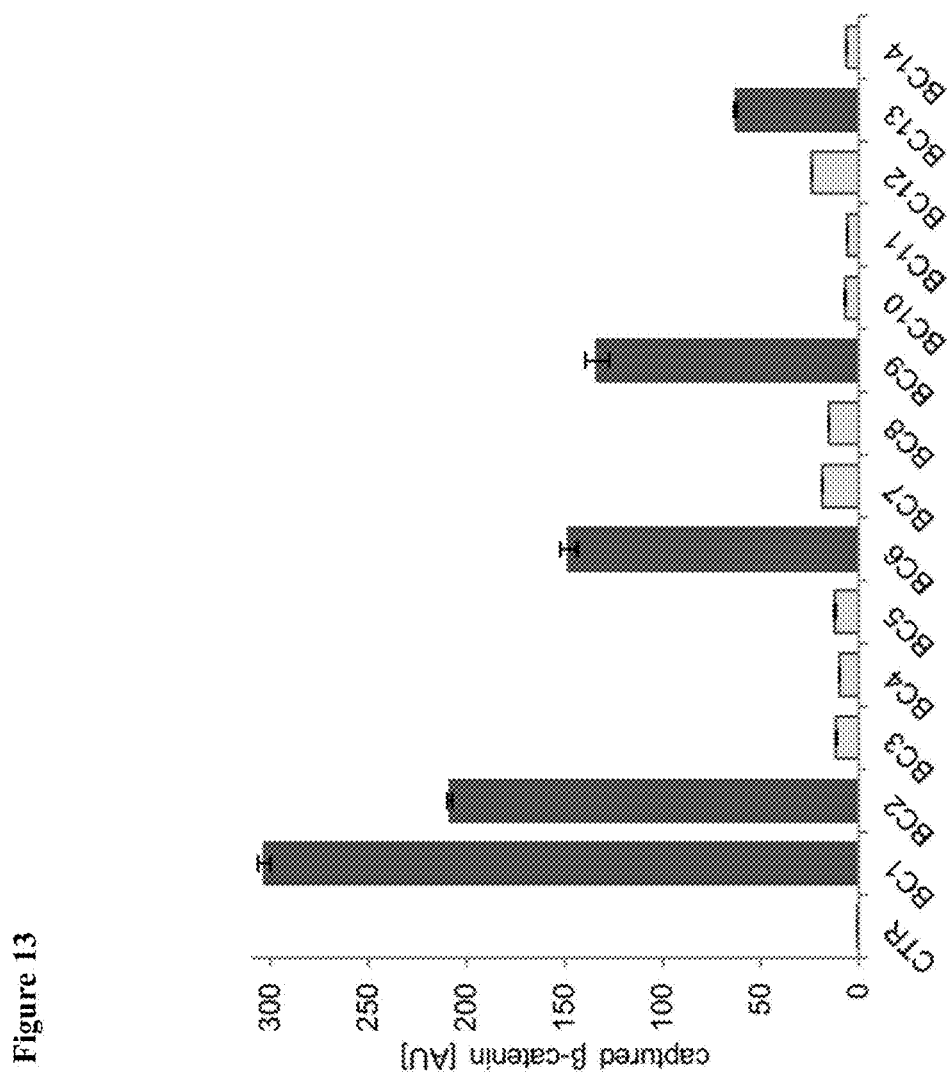

FIG. 13 shows the results of a microsphere-based sandwich immunoassay using β-catenin-specific Nbs as capture molecules. Nbs were immobilized on microspheres and incubated with increasing β-catenin concentrations ranging from 0.25 μg/ml to 2 μg/ml. Bound protein was detected with an anti-β-catenin antibody. Background level of control Nb was set to 1. Shown are mean signal intensities of three independent replicates ±s. d. Binding values of the five best Nbs are highlighted.

Figure 14:
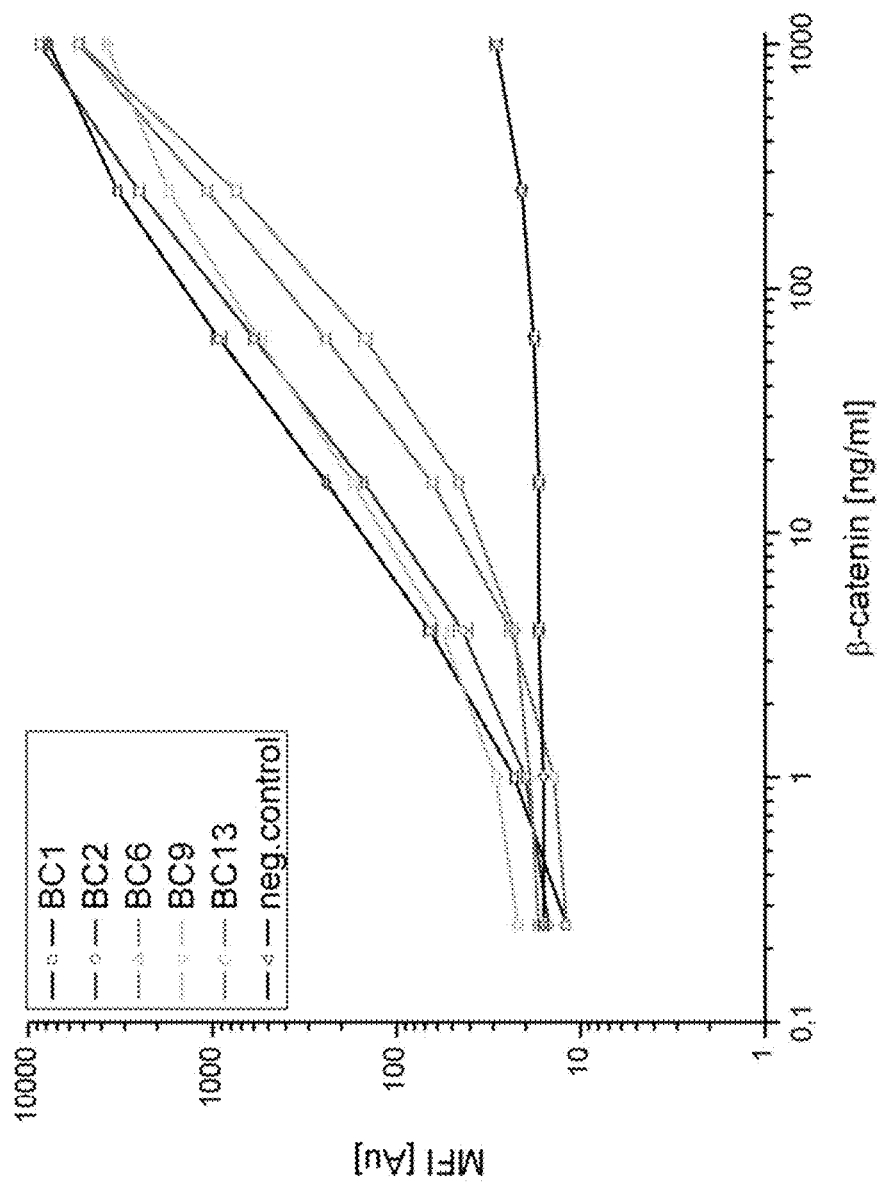

FIG. 14 shows that β-catenin-specific nanobodies show high binding sensitivities. Nbs were covalently immobilized on microspheres and incubated with serial dilutions of β-catenin ranging from 0.2 ng/ml to 1 μg/ml. Bound protein was detected with an anti-β-catenin antibody. Shown are mean signal intensities of three independent replicates ±s. d.

Figure 15:
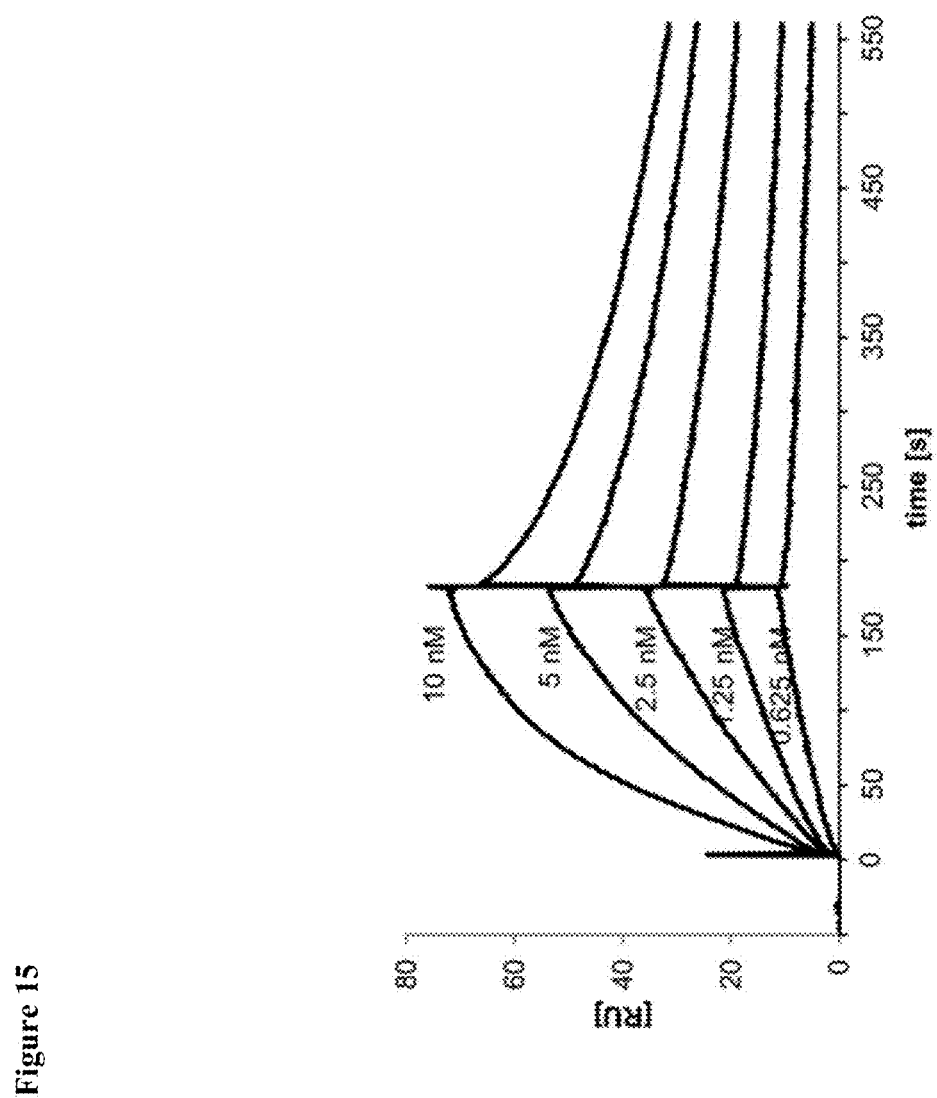

FIG. 15 shows the results of affinity measurements of BC2-Nb. BC2-Nb was used for surface plasmon resonance spectroscopy (SPR) measurements against immobilized β-catenin. SPR sensograms of BC2-Nb are shown. The Nb injection time was 180 s, followed by a dissociation time of 300 s. The data was evaluated using the software Bia evaluation 4.1 and the 1:1 Langmuir binding model.

Figure 16:
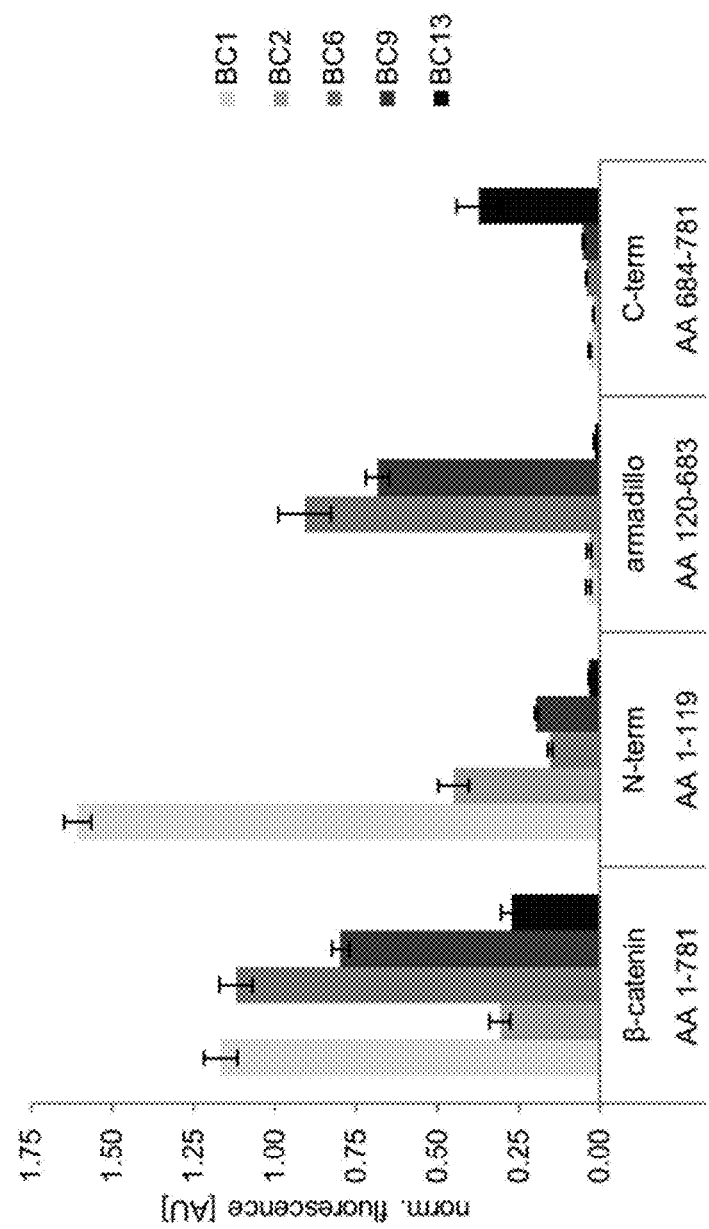

FIG. 16 shows the results of domain mapping of β-catenin binders. Microsphere-immobilized Nbs were incubated with GST-fusion constructs comprising full-length β-catenin or indicated domains. Captured β-catenin constructs were detected with domain-specific antibodies. For direct comparison, fluorescence intensities obtained with domain-specific antibodies were normalized to signals obtained with an anti-GST-antibody.

Figure 17:
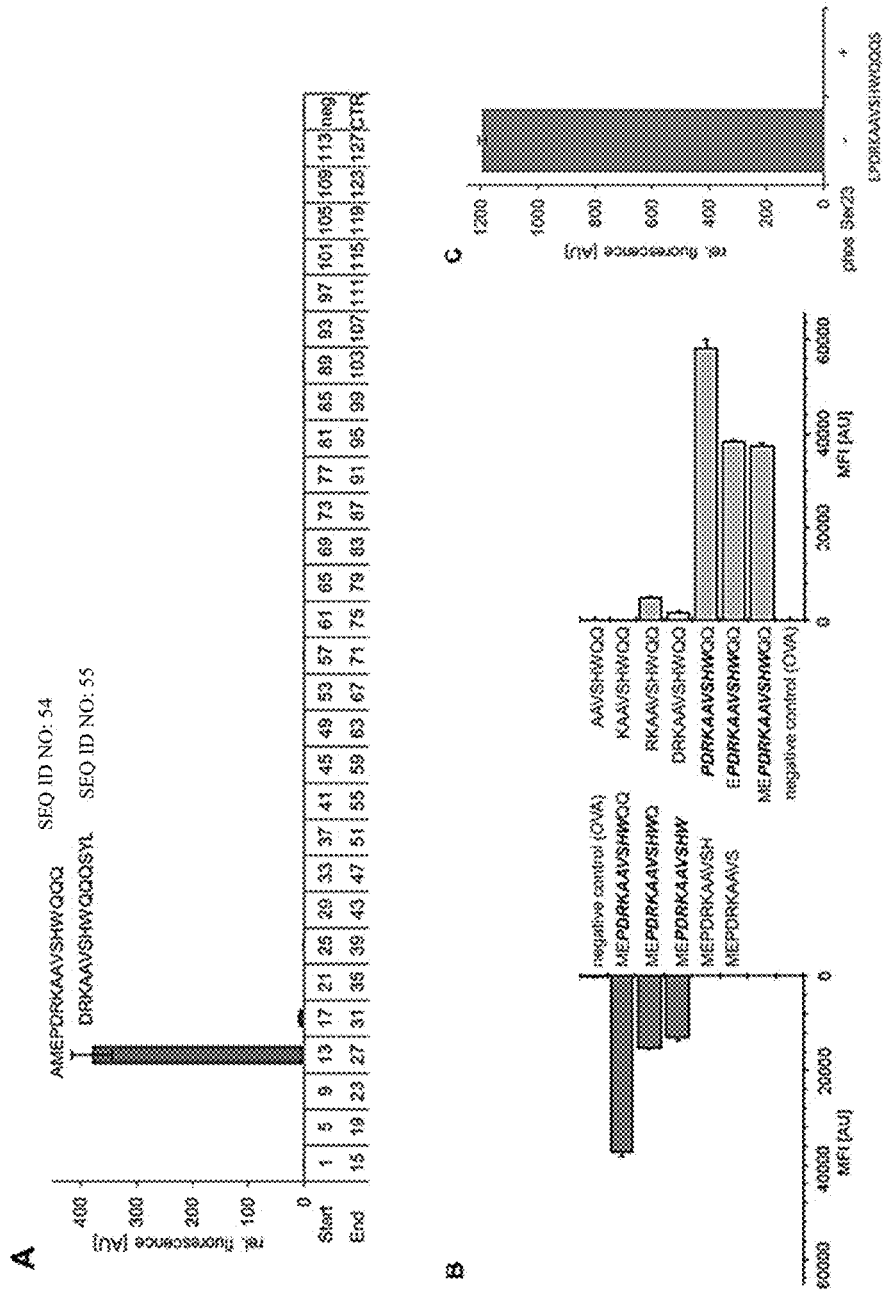

FIG. 17 shows the results of epitope mapping of BC2-Nb.

(A) shows the identification of the epitope recognized by BC2. In a peptide screen 29 overlapping 15-mer peptides covering the N-terminus from aa 1-127 of β-catenin were immobilized on microspheres with varying IDs per peptide and incubated with biotinylated BC2-Nb. Peptide-bound BC2-Nb was detected with streptavidin-phycoerythrin (PE) solution. The Myc-peptide (EQKLISEEDL) (SEQ ID NO: 53) was used as negative control (neg CTR).

(B) shows the determination of the minimal epitope of BC2-Nb. Incubation of serial N- and C-terminally truncated peptides covering aa 14-27 of β-catenin with biotinylated BC2-Nb MEPDRKAAVSHWQQ (SEQ ID NO: 56), MEPDRKAAVSHWQ (SEQ ID NO: 57), MEPDRKAAVSHW (SEQ ID NO: 58), MEPDRKAAVSH (SEQ ID NO: 59), MEPDRKAAVS (SEQ ID NO: 60), EPDRKAAVSHWQQ (SEQ ID NO: 61), PDRKAAVSHWQQ (SEQ ID NO: 4), DRKAAVSHWQQ (SEQ ID NO: 62), RKAAVSHWQQ (SEQ ID NO: 63), KAAVSHWQQ (SEQ ID NO: 64), AAVSHWQQ (SEQ ID NO: 65). Peptide-bound BC2 nanobodies were detected with streptavidin-phycoerythrin (PE). Amino acid residues comprising the minimal epitope of BC2-Nb are highlighted. Shown are mean signal intensities of three independent replicates ± stds.

(C) shows that phosphorylation of the epitope abolishes binding by BC2-Nb. Binding analysis of BC2-Nb to a peptide representing aa 15-29 with (+) or without (−) a phosphorylated Ser23 (phos Ser23) EPDRKAASVSH-WQQQS (SEQ ID NO: 66) was performed as described in (B). Columns represent mean signal intensities of three independent experiments ± stds.

Figure 18:
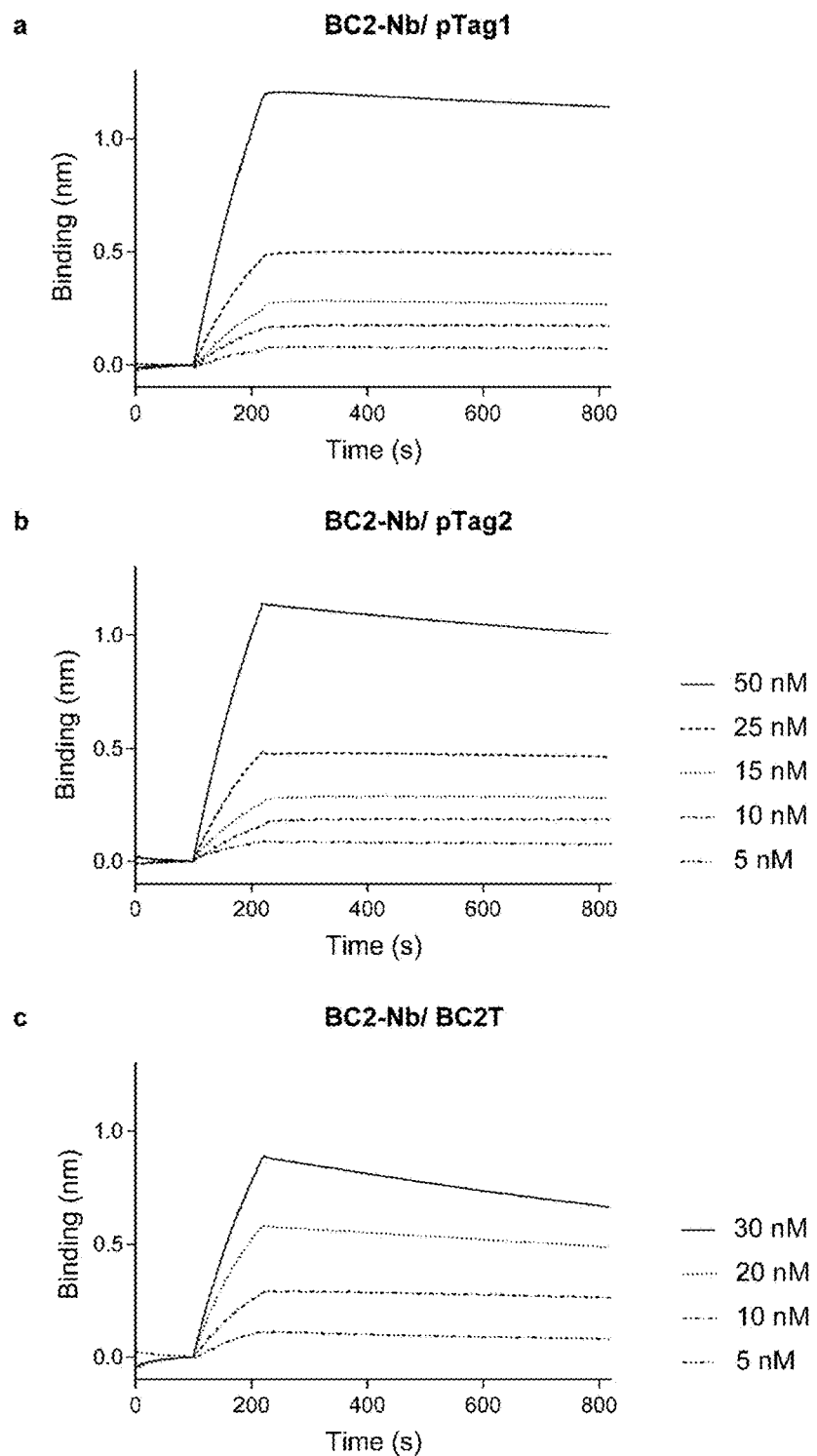

FIG. 18 shows two variations of the BC2 tag with improved binding affinities over the wildtype BC2 tag. Biolayer interferometry (BLI)-based affinity measurements were used to assess two improved variations of the original BC2T sequence (a: PDRVRAVSHWSS, pTag1 SEQ ID NO:33; b: ADRVRAVSHWSS, pTag2 SEQ ID NO:34) in comparison with the original BC2T sequence (c: BC2T SEQ ID NO:4). BC2T and improved variations thereof were synthesized as peptides with an N-terminal biotin attached through an ethylene glycol linker and immobilised on Streptavidin biosensors. Binding kinetics were analysed by incubating immobilised peptides with 4-5 concentrations of BC2-Nb (5-50 nM) and evaluated using a 1:1 binding model. The obtained dissociation constants ($K_D$), association ($k_{on}$) and dissociation rate constants ($k_{off}$) are summarised in Table 5.

Figure 19:
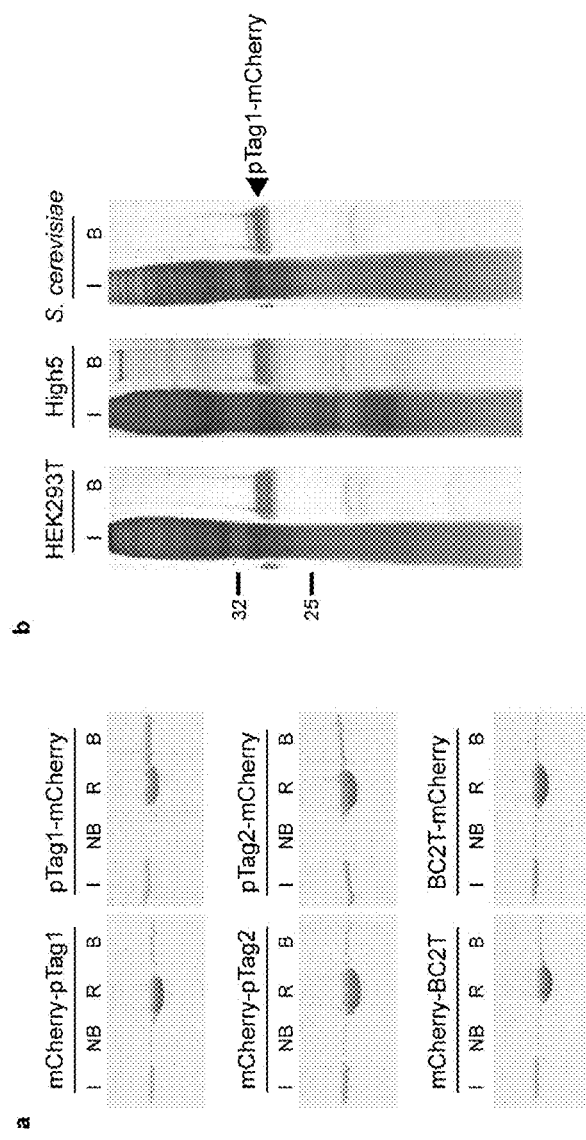

FIG. 19 shows the application of two improved variations of the BC2 tag to protein purification and immunoprecipitation.

(a) Protein purification: The BC2 nanotrap was incubated with the protein mCherry tagged N-terminally or C-terminally with the original BC2 tag BC2T (SEQ ID NO:4) or improved variations thereof (pTag1 SEQ ID NO:33 and pTag2 SEQ ID NO:34). Subsequently, bound protein was eluted using the corresponding free peptide at a concentration of 100 µM. Fractions of input (I), non-bound protein (NB), protein released by peptide elution (R) and protein still bound after elution (B) were analysed using SDS-PAGE and Coomassie staining.

(b) Immunoprecipitation: The BC2 nanotrap was used to precipitate the protein mCherry fused N-terminally with the BC2 tag variation pTag1 SEQ ID NO:33 from lysates of the human cell line HEK293T, the *Trichoplusia ni* insect cell line High5 and the yeast *Saccharomyces cerevisiae*. Fractions of input (I) and bound protein (B) were analysed using SDS-PAGE and Coomassie staining.

DEFINITIONS

In this description and the claims, reference will be made to a number of terms which shall be defined to have the following meanings:

The term "epitope peptide" or "epitope tag" shall refer to a peptide sequence that is used as a tag; both terms are used interchangeably. An epitope peptide is any peptide that comprises at least the 8 amino acid sequence as defined in SEQ ID NO: 1 ($RX_4X_5AX_7SX_9W$), wherein $X_4$ can be K or a substitution; wherein $X_5$ can be A or R or a conservative substitution of A or R; wherein $X_7$ can be V or a conservative substitution of V, and wherein $X_9$ can be H or a conservative substitution of H. An epitope tag can also consist of SEQ ID NO: 1 ($RX_4X_5AX_7SX_9W$), wherein $X_4$ can be K or a substitution; wherein $X_5$ can be A or R or a conservative substitution of A or R; wherein $X_7$ can be V or a conservative substitution of V, and wherein $X_9$ can be H or a conservative substitution of H.

Isolated epitope peptides are also provided wherein, when the isolated peptide comprises at least 9 amino acids, the peptide does not comprise an amino acid sequence as defined by SEQ ID NO: 3 (RKAAVSHW). The epitope peptide or epitope tag can be an isolated sequence or can be part of a sequence.

The term "epitope specific antibody" shall refer to an antibody that is specific to the epitope provided herein and can also be referred to as tag specific antibody, or epitope tag specific antibody, these terms can be used interchangeably.

The term "polypeptide" refers to any type of polypeptide or protein and comprises any amino acid sequence wherein amino acids are connected via peptide bonds, such as an amino acid sequence of at least 10 amino acids in length, with the proviso that the construct of epitope tag and polypeptide is not ß-catenin. The term polypeptide is used in this application very generally and shall comprise also peptides, such as oligopeptides. The terms polypeptide and protein are used interchangeably.

The term "polypeptide of interest" or "protein of interest" shall refer to any type of polypeptide or protein having a function or property, such as a physiologically active molecule and comprises all structure variants and sequence variants that have a desired property or function. In particular, the term shall encompass any type of peptide and protein as well as to a fusion protein. Both terms are used interchangeably.

The term "fusion protein" or "fusion polypeptide" shall refer to a protein or a polypeptide created through the joining of two or more polypeptides or at least one polypeptide and at least one peptide or at least one polypeptide and at least one oligopeptide.

For example, a "fusion protein" can refer to a polypeptide comprising the amino acid sequence of a protein fused with the amino acid sequence of an epitope peptide. The fusion protein or fusion polypeptide can comprise one or more than one polypeptide and one or more than one epitope peptide. Moreover, the fused peptides can be joined via a bridge or linker sequence. The epitope peptide is preferably fused to the N- or C-terminal end of the amino acid sequence of the protein, either directly or via a linker molecule.

A linker is any unit that connects two parts of a molecule, such as two nucleic acids, two peptides or proteins, a tag and a protein of interest, or a nucleotide, peptide or protein and a carrier. Any unit that is known for this purpose can be used as long as it does not interfere with the function of the molecule. The linker can be comprised of nucleotides when the connected members are nucleic acids, for example 3 to 150 nucleotides, or can be one amino acid or an amino acid sequence having 2 to 50 amino acids, when at least one of the two parts is a peptide or protein, or another bridge molecule.

A variant of an epitope peptide of the present invention is a peptide, comprising at least 8 amino acids that on positions 1, 4, 6, and 8 has amino acids 1, 4, 6 and 8 of SEQ ID NO:3, whereas the remaining amino acids can be amino acids of SEQ ID NO:3 and at least one of those is another amino acid that regarding size, polarity and/or charge, is similar to the "original" amino acid of SEQ ID NO:3. In other words, the term "variant" as used in this description refers to a sequence that is derived from or corresponds to SEQ ID NO:3 wherein at least 12.5% and up to 25, or 37.5, or 50% of the amino acids are substituted by substitutions, like conservative substitutions. For example, a lysine can also be substituted by a serine without changing the function of the peptide. A variant of the present invention can be an epitope peptide as defined above wherein 4 out of 8 amino acids of the sequence of SEQ ID NO:3 can be substituted without substantially changing the function of the peptide. A variant of an epitope peptide of the present invention having 8 amino acid residues comprising 3 conservative substitutions, resulting in a 37.5% conservatively substituted variant has been shown to be active in the examples.

The epitope tag of the present invention being located at the C-terminal or N-terminal end means that no other amino acid residues derived from the sequence of the polypeptide of interest are preceding the sequence of the epitope tag at the N-terminal end or following the sequence of the epitope tag at the C-terminal end. Sequences not derived from the original sequence of the polypeptide of interests, such as further tags or linker sequences, can however follow or precede the C- or N-terminal tag of the present invention.

The terms "purification" or "purify" when used in the present application shall refer to any type of physical separation of a chemical or biochemical entity of interest from a material, such as a biochemical material. An example is the purification of a polypeptide from a biochemical mass like a tissue or broth. Purified entities can also be referred to as isolate. Protein or polypeptide purification can comprise one step or a series of steps intended to isolate or enrich one or a few proteins from a sample. Purification is vital for the characterization of the function, structure and interactions of the protein of interest. Purification can comprise to separate protein from non-protein parts of a sample or to separate a desired protein from other proteins. The result of purification can be an isolated protein or a sample wherein the polypeptide is enriched. In the present application the term "purification" encompasses all types of separation and encompasses isolation as well as enrichment.

The term "sample" refers to a specimen or a quantity that is used for any type of determination or purification method. The sample comprises a tag and/or protein of interest, it can be a liquid or a solid. In the context of the present invention a sample can be often a complex mixture comprising the protein of interest, such as a cell, a tissue or cell lysate. A sample can also be a supernatant obtained by centrifugation of a liquid comprising a cell, where the cell is capable of secreting the protein of interest into the liquid. A sample can also be a specimen of any type of body fluid like blood, urine, liquor, sweat, tears, etc.

The term "secondary binding partner" refers to compounds that can specifically or unspecifically bind to a tagged polypeptide, an epitope specific affinity ligand such as an antibody or a complex formed by both as a primary binding partner, either directly or via a unit provided at the polypeptide or the affinity ligand such as an antibody. One example for a binding pair is a constant part of an epitope specific antibody and an Fc specific antibody. Another example for a binding pair is a biotin moiety present on the tagged polypeptide or the epitope specific antibody and a streptavidin. A further example as secondary binding partner is an antibody against the complex. The secondary binding partner can be used for isolating the complex and/or for detecting the complex. For this purpose the secondary binding partner can carry immobilizable groups, detectable groups, etc.

DETAILED DESCRIPTION

Provided herein is an epitope peptide sequence, which is defined as SEQ ID NO:1. It has been surprisingly found that a peptide sequence comprising at least the eight amino acids of SEQ ID NO:3 (RKAAVSHW) or variants thereof are useful as an epitope tag. This amino acid sequence is sufficient for specific binding as the affinity of its antibody to the epitope is high enough to ensure specific and reliable interaction with the tag. Furthermore, it has been found that a system for capture and/or detection based on the epitope peptide has very desirable properties. For example it has been shown that epitope-tagged proteins are bound by an epitope specific antibody with a $K_D$ of ~1.4 nM which translates to a ~10-100 fold higher affinity compared to the systems available in the prior art, such as FLAG, HA, c-myc or the nanobody-derived EPEA-systems. The epitope peptide provided herein is very versatile; it can be used as C-terminal or N-terminal tag and shows strong binding to the corresponding antibody under mild or harsh conditions. One or more tags can be used, which can be the same or different as long as at least one of the tags is an epitope tag provided herein, for example and not to be limiting, an epitope tag consisting of or comprising SEQ ID NO: 3 or SEQ ID NO: 3 with one or more substitutions, and which can be located on different ends of the polypeptide or which can be arranged tandem-like or in any other order. In particular the system for detection and/or capture shows unusually strong affinity and binding efficiency because of its unique binding characteristics.

Moreover, it has been surprisingly found, that only four amino acids of SEQ ID NO: 3 (R at position 1, A at position 4, S at position 6, and W at position 8 with reference to the amino acid residues in SEQ ID NO:3), are essential for specific binding of a tag specific antibody and that the remaining positions can be substituted such as by another amino acid that regarding size, polarity and/or charge is similar to the "original" amino acid, and preferably is substituted conservatively, without significantly negatively impacting the binding specificity and affinity. For example, these substitutions can be one or more non-naturally occurring amino acid substitutions. It has been found that an epitope tag comprising, preferably conservative, substitutions at up to 50% of the amino acids comprised in the polypeptide as defined in SEQ ID NO:4 still ensures efficient and reliable interaction of the epitope specific antibody with the tagged proteins. It has also been found that peptides having additional amino acids on one or both ends provide for efficient and reliable interaction with a epitope specific antibody. As an example, a modified tag or epitope peptide having the amino acid sequence PVRSAALSQWSS (SEQ ID NO:5) was used to efficiently purify tagged GFP protein (see FIG. 11). Further examples of a modified tag or epitope peptide consist of or comprise an amino acid sequence as defined by SEQ ID NO:33 (PDRVRAVSHWSS), or consist of or comprise an amino acid sequence as defined by SEQ ID NO: 34 (ADRVRAVSHWSS).

It has been found that the epitope tag provided herein can comprise further amino acids flanking the central tag sequence. Although tag sequences with a length of more than 25 amino acids could be used, it is beneficial to provide a smaller tag in order to minimize interference of the tag with the subcellular locations, interference with folding, or interference with functions of the polypeptides or proteins fused with the tag. Thus, the epitope peptide comprising the tag can be an epitope peptide that does not comprise more than 25 amino acids. For example, the epitope peptide can comprise about 8, 9, 10, 11, 12, 13, 14, 15, 16, 17, 18, 19, 20, 21, 22, 23, 24 or 25 amino acids or consist of about 8, 9, 10, 11, 12, 13, 14, 15, 16, 17, 18, 19, 20, 21, 22, 23, 24 or 25 amino acids The epitope peptide can also consist of 25 amino acids or less.

For example, and not to be limiting, the epitope peptide or tag consists of or comprises from about 8 to about 25 amino acids, wherein the amino acid sequence consists of or comprises a sequence as defined in SEQ ID NO:1 ($RX_4X_5AX_7SX_9W$), wherein $X_4$ can be K or a substitution;
wherein $X_5$ can be A or a conservative substitution of A;
wherein $X_7$ can be V or a conservative substitution of V; and
wherein $X_9$ can be H or a conservative substitution of H.
In some examples $X_4$ can be a conservative substitution of K or S.

In another example, the epitope peptide or tag consists of or comprises from about 8 to about 25 amino acids, wherein the amino acid sequence consists of or comprises a sequence as defined in SEQ ID NO:1 ($RX_4X_5AX_7SX_9W$), wherein $X_4$ can be K or a substitution;
wherein $X_5$ can be A or a conservative substitution of A;
wherein $X_7$ can be V or a conservative substitution of V; and
wherein $X_9$ can be H or a conservative substitution of H, wherein, when the isolated epitope peptide comprises at least 9 amino acids, it does not comprise an amino acid sequence as defined by SEQ ID NO:3 (RKAAVSHW). In some examples, $X_4$ can be a conservative substitution of K or S.

In any of the epitope peptides described herein, one or more of the amino acid substitutions can be a non-naturally occurring substitution. It is understood that any of the epitope peptides provided herein can comprise one or more substitutions described herein. For example, the epitope peptide can consist of or comprises a sequence as defined in SEQ ID NO:1 ($RX_4X_5AX_7SX_9W$), with one or more substitutions at positions $X_4$, $X_5$, $X_7$ and $X_9$, as described herein. In another example, the epitope peptide can consist of or comprises a sequence as defined in SEQ ID NO:32 ($X_1X_2RX_4X_5AX_7SX_9WX_{11}X_{12}$), with one or more substitutions at positions $X_1$, $X_2$, $X_4$, $X_5$, $X_7$, $X_9$, $X_{11}$, or $X_{12}$, as described herein In another example, the epitope peptide consists of or comprises from about 12 to 25 amino acids, wherein the amino acid sequence consists of or comprises a sequence as defined in SEQ ID NO:32 ($X_1X_2RX_4X_5AX_7SX_9WX_{11}X_{12}$)

wherein X1 can be P or A;
wherein $X_2$ can be D or a conservative substitution of D;
wherein $X_4$ can be K or a substitution;
wherein $X_5$ can be A or R, or a conservative substitution of A or R;
wherein $X_7$ can be V or a conservative substitution of V;
wherein $X_9$ can be H or a conservative substitution of H; and
wherein $X_{11}$ and $X_{12}$ can be Q or a conservative substitution of Q.
In some examples, $X_4$ can be a conservative substitution of K or S.

In another example, the epitope peptide consists of or comprises from about 12 to 25 amino acids, wherein the amino acid sequence consists of or comprises a sequence as defined in SEQ ID NO:32 ($X_1X_2RX_4X_5AX_7SX_9WX_{11}X_{12}$)

wherein $X_1$ can be P or A;
wherein $X_2$ can be D or a conservative substitution of D;
wherein $X_4$ can be K or a substitution;
wherein $X_5$ can be A or R, or a conservative substitution of A or R;

wherein $X_7$ can be V or a conservative substitution of V;
wherein $X_9$ can be H or a conservative substitution of H; and
wherein $X_{11}$ and $X_{12}$ can be Q or a conservative substitution of Q, wherein the isolated epitope peptide does not comprise an amino acid sequence as defined by SEQ ID NO:3 (RKAAVSHW). In some examples, $X_4$ can be a conservative substitution of K or S.

One or more of the amino acid substitutions can be a non-naturally occurring substitution.

In another example, the epitope peptide consists of or comprises an amino acid sequence as defined by SEQ ID NO:4 (PDRKAAVSHWQQ) or a variant thereof as defined above.

A "conservative substitution" refers to the substitution of one amino acid by another, wherein the replacement results in a silent alteration. This means that one or more amino acid residues within the epitope peptide sequence can be substituted by another amino acid of a similar polarity which acts as a functional equivalent. Substitutes for an amino acid within the sequence may be selected from other members of the class to which the amino acid belongs (i.e. a conservative substitution). For example, one polar amino acid can be substituted by another polar amino acid, one positively or negatively charged amino acid, respectively, can be substituted by another positively or negatively charged amino acid, respectively, et cetera. Classes of amino acids are for example, nonpolar (hydrophobic) amino acids including alanine (A), leucine (L), isoleucine (I), valine (V), proline (P), phenylalanine (F), tryptophan (W) and methionine (M); polar neutral amino acids including glycine (G), serine (S), threonine (T), cysteine (C), tyrosine (Y), asparagine (N), and glutamine (Q); positively charged (basic) amino acids including arginine (R), lysine (K) and histidine (H); negatively charged (acidic) amino acids including aspartic acid (D) and glutamic acid (E).

The epitope peptide is provided in isolated form, which means that is not comprised within the body of an animal or a human being. The epitope peptide can be provided as isolated peptide or it can be used in conjugated, linked, bound, or connected form, like in a fusion protein wherein at least one epitope is fused to a polypeptide, in particular a protein or polypeptide of interest, or in a construct which comprises at least one epitope provided herein and a polypeptide, optionally linked or connected by a linker, spacer or other connecting member. The linker, spacer or other connecting member can be any sequence as is known in the art. It can for example be a sequence providing for a cleavage site, or can just be a spacer, i.e. a member that adjusts the distance between epitope and polypeptide, or a connecting member contributing a desirable function.

It has been surprisingly found that this epitope peptide can be efficiently and reliably used as an epitope tag, which can interact specifically and efficiently with an epitope specific or tag specific antibody.

"Epitope tagging" is a technique in which a known epitope is fused to a polypeptide, such as a recombinant protein, for example by means of genetic engineering. An epitope tag can be used in combination with an antibody specific for this epitope tag for detecting polypeptides such as proteins of interest. To be useful as an epitope tag a peptide should provide a region for selective binding of a specific antibody, the tag region should be available for binding even if the tag is linked to or fused with a polypeptide and unspecific binding should be avoided as far as possible. The binding between the epitope tag and the corresponding antibody should be strong, reliable and selective. By choosing a suitable combination of an epitope tag and a corresponding antibody, the technique makes it possible to detect proteins for which no antibody is available. This is especially useful for the characterization of newly discovered proteins and proteins of low immunogenicity.

Also provided is a system comprising a pair of an epitope and an antibody, that can be used for a number of experimental applications, such as Western blot analysis, immunoprecipitation, immuno(histo)chemistry, immunofluorescence studies, protein-protein interaction studies, ELISA, and affinity purification.

Despite being derived from an endogenous protein, β-catenin, it has been surprisingly found that proteins fused with the tag, are specifically and reliably detected with a epitope specific antibody without significant influence from any interaction of the antibody with endogenous protein. Without being held to this theory it is contemplated that this is due to the endogenous β-catenin being part of a protein complex forming the so-called adherens junctions, and therefore not being available for an efficient interaction with the epitope specific antibody. Furthermore it has been found that the epitope specific antibody BC2-Nb has an increased affinity to the epitope tag (1.4 nM) compared to the affinity of the BC2-Nb to endogenous β-catenin (3.7 nM), suggesting that binding of the antibody to tagged polypeptides is favored to binding of the antibody to endogenous β-catenin.

Polypeptides, such as polypeptides or proteins of interest, which have been fused or are linked with or are connected with the epitope tag can be specifically and reliably detected using a tag-specific antibody, as for example described below in detail. Tagged polypeptides can also be specifically, efficiently and reliably purified by an immunoaffinity based capture assay.

Also provided herein is a construct comprising a polypeptide and at least one epitope peptide, as defined above, at the N-terminal or C-terminal end of the polypeptide. In the constructs provided herein, the epitope peptide can consist of or comprise any epitope peptide amino acid sequence set forth herein, for example, SEQ ID NO: 1. SEQ ID NO: 3, SEQ ID NO: 4, SEQ ID NO: 5 SEQ ID NO: 32, SEQ ID NO: 33 or SEQ ID NO: 34 as defined herein. Therefore, any polypeptide provided herein, including a polypeptide in a construct, can have at least one epitope peptide consisting of or comprising, SEQ ID NO: 1. SEQ ID NO: 3, SEQ ID NO: 4, SEQ ID NO: 5 SEQ ID NO: 32, SEQ ID NO: 33 or SEQ ID NO: 34, as defined herein, at the N-terminal or C-terminal of the polypeptide. The term "construct consisting of or comprising a polypeptide and at least one epitope peptide" refers to a non-naturally occurring polypeptide, which can also be called a "fusion protein". The polypeptide comprised in the construct can comprise at least a protein of interest and optionally a linking sequence; it can also comprise further functional sequences and/or further tags. The construct can have one or more epitope tags provided herein. If the construct includes more than one tag, those can be arranged tandem-like, can be consecutive, can be spaced or can be at opposite ends. The construct in addition can comprise further tags which can be at any useful position.

Also provided is a nucleic acid encoding the epitope peptide provided herein. The nucleic acid can be RNA, DNA, PNA, or LNA.

Nucleic acid constructs comprise a nucleic acid sequence encoding at least one epitope peptide provided herein. These nucleic acid constructs can be of prokaryotic or eukaryotic origin, such as of bacterial, mammalian, yeast, fungal, nematode, fish, avian, viral, or insect origin. Optionally, the nucleic acid construct also comprises the nucleic acid sequence of the polypeptide to be tagged, such as the protein of interest. The nucleic acid sequence encoding the epitope peptide can be downstream and/or upstream of the nucleic acid sequence encoding the polypeptide to be tagged resulting in a C-terminally and/or N-terminally tagged polypeptide. It has been surprisingly found, that the epitope peptide can be used C-terminally as well as N-terminally. This allows very versatile use of the epitope peptide or the nucleic acid coding it, respectively. The construct can comprise a nucleic acid coding for one epitope peptide or for more copies of the epitope peptide, such as two or three copies. The more than one copy can be adjacent to the terminal tag or tags can be at the N- and C-terminals respectively.

The construct can also be a nucleic acid expression construct, and comprises at least one nucleic acid encoding an epitope tag and at least one nucleic acid encoding a polypeptide to be tagged, wherein both can be positioned directly adjacent to each other, or can be separated by a linker sequence of an appropriate length, such as about 3-150 nucleobases. Other functional sequences can also be included. For example, the linker can comprise a recognition site for an endonuclease or a nucleic acid sequence that encodes a recognition site for a protease. Examples for proteases are TEV protease, thrombin, factor Xa protease, or a PreScission protease.

The nucleic acid construct or nucleic acid expression construct can further comprise nucleic acid sequences, which encode further tags, such as a HIS-tag.

The nucleic acid construct or nucleic acid expression construct can comprise a nucleic acid sequence, which encodes more than one tag, for example a tandem tag. A tandem tag is the combination of two tags in sequence. A tandem tag can comprise at least two copies of an epitope tag provided herein, or at least one epitope tag provided herein and at least one other tag. The construct can also comprise a number of same or different tags if appropriate.

Further provided is a host cell comprising a nucleic acid or nucleic acid expression construct provided herein. The "host cell" is a cell that comprises the nucleic acid sequences encoding the epitope tag provided herein. The host cell can be a stable transfectant or it can be transiently transfected with the nucleic acid construct comprising a nucleic acid sequence(s) encoding the epitope tag. The host cell can be a prokaryotic or a eukaryotic cell. For example the host cell can be a bacterial, yeast, insect, mammalian, plant, fungal, nematode, fish, or avian cell. The cell can be a primary cell or a cell line. The host cell can be an individual single cell, or can be a cell that is part of a tissue.

Also provided is a method for introducing the nucleic acid or the nucleic acid expression construct into a host cell. The introduction results in the nucleic acid encoding at least one epitope tag provided herein being connected to a nucleic acid encoding at least a polypeptide of interest in the host cell. Therefore, the host cell comprises the nucleic acid encoding at least one epitope tag provided herein and will, upon expression, comprise the epitope tag.

The method for introducing the nucleic acid into the host can be any method known in the art for this purpose, in particular the method can be selected from the group comprising CRISPR/Cas genome editing, genome editing methods using Zinc finger nucleases (ZFNs), transcription-activator like effector nucleases (TALENs), or meganucleases, reagent-based methods using reagents such as cationic lipids, calcium phosphate, or DEAE-dextran, transduction, transfection, and instrument-based methods such as electroporation, microinjection and laserfection.

Any of the epitope peptides provided herein can be used as an N-terminal or C-terminal epitope tag. Host cells that comprise the nucleic acid encoding the epitope tag will express a polypeptide, such as a polypeptide/protein of interest, which is linked with, or fused to the epitope tag. Depending on the sequence of the nucleic acid expression construct and/or on the method of introducing the nucleic acid encoding the epitope tag, the introduction into the host will result in an N-terminally or C-terminally tagged polypeptide. C-terminal or N-terminal tags are preferred compared to internal tags, as the terminal tags will be more easily accessible for interaction with a epitope specific antibody. The epitope peptide of the present invention can however also be used as an internal tag, provided that the tagged protein of interest exhibits a conformation, wherein the internal tag is accessible for interaction with a binding partner. For example, the protein of interest can exhibit loop structures, wherein the internal tag is part of the sequence forming the loop structure. In this case, the internal tag will be accessible for interaction with binding partners.

As used throughout, the term "affinity ligand" refers to molecules that are capable of binding with very high affinity to either a moiety specific for it or to an antibody raised against it. Examples include biotin (ligand)-streptavidin (moiety), digoxigenin (ligand)-anti-DIG-antibody and further tag specific antibodies. As used herein, the term "antibody" comprises monoclonal antibodies, polyclonal antibodies, particularly polyclonal monospecific antibodies (i.e. antibodies with different variable regions, which however all recognize the specific epitope tag provided herein), chimeric antibodies, as well as a fragment or variant of the above listed types of antibodies. The term "antibody" herein furthermore comprises genetically manipulated antibodies, and in a nonlimiting example, the term "antibody" refers to the heavy chain antibodies such as found in Camelidae, for example, in a camel or a llama. The binding elements of these antibodies consist of a single polypeptide domain, namely the variable region of the heavy chain polypeptide (VHH). These antibodies are naturally devoid of light-chains with the heavy chain variable domain forming the complete antigen-binding site. In contrast, conventional antibodies have binding elements comprising two polypeptide domains (the variable regions of the heavy chain (VH) and the light chain (VL)). The lack of dependence on interaction with a light chain variable domain for maintaining structural and functional integrity gives these VHH domains a substantial advantage over other small antibody fragments, in terms of ease of production and behavior in solution. In particular, VHH fragments are the preferred types of molecules for immuno-affinity purification, because of their unusual stability and their ability to refold efficiently after complete denaturation, which frequently occurs during elution of antigen. Heavy chain antibodies are also called single-domain antibodies or single-chain antibodies. Fragments of heavy chain antibodies are also termed "nanobodies". Fragments of antibodies are well-known in the art and any fragment that has epitope binding activity can be used as an "antibody" in the systems or for the interaction provided herein.

The term "antibody," as used herein, typically refers to full-length antibodies and to antibody fragments of the aforementioned antibodies as well as variants as defined below. Antibodies, that do not contain all the domains or regions of a full-length antibody, are fragments of antibodies which are also provided herein. Thus, the term "antibody" shall encompass any type of antibody, fragments and variants thereof, and mixtures of antibodies, fragments, and/or variants.

Any antibody that has affinity for and is specific for an epitope peptide provided herein and that provides for a high avidity or affinity can be used. It can be a conventional antibody or a heavy chain antibody, or a fragment of a conventional antibody or of a camelid antibody, it can also be a mixture of antibodies, fragments and/or variants. Preferred antibodies or antibody fragments are derived from heavy chain antibodies, such as camelid antibodies, and camelid antibody fragments, which are called nanobodies or Nb.

All of the afore mentioned antibodies may be present in bound or soluble form and may comprise a detectable moiety, or "label" (for example fluorescence markers, radioactive isotopes, colloidal gold marker, coupled enzymes, etc.), and/or may carry a peptide, group or linker for immobilization on a solid phase. The term "bound" refers to both membrane-bound antibodies and antibodies immobilized to a solid support or carrier material. The term "soluble" in the context of antibodies refers to antibodies that are not bound to a membrane or solid support, as is well understood by the skilled person.

Further provided is a construct comprising or consisting of a polypeptide and at least one epitope peptide at its N-terminal or C-terminal end as defined above and in the claims. The polypeptide can be any polypeptide as outlined above and can for example at least comprise a protein of interest and optionally further functional sequences, for example further tags. The construct can include one or more epitope tags, as explained above.

This construct or tagged polypeptide can be captured and/or detected by measuring the interaction of a tag specific affinity ligand, such as a tag specific antibody, which can comprise a detectable moiety and/or can be bound or bindable to a solid support, with the tagged polypeptide. The construct or tagged polypeptide of interest can be captured with the tag specific affinity ligand, such as the tag specific antibody for purification or enrichment, and the tagged polypeptide optionally can then be detected and/or quantified by known means, such as a secondary detection ligand, which preferably comprises a detectable moiety, such as a fluorescent label, and interacts with the polypeptide of interest, or, preferably, with the tag specific affinity ligand, such as the tag specific antibody For detection the tagged polypeptide and/or the tag specific affinity ligand, such as the specific antibody can comprise a detectable moiety or a moiety that allows introducing a detectable moiety or a moiety producing some kind of signal. Detectable moieties and methods for detecting and/or quantifying a moiety/signal are well-known in the art. It is also possible to enrich the polypeptide of interest and to later analyze binding partners, amount and other properties of interest of the tagged polypeptide.

Therefore, provided herein is a method for detection and/or capture, for example a method for purifying a polypeptide by capture and/or a method for detecting a polypeptide by capturing and/or measuring a detectable signal, or by enriching a polypeptide and analyzing the polypeptide in the obtained composition.

The detection methods provided herein are suitable to determine the presence, subcellular localization and/or amount of a polypeptide comprising the epitope peptide or epitope tag provided herein. The method can be an in vivo, or an in vitro method.

The tagged polypeptide or protein to be detected, located and/or quantified can be detected at its intracellular location in a host cell, for example in the cell nucleus, in cell membranes or another cell compartment. The tagged polypeptide or protein to be detected, and/or to be quantified can also be detected in a solution comprising the tagged polypeptide or protein, for example a cell lysate obtained from a host cell, or a tissue comprising the host cell.

In a first step of a detection method affinity ligand, such as an antibody specifically binding the epitope peptide is administered to a sample comprising the tagged polypeptide or protein. The sample can be a host cell, a tissue, a solution comprising cell lysate of a host cell or any other sample that comprises the tagged polypeptide, such as a supernatant, for example, obtained after centrifugation of a liquid comprising the host cell, wherein the host cell is capable of secreting the polypeptide of interest into the liquid or another specimen like a body fluid.

This administration step is carried out at conditions that allow specific interaction of the affinity ligand, such as the antibody and its epitope tag. Such conditions are well known to the person of skill in the art. Washing steps typically follow the administration of an antibody to its antigen, and the skilled person knows how and when to apply said washing steps.

In one example, the tagged polypeptide or protein is detected, quantified and/or located by detecting the interaction of the affinity ligand, such as the antibody and its epitope tag. The detection can be done as is known in the art. In another example, at least one or both interacting partners, usually the epitope specific affinity ligand, such as the antibody, comprises a detectable moiety.

Upon administration to the sample, such as a host cell or solution comprising cell lysate, or cell supernatant, the affinity ligand, such as an antibody, will specifically interact with the tagged protein. This interaction can be detected, monitored and quantified by measuring or observing the reporter signal obtained from the detectable moiety. For example, if the detectable moiety is a fluorescent label, fluorescence can be measured and observed upon excitation.

In another example, the detection method is carried out by using:

an epitope specific affinity ligand, such as an antibody, which does not comprise a detectable moiety;

at least one secondary binding partner, which can bind to the epitope specific affinity ligand, such as the antibody, the tagged protein, or to the complex built by both. The secondary binding partner can comprise a detectable moiety and/or can be immobilizable.

In a first step, an epitope specific affinity ligand, such as the antibody is administered to a sample, such as a host cell or a solution comprising a host cell lysate as disclosed above. In a second step, a secondary binding partner can be administered to the sample, such as the host cell or a solution comprising a host cell lysate comprising the tagged polypeptide or protein bound to the epitope specific affinity ligand, such as the antibody.

Presence, amount and/or localization of the tagged polypeptide or protein can be detected or determined by measuring or observing a reporter signal obtained from a detectable moiety comprised in the secondary binding partner.

The advantage of a two-step detection method using two types of binding partners is that the tag specific interaction is separated from the actual detection step. This allows the tag specific affinity ligand, such as the antibody, to remain unchanged, as it does not need to comprise a detectable moiety. This could enhance its specificity or affinity compared to a tag specific affinity ligand, such as an antibody, comprising a detectable moiety, as the detectable moiety could influence the interaction of the tag and its affinity ligand, such as an antibody. Thus, the reliability and efficiency of the detection method could be enhanced as well. Furthermore, using the tag specific affinity ligand, such as an antibody, simply as a capture affinity ligand, such as a capture antibody and not as a capture and detection affinity ligand, such as a capture and detection antibody allows separation of the capture and the detection steps if only presence and amount of the tagged protein or polypeptide is to be determined. Therefore, the first step using the epitope tag specific affinity ligand, such as a tag specific antibody could be followed by an isolation or enrichment step, yielding the captured tagged protein or polypeptide of interest. Isolation or purification steps are discussed further below. The detection step could then be carried out on the isolated and/or enriched tagged protein, leading to enhanced reliability of the obtained quantification and an easier handling of the detection step.

Suitable biophysical or biomolecular detection methods for qualitatively detecting the epitope tag/antibody interaction comprise any suitable method known in the art. Such methods include, without being limited thereto, methods as applied for qualitative or quantitative assays, e.g. for Enzyme-linked Immunosorbent Assay (ELISA), ELISPOT assay, Western Blot or immunoassays. Such methods comprise e.g. optical, radioactive or chromatographic methods, preferably when using any of the above labels, markers or linkers, more preferably fluorescence detection methods, radioactivity detection methods, Coomassie-Blue staining, silver staining or other protein staining methods, electron microscopy methods, methods for staining tissue sections by immunohistochemistry or by direct or indirect immunofluorescence, etc. Such methods may be applied either with the antibody or may involve the use of further tools, e.g. the use of a secondary binding partner, specifically binding to a part of the tagged polypeptide, the antibody, or the complex.

Depending on the size of the used antibody, the subcellular localization of the tagged polypeptide or protein of interest can also be determined. For example, if the detection antibody is small enough, distinct subcellular structures such as the intermediate filamentous network or an essential part of the replication machinery can be visualized and monitored.

For example, the detection antibody can be a nanobody, because nobodies can interact with proteins at subcellular localizations, such as structures deeply embedded in chromatin, due to their decreased size compared to conventional antibodies. Due to the absence of the variable light chain, nanobodies only possess three hypervariable loops (complementarity determining regions, CDRs) compared to six CDRs present in conventional antibodies. The three CDRs are flanked by 4 framework regions (FR). To compensate for the loss of CDRs, Nbs exhibit distinctive features regarding their CDR structure and antigen binding mode. In order to provide a sufficiently large antigen-interacting surface of 600-800 Å [1], most nanobodies exhibit substantially elongated CDR3 loops [2]. In some cases, the increased flexibility of such long loops is counteracted by fastening them to the Nb core with an additional disulfide bond [3].

A typical nanobody thus can be schematically displayed as an amino acid sequence comprising the following regions:

FR1-CDR1-FR2-CDR2-FR3-CDR3-FR4

An example of a nanobody provided herein is the BC2 nanobody (BC2-Nb) that shows favorable properties, such as very high affinity, strong binding, and versatility. The BC2-Nb comprises the variable region of a heavy chain antibody of *Camelidae* composed of framework region 1, CDR1, framework region 2, CDR2, framework region 3, CDR3, and framework region 4, as defined by the following amino acid sequence (122 aa):

(SEQ ID NO: 6; bold type designates the CDRs)
QVQLVESGGGLVQPGGSLTLSCTASGFTLDHYDIGWFRQAPGKEREGVSC

INNSDDDTYYADSVKGRFTIFMDNAKDTVYLQMNSLKPEDTAIYYCAEAR

GCKRGRYEYDFWGQGTQVTVSS

Table 1 provides the amino acid sequences of FR1, CDR1, FR2, CDR2, FR3, CDR3 and FR4 of the BC2 nanobody. A nucleic acid sequence encoding SEQ ID NO: 7, SEQ ID NO: 8, SEQ ID NO: 9, SEQ ID NO: 10, SEQ ID NO: 11, SEQ ID NO: 12 and/or SEQ ID NO: 13 is also provided herein.

In one example, the epitope specific antibody provided herein comprises the amino acid sequence defined in SEQ ID NO:6, or comprises an amino acid sequence that has at least about 90, 95, or 99% identity to SEQ ID NO:6. For example, the antibody can comprise an amino acid sequence that has at least about 90, 91, 92, 93, 94, 95, 96, 97, 98, 99% or any percentage identity in between these percentages. A nucleic acid encoding SEQ ID NO: 6 or an amino acid sequence that has at least about 90, 95, or 99% identity to SEQ ID NO:6 is also provided herein. The epitope specific antibodies provided herein exhibit a comparable affinity to the epitope peptide provided herein compared to the BC2-Nb defined by SEQ ID NO:6 and are termed "functional variants" of the BC2-Nb nanobody provided herein. In other words, provided herein are epitope specific antibodies that have the same epitope specificity as BC2-Nb. Also provided are antibodies having the same epitope specificity as an antibody having complementarity determining regions (CDRs) comprising amino acid sequences SEQ ID NO: 8, SEQ ID NO: 10 and/or SEQ ID NO: 12.

TABLE 1

Regions of amino acid sequence defining BC2-Nb:

| Region | Sequence | Position |
|---|---|---|
| FR1 | QVQLVESGGGLVQPGGSLTLSCTAS (SEQ ID NO: 7) | 1-25 |
| CDR1 | GFTLDHYD (SEQ ID NO: 8) | 26-33 |
| FR2 | IGWFRQAPGKEREGVSC (SEQ ID NO: 9) | 34-50 |
| CDR2 | INNSDDDTY (SEQ ID NO: 10) | 51-59 |
| FR3 | YADSVKGRFTIFMDNAKDTVYLQMNSLKPEDTAIYYCAE (SEQ ID NO: 11) | 60-98 |
| CDR3 | ARGCKRGRYEYDFW (SEQ ID NO: 12) | 99-112 |
| FR4 | GQGTQVTVSS (SEQ ID NO: 13) | 113-122 |

It has been found that mainly CDR3 is responsible for the strong binding of the epitope peptide provided herein. Another important part of the amino acid sequence of BC2-Nb is the cysteine (at position 50 of SEQ ID NO:6) present in FR2. This cysteine forms a disulfide bridge with the cysteine of CDR3 and is thus responsible for the binding competent folding of the CDR3. Therefore, any nanobody comprising as CDR3 the CDR3 sequence of BC2-Nb, and comprising a cysteine in the framework region 2 that is capable of forming a disulfide bridge with the cysteine of the CDR3, is suitable as one partner of the epitope tag/nanobody interaction. In a nonlimiting example, there are about 45 to 55, for example about 50 or 51 amino acid residues between the cysteine in the FR2 and the cysteine in CDR3. In the case of the BC2-Nb the cysteine of FR2 is at position 50, and the cysteine in CD3 is in position 102 (the position markers are referring to the position in SEQ ID NO:6 as shown above). Therefore there are 51 amino acid residues located between the cysteine in framework region 2 and the cysteine in CDR3.

Thus, the antibody BC2-Nb or a functional variant thereof comprising at least CDR3 of BC2-Nb and a cysteine in FR2 is an epitope specific antibody. The nanobody BC2-Nb or a functional variant thereof comprising at least CDR3 of BC2-Nb and a cysteine in FR2 is also an interaction partner with the epitope tag provided herein, in all of the disclosed methods of purification and/or detection as well as other uses disclosed in this application, as it has been shown that it is a very reliable and efficient binding partner of the epitope tagged polypeptides of interest. BC2-Nb and its functional variants can also be a component(s) of the kits disclosed in this application. Provided herein is also the use of the BC2-Nb or a functional variant thereof for detecting, quantifying, determining the subcellular localization of, or purifying a polypeptide comprising an epitope tag provided herein.

A functional variant of BC2-Nb is any antibody or fragment that has an affinity for the epitope tag provided herein that is at least 80%, more preferably at least 90% or at least 95% or even 99% or more than BC2-Nb. The affinity of a variant and of BC2-Nb can be measured as is known in the art and the results can be compared as is known to the skilled artisan and by well-known assays, for example by surface plasmon resonance (SPR), or by other protein-protein interaction monitoring assays.

Further provided is a purification method, or a capture and purification method. The purification method can be used in analytic, semi-preparative and preparative methods.

Thus, also provided is a method of purifying a polypeptide, such as a protein of interest comprising at least one epitope tag provided herein.

In this aspect the method comprises a capture step of contacting a sample, for example a solution, comprising a tagged polypeptide, with an affinity ligand, such as an antibody, capable of specifically binding to the epitope tag. The affinity ligand specifically binding to the epitope peptide can be an antibody, for example, the nanobody BC2-Nb or a variant thereof, as defined above.

The sample to be contacted with the epitope specific antibody can be any type of sample comprising a tagged polypeptide and can be processed to separate the polypeptide. Preferably the sample is a solution, for example a lysate of a host cell, comprising the tagged polypeptide, or a supernatant, such as a supernatant obtainable by centrifugation of a liquid comprising a host cell comprising the construct or tagged polypeptide, wherein the host cell is capable of secreting or otherwise transporting the tagged polypeptide into the liquid.

An antibody, a fragment or a variant used in a method for purifying a polypeptide, for example a protein of interest, can be used in solution or immobilized. To immobilize an affinity ligand such as an antibody against the epitope tag or a fragment or variant thereof, the affinity ligand, such as the antibody, fragment or variant, or a mixture thereof can be bound to a sample carrier, solid support, or matrix. This immobilization step can occur prior to or after the binding of the affinity ligand, such as an antibody, to the epitope tag. Methods for immobilizing affinity ligands, such as antibodies, and parts thereof are well-known to the skilled artisan and any method that allows immobilization without impairing binding properties can be used.

If the affinity ligand, for example, an antibody, capable of specifically binding to the epitope peptide provided herein is not immobilized to a solid support, then the method optionally can comprise a further step for isolating the complex, for example by using a binding partner for the complex, such as a secondary antibody that is specific for example for the complex or (in case the epitope specific antibody is an IgG antibody) for the constant part of the antibody. The secondary binding partner can be in solution or can be immobilized or immobilizable to a solid support.

The term "solid support" or "matrix" refers to any type of carrier material that can be used for immobilization of affinity ligands, for example, antibodies or parts thereof and it can refer to material in particulate (e. g. beads or granules, generally used in extraction columns) or in sheet form (e. g. membranes or filters, glass or plastic slides, microtitre assay plates, dipstick, capillary fill devices or such like) which can be flat, pleated, or hollow fibers or tubes. Suitable and well-known matrices without being exhaustive; are silica (porous amorphous silica), agarose or polyacrylamide supports, or macroporous polymers. Examples include dextran, collagen, polystyrene, polypropylene, polyvinylchloride, polyacrylamide, methacrylate, celluloses, calcium alginate, controlled pore glass, aluminum, titanium and porous ceramics, synthetic polymers and co-polymers, latex, silica, agarose, metal, glass, and carbon. Alternatively, the solid surface may comprise part of a mass dependent sensor, for example, a surface plasmon resonance detector. Conveniently, an array comprising a plurality of individual affinity ligands, for example, antibodies or antibody fragments, which are capable of specifically binding the epitope tag, bound or immobilized to a solid surface is provided. This array can be used to capture tagged polypeptides comprised in a solution as soon the solution is brought in contact with the immobilized affinity ligands, such antibodies or antibody fragments.

In a further step following the capture step, the solid support comprising the immobilized epitope specific antibody bound to the tagged polypeptide optionally is washed to remove unbound and unspecifically bound constituents.

In a further step, the tagged polypeptide can be optionally eluted to obtain the isolated polypeptide, such as the protein of interest. Elution of tagged protein bound to the immobilized antibody can be achieved by methods known in the art. For example, the tagged protein can be eluted by competitive elution with the isolated epitope peptide. This isolated epitope peptide will then be in competition with the tagged polypeptide to bind the immobilized epitope specific antibody. If the isolated polypeptide is added in surplus concentration, the reaction balance of the binding will be shifted to the binding of the immobilized antibody with the isolated epitope peptide. This results in the release of the tagged polypeptide. The released polypeptide can then optionally be purified further by method steps known to the skilled person.

The tagged polypeptide can also remain immobilized to the solid support, such as beads, and processed further in downstream application such as mass spectrometry, without the elution step.

In another example, a tagged protein, for example a tagged polypeptide that comprises a linker with a cleavage site, can be cleaved with an appropriate means, for example a protease to remove the tag, thereby the polypeptide is released from the immobilized antibody, and the polypeptide can be obtained in its native form. For this example, the nucleic acid sequence encoding the polypeptide should not only comprise a sequence encoding the epitope tag but also a sequence encoding a linker with a breakable site, for example a cleavage site recognized by a protease. The release step by enzymatic cleave can replace or follow the elution step.

Also provided is a kit comprising the components necessary to carry out the methods provided herein.

For example, a kit for capture and/or detection of tagged polypeptides is provided. The kit is suitable for carrying out a method of capture and/or detection. The kit comprises the following comprises:

a nucleic acid or a nucleic acid expression construct encoding an epitope peptide provided herein;

an affinity ligand, for example, and not to be limiting, an antibody capable of specifically binding to the epitope peptide optionally a detectable moiety; and buffers and reagents necessary for the capture and/or detection methods described herein.

The nucleic acid or the nucleic acid expression construct encoding the epitope peptide is to be introduced into a host cell as described above, and as is known to the skilled person. The kit can in this regard also comprise the buffers and reagents necessary to introduce the nucleic acid or the nucleic acid expression construct encoding the epitope peptide into a host cell.

The affinity ligand capable of specifically binding to an epitope peptide provided herein can be an antibody, for example, the nanobody BC2-Nb or a variant thereof as defined above.

The affinity ligand capable of specifically binding to the epitope peptide, for example, an antibody, can comprise at least one detectable moiety. The kit can also comprise at least one secondary binding partner, that can bind to a unit provided on the complex or one of its components, such as avidin or streptavidin if the complex or one of its components is biotinylated, or secondary and third antibodies for capturing the complex built from the tagged polypeptide and the affinity ligand, such as an antibody. These further antibodies are, for example, specific for other parts of the polypeptide or the epitope specific affinity ligand, such as an antibody, or for units provided on the polypeptide, the affinity ligand, such as an antibody, or the complex, such as the constant part of the primary affinity ligand or antibody capable of specifically binding to the epitope peptide. The further antibodies can also comprise a detectable moiety.

Affinity ligands, for example, antibodies, as defined herein are particularly useful for detecting, capturing, and/or purifying a polypeptide comprising an epitope peptide provided herein. Therefore, provided herein is the use of an epitope specific affinity ligand, such as an antibody, as defined herein, in particular a nanobody for detecting, capturing, and/or purifying a polypeptide comprising the epitope peptide described herein.

The kit can further comprise a solid support comprising the affinity ligand, such as an antibody, specifically binding to the epitope peptide immobilized or attached to the solid support.

The detectable moiety can be any detectable moiety as defined above. Preferably, the detectable moiety is a fluorescent label.

In another example, a kit for capture and purification of tagged polypeptides is provided.

The kit for purification of tagged polypeptides comprises the following components.

a nucleic acid or a nucleic acid expression construct encoding an epitope peptide provided herein;
  an affinity ligand, for example, an antibody capable of specifically binding to the epitope peptide;
  optionally a solid support; and
  buffers and reagents necessary for the capture and purification methods described herein.

The nucleic acid or the nucleic acid expression construct encoding the epitope peptide is introduced into a host cell as described above, and as is known to the skilled person. The kit can also comprise the buffers and reagents necessary to introduce the nucleic acid or the nucleic acid expression construct encoding the epitope peptide into a host cell.

The affinity ligand, for example, an antibody capable of specifically binding to the epitope peptide, can be the nanobody BC2-Nb or a variant thereof as defined above.

The affinity ligand, for example, an antibody capable of specifically binding to the epitope peptide, can be in solution or immobilized or attached to a solid support. The kit can also comprise further binding partners, as outlined above. The further binding partner can also comprise a detectable moiety.

The solid support can be any solid support as defined above, and a suitable way of immobilization or attachment of the affinity ligand, such as an antibody, to the solid support can be chosen by the skilled person.

The kit can also comprise reagents suitable to release the captured tagged polypeptide from the affinity ligand, such as an antibody, capable of specifically binding to the epitope peptide provided herein. Thus, the kit can, for example, comprise an isolated epitope peptide provided herein. It can also comprise an enzyme, which is capable of releasing the captured tagged polypeptide from the affinity ligand, such as an antibody capable of specifically binding to the epitope peptide by cleaving the tag from the polypeptide. For example, the enzyme can be a protease such as TEV protease, thrombin, factor Xa protease, or a PreScission protease.

Furthermore provided is also a complex of a construct comprising an epitope peptide and a protein of interest as defined above with an epitope specific antibody. Also provided is such a complex immobilised on a carrier or support like a bead or a column.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Provided below are the following examples which should not be interpreted as restricting the scope or spirit of the invention.

Example 1

Overview

By covalently coupling the monovalent BC2-Nb to solid matrices a BC2 nanotrap was generated. This serves as a highly efficient pulldown reagent similar to the previously described GFP nanotrap [4] which becomes widely used to purify GFP-tagged complexes from cellular lysates [5]. The excellent binding characteristics of the BC2 nanotrap are favorable for proteomic analysis applying e.g. highly competitive binding conditions using chaotropic agents (up to 4 M Urea or 1.5 M GdmCl) or denaturing detergents (2% SDS) in the binding reaction [6]. In contrast to the GFP nanotrap where bound proteins are released only under denaturing conditions, BC2 nanotrap-bound proteins can be eluted in a functional conformation simply by peptide competition using low amounts of BC2-peptide (0.1-1 mM). Positional cloning revealed that the N- or the C-terminally localized BC2-tag is equally well recognized by the BC2 nanotrap. For N-terminally tagged GFP an additional band in the non-bound fraction was observed. This indicates that the BC2-tag might be proteolytically removed upon cellular lysis, a phenomenon which has already been described for other epitope tags in mammalian expression systems [7].

The BC2-based capture and detection system described in this study is an attractive alternative to currently available epitope-tag systems. BC2-Nb binds BC2-epitope-tagged proteins with a $K_D$ of ~1.4 nM and therefore shows a ~10-100 fold higher affinity compared to the available FLAG, HA, c-myc or the nanobody-derived EPEA-systems [8-10].

Recently, nanobodies against β-catenin were generated recognizing different epitopes within the amino acid sequence of β-catenin. These antibodies were used to monitor endogenous β-catenin within cells [11]. One of these Nbs, referred to as BC2-Nb, recognizes a short linear epitope corresponding to aa 16-27 of β-catenin.

Here, a detailed structural and biochemical analysis of the BC2-Nb and its interactions with the peptide epitope, hereafter referred to as BC2-tag (BC2T), is provided. Data reveal an unusual binding mechanism mediated by the extended CDR3 and the framework of BC2-Nb, which is termed "headlock binding". Based on the high-affinity binding properties of BC2-Nb a novel BC2-tag purification and detection system was developed and characterized. It is shown that the immobilized BC2-Nb efficiently captures and purifies BC2-tagged proteins from bacterial and mammalian cell extracts in a natively folded state. By co-localization analysis, for the first time the detection of peptide-tagged cellular proteins using a fluorescently labeled nanobody could be shown. This versatile capture and detection system now enables a unique combination of biochemical and microscopic analyses of a large variety of proteins comprising this small, inert peptide-tag.

A nanobody was generated that binds a short linear peptide with very high affinity ($K_D$~1.4 nM). Structure analysis of the BC2-Nb/BC2-peptide complex revealed an unusual binding mode in which the BC2 peptide forms an additional antiparallel p-strand that inserts into a β-sheet structure formed by the CDR3 and the framework regions. Numerous backbone hydrogen bonds provide affinity, and a salt bridge between Arg106 of CDR3 and Glu44 of FR2 embraces the bound peptide in a headlock-like fashion. A comparison with all nanobody complexes available in the Protein Data Bank (PDB) shows that such a binding mode has not been previously observed in any of the 81 known crystallized complexes. Affinity measurements of headlock-mutated BC2-Nbs show ~10-fold reduced binding affinities and higher off-rates. These data clearly suggest that the main function of the headlock is in fastening the already-bound peptide to the nanobody.

Epitope analysis using positional scanning peptide libraries revealed a small set of four specificity-determining residues, with the most critical being W10. By contrast, the other residues do not contribute towards the binding specificity, mostly because they are not engaged in contacts. The reliance on many backbone interactions to generate affinity and only four amino acid side chains for specificity renders the BC2T/BC2-Nb system especially versatile. Most of the BC2T residues can be replaced without sacrificing binding efficiency, and this allows a straightforward adaptation of the tag for individual applications, including charge modifications, addition of tryptophan residues for increased absorbance at 280 nm, or introduction of a protease cleavage site or even an unusual amino acid for labeling purposes.

Finally, a study shows that the BC2-Nb offers new opportunities for cellular imaging. Basically, nanobodies can be easily modified by site-directed labelling with the full-range of available organic dyes and applied for direct imaging of cellular structures without the need of a secondary antibody for detection. Recently, it was demonstrated that GFP and RFP-specific nanobodies labeled with photoactivated localization microscopy (PALM)-compatible organic dyes such as AlexaFluor 647 (AF647) efficiently visualize fluorescent fusion proteins in high-resolution microscopy. There is still an ongoing demand for nanobodies that recognize a smaller epitope to minimize steric hindrances or potential linkage errors derived from large tags such as GFP or RFP. In this study it was demonstrated for the first time that a fluorescently labeled peptide-specific nanobody can be used for the visualization of distinct subcellular structures such as the intermediate filamentous network or an essential part of the replication machinery. Based on these findings it was proposed by the inventors that a BC2-mediated detection system provides unique advantages compared to currently available approaches. Firstly, due to its small size (12 aa, 1.4 kDa) the BC2-tag does not interfere with the subcellular localization or folding of ectopically expressed proteins. Secondly, the usage of a small nanobody (2×4 nm) directly links the detection signal to the corresponding antigen. Thirdly, the BC2 nanobody can be easily modified e.g. for site directed labeling with appropriate high resolution compatible dyes. In summary, nanobody-mediated labeling of BC2-tagged constructs now combine a minimal epitope tag with the high photon yield of organic dyes and minimal linkage error.

Example 2

Structural Basis of Epitope Binding

Since most of the described Nbs have conformational epitopes, the molecular mechanism underlying the observed high-affinity binding was investigated by solving high-resolution crystal structures of BC2-Nb alone (at a resolution of 1.8 Å) and in complex with BC2T (1.0 Å). From here on, BC2T amino acids will be referred to in one-letter code and BC2-Nb amino acids in three-letter code in order to facilitate the presentation and discussion of the results. The amino acid positions are referring to the positions of amino acid residues in the epitope tag consisting of 12 amino acids, as defined in SEQ ID NO:4 (PDRKAAVSHWQQ).

Figure 1:
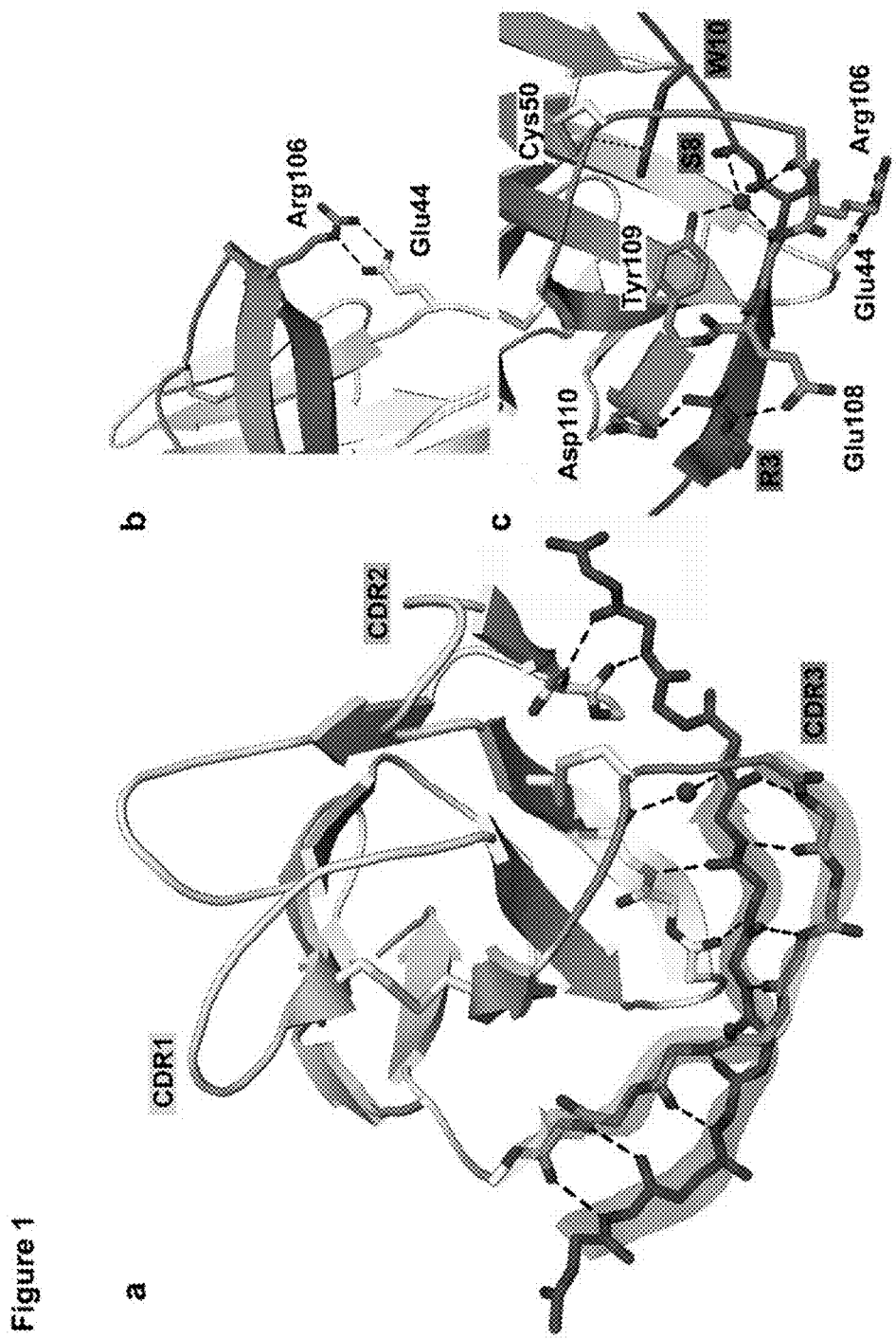
FIG. 1 shows the structural analysis of BC2-nanobody (BC2-Nb) and a BC2-Nb/BC2T complex.

The BC2-Nb adopts the typical immunoglobulin fold, which consists of nine β-strands forming two β-sheets connected by loops and by a conserved disulfide bond between Cys22 and Cys96 (FIG. 5 a). Similar to other nanobody structures, BC2-Nb features an especially long CDR3, which contains 14 amino acids and is stabilized by an additional disulfide bond formed between Cys102 (located in the CDR3) and Cys50 (located in the framework region 2 (FR2)) (FIG. 5 a). The BC2T binds to BC2-Nb in an elongated conformation, inserting into a groove between the CDR3 and the FR2 and FR3 of BC2-Nb. The peptide is integrated into the BC2-Nb structure, forming a strand in a β-sheet (FIG. 1 a). This results in a large number of backbone hydrogen bonds that anchor the peptide to neighboring secondary structure elements. Notably, neither CDR1 nor CDR2 are involved in the interaction with BC2T (FIG. 1 a, Table 2 below).

TABLE 2

|  | BC2-Nb | BC2-Nb-BC2T complex* |
|---|---|---|
| Data collection | | |
| Space group | $P2_12_12_1$ (19) | C2 (5) |
| Cell dimensions | | |
| a, b, c (Å) | 31.77, 47.74, 67.97 | 106.01, 31.53, 35.88 |
| α, β, γ (°) | 90, 90, 90 | 90, 107.54, 90 |
| Resolution (Å) | 39.07-1.80 (1.85-1.80) | 50.55-1.00 (1.03-1.00) |
| $R_{meas}$ (%) | 8.8 (94.6) | 6.4 (99.7) |
| I/σI | 13.06 (1.45) | 18.42 (2.05) |
| $CC_{1/2}$ (%) | 99.8 (52.0) | 100 (52.4) |
| Completeness (%) | 99.6 (99.6) | 99.6 (98.1) |
| Redundancy | 14.4 (3.6) | 9.5 (8.0) |
| Wilson B (Å$^2$) | 27.7 | 11.5 |
| Refinement | | |
| Resolution (Å) | 39.07-1.80 | 50.55-1.00 |
| No. reflections | 70062 | 580345 |
| $R_{work}/R_{free}$ (%) | 19.1/21.7 | 12.8/14.9 |
| No. atoms | | |
| BC2-Nb | 902 | 1037 |
| BC2T | — | 115 |
| Water | 36 | 134 |
| MPD | 8 | — |

TABLE 2-continued

|  | BC2-Nb | BC2-Nb-BC2T complex* |
|---|---|---|
| B-factors (Å$^2$)) | | |
| BC2-Nb | 27.8 | 11.2 |
| BC2T | — | 14.3 |
| Water | 32.6 | 24.3 |
| MPD | 38.6 | — |
| R.m.s. deviations | | |
| Bond lengths (Å) | 0.011 | 0.020 |
| Bond angles (°) | 1.107 | 1.452 |

The unbound and bound BC2-Nb structures are similar, and can be superimposed with a small overall root mean square deviation (RMSD) of the atomic positions 0.4 Å (Phenix structure_comparison). The CDR3 loops in particular have similar orientations, with the exception of two amino acids (Arg106 and Tyr107) that are flipped almost 180 degrees (FIG. 5 b). In the unliganded BC2-Nb, the β-carbon of Arg106 is oriented towards the core structure of the Nb, while the Arg106 side chain interacts with the backbone carbonyl group of Glu108 and with the π-electron system of Tyr109. The β-carbon of Tyr107 is pointing away from the Nb and the aromatic ring is involved in a cation-π interaction with Arg45. In the complex, residues Arg106 and Tyr107 are flipped, as their β-carbons and their side chains face into opposite directions. Arg106 is now involved in a charge-mediated interaction with the side chain of Glu44 located in FR2 (FIG. 1 b). This unusual interaction, which is termed "headlock" by the inventors, reaches over the bound peptide and locks it firmly in place. Several direct and water-mediated interactions fasten the peptide in its binding site (FIG. 1 c). However, only a small subset of BC2T residues is involved in these contacts: R3 forms a salt bridge with Asp110, S8 is engaged in a hydrogen bond with the carbonyl group of Lys103 and also complexes a water molecule together with Tyr109, and W10 is buried in a hydrophobic pocket where it forms both a CH-π interaction with Cys50 and a hydrogen bond with the carbonyl group of Cys102 (a complete overview of all interactions is shown FIG. 6).

The impact of point mutations on the binding properties of the BC2-Nb was investigated. First, the additional disulfide bond that connects CDR3 and FR2 was removed by replacing Cys50 with an alanine and Cys102 with a serine (BC2-Nb$_{C50A\_C102S}$). Binding studies using modified GFP that contains BC2T as a C-terminal peptide tag (GFP$_{BC2T}$) revealed that this mutation leads to complete loss of binding (data not shown). The most likely explanation for this result is that the disulfide bridge is required to maintain the structure of the CDR3, which contributes most of the contacts with BC2T. Next, the contribution of the "headlock" motif towards binding was analyzed. Arg106 was replaced with either a serine (BC2-Nb$_{R106S}$) or a glutamate (BC2-Nb$_{R106E}$) and surface plasmon resonance (SPR) measurements were performed using the GFP$_{BC2T}$ construct. Both mutant proteins yield K$_D$ values of ~11 nM which are about 10-fold lower compared to BC2-Nb (K$_D$: 1.4 nM) (Table 3 below, FIG. 7). Interestingly, the wt and mutant proteins showed similar on-rates, whereas significantly higher off-rates were observed in both mutants (Table 3). In summary, the modest changes in the affinities are consistent with the structural analysis. The thirteen backbone interactions of the extended peptide clearly contribute to the high affinity of the interaction. The "headlock" most likely helps to secure the bound peptide, as indicated by the lower dissociation rate of the wt protein.

TABLE 3

| Nbs | R$_{max}$ [RU] | K$_D$ [nM] | k$_{on}$ [M$^{-1}$s$^{-1}$] | k$_{off}$ [s$^{-1}$] | χ$^2$ |
|---|---|---|---|---|---|
| BC2-Nb | 170 ± 0.34 | 1.4 ± 0.06 | 4.6 ± 0.04 × 10$^5$ | 6.4 ± 0.27 × 10$^{-4}$ | 3.5 |
| BC2-Nb$_{R106E}$ | 160 ± 0.48 | 12.0 ± 0.15 | 2.8 ± 0.01 × 10$^5$ | 3.4 ± 0.04 × 10$^{-3}$ | 3.8 |
| BC2-Nb$_{R106S}$ | 160 ± 0.43 | 9.7 ± 0.13 | 3.3 ± 0.03 × 10$^5$ | 3.2 ± 0.03 × 10$^{-3}$ | 3.1 |

Example 3

Detailed Epitope Analysis Using Synthetic Positional Scanning Peptide Libraries

Although the high-affinity binding and kinetics can be explained by the observed structural features, the specificity of complex formation must lie elsewhere. As only a subset of BC2T residues are involved in specific, side-chain-mediated contacts with the Nb, the contributions of these individual amino acids for binding using positional scanning peptide libraries were examined. In total, 12 different BC2T libraries displaying all 20 proteinogenic amino acids in one single position of the peptide were used in immunoprecipitation experiments. The BC2T libraries were subjected to liquid chromatography followed by mass spectrometry analysis before and after immunoprecipitation with immobilized BC2-Nb, BC2-Nb$_{R106S}$ or BC2-Nb$_{R106E}$. By determining the peptides remaining in the non-bound fraction after pulldown, the composition of non-bound peptides and correspondingly, the invariable amino acid positions (Table 4, below) were mapped. Specifically precipitated peptides were identified by a comparative analysis of the peptides in the supernatant of BC2-Nb or mutants thereof and the supernatant of a non-BC2T-related control Nb (GFP-specific Nb). The direct comparison with the GFP-Nb made it possible to determine the quantitative degree of peptide capture without the need of labeled standards. Thus, if no peptide was captured by the BC2-Nb, the ratio given in FIG. 2 would be one or close to one. The more peptide was captured the more the value approximates 0. It was not possible to discriminate between isoleucine (I) and leucine (L) peptide versions since these peptides are isobaric. However, two peptide versions containing I/L could be resolved and thus two values are given as result.

The analysis shows that BC2T residues at positions 1, 2, 4, 5, 7, 9, 11, and 12 of SEQ ID NO:4 can be replaced without affecting the epitope binding properties (Table 4, below). These results are in agreement with the structure, which shows that the side chains of all eight residues face away from the Nb. However, the analysis of the supernatants of the R3, A6, S8 and W10 BC2T libraries revealed little cross-reactivities of the nanobodies to other amino acids at these positions (FIG. 2 *a-d*). Notably, bound peptides from the R3 BC2T library (BC2T$_{R3X}$) have either residues with basic properties, i.e. K3 or H3 or residues comprising smaller side chains, i.e. T3 or V3 (FIG. 2 *a*). This observation is in agreement with the crystal structure as the salt bridge between R3 and Asp110 could possibly also be formed by H3 or K3. The analysis of the BC2T$_{A6X}$ library revealed preferences of the BC2-Nb to small amino acids at position 6, as cysteine, valine, threonine and serine permutants were efficiently pulled down from the library. Peptides containing glycine, leucine or isoleucine at this position were pulled-down in smaller amounts (FIG. 2 *b*). These results are consistent with the crystal structure, where the A6 side chain is pointing towards a small hydrophobic pocket of the BC2-Nb. Binding of larger amino acids (i.e. leucine, isoleucine) would require conformational rearrangements, and a glycine would introduce additional flexibility. A similar effect was observed for the BC2 T$_{S8X}$-library. Alanine, cysteine, threonine and valine can replace S8, while other residues were captured to a minor degree (FIG. 2 *c*). The hydroxyl group of S8 forms a hydrogen bond with the carbonyl group of Lys103 of the nanobody. Cysteine and threonine could engage in somewhat similar, productive interactions, while the valine could at least be accommodated. The tryptophan at position 10 appears to be an invariable specificity-determining amino acid in our peptide scanning study, as none of the W10 permutants were captured by BC2-Nb (FIG. 2 *d*). This is in excellent agreement with the structural analysis, which shows that the W10 side chain inserts into a deep, hydrophobic pocket on the nanobody.

The results of the epitope scanning for the mutants BC2-Nb$_{R106S}$ and BC2-Nb$_{R106E}$ are almost identical with the BC2-Nb, with one notable exception. The analysis of BC2T$_{A6X}$ library revealed that in contrast to BC2-Nb the mutated Nbs precipitated to a small extent also BC2T variants that carried a lysine or arginine at position 6 (FIG. 2 *b*). This observation suggests that mutation of the headlock-forming Arg45 by Ser or Glu results in somewhat lower peptide specificity. In summary, four positions in BC2T with limited or no amino acid variability were identified. The results are in accordance with the structure, which shows that the side chains of R3, S8 and W10 are directly involved in BC2-Nb interactions while permutants of A6 are probably sterically disfavored and may prevent the formation of the headlock binding. Taken together, this analysis confirms that a small subset of side-chain interactions help determine the specificity of BC2-Nb for the BC2T sequence.

TABLE 4

| | P | | D | | R | | K | | A | | A | | V |
|---|---|---|---|---|---|---|---|---|---|---|---|---|---|
| | ratio | error | ratio | error | ratio | error | ratio | error | ratio | error | ratio | error | ratio |
| BC2-Nb (r: ratio; e: | | | | | | | | | | | | | |
| A | 0.1 | 0.0 | 0.2 | 0.0 | 0.7 | 0.0 | 0.2 | 0.0 | 0.2 | 0.0 | 0.1 | 0.0 | 0.4 |
| G | 0.4 | 0.0 | 0.3 | 0.0 | 0.9 | 0.1 | 0.6 | 0.0 | 0.3 | 0.1 | 0.7 | 0.1 | 0.7 |
| V | 0.2 | 0.0 | 0.1 | 0.0 | 0.3 | 0.0 | 0.1 | 0.0 | 0.1 | 0.0 | 0.3 | 0.0 | 0.1 |
| I/L1 | 0.4 | 0.1 | 0.1 | 0.0 | 0.5 | 0.0 | 0.1 | 0.0 | 0.1 | 0.0 | 0.7 | 0.0 | 0.1 |
| I/L2 | 0.3 | 0.1 | 0.2 | 0.0 | 0.5 | 0.0 | 0.2 | 0.0 | 0.1 | 0.0 | 0.9 | 0.0 | 0.2 |
| M | 0.2 | 0.0 | 0.1 | 0.0 | 0.7 | 0.0 | 0.1 | 0.0 | 0.1 | 0.0 | 1.0 | 0.1 | 0.3 |
| P | 0.1 | 0.0 | 0.6 | 0.1 | 0.8 | 0.1 | 1.0 | 0.1 | 0.1 | 0.0 | 1.1 | 0.1 | 1.0 |
| F | 0.2 | 0.0 | 0.2 | 0.0 | 0.8 | 0.1 | 0.3 | 0.0 | 0.1 | 0.0 | 1.0 | 0.1 | 0.2 |
| W | 0.1 | 0.0 | 0.2 | 0.0 | 0.8 | 0.1 | 0.3 | 0.0 | 0.0 | 0.0 | 1.1 | 0.1 | 0.1 |
| S | 0.3 | 0.0 | 0.1 | 0.0 | 0.6 | 0.0 | 0.3 | 0.0 | 0.1 | 0.0 | 0.5 | 0.0 | 0.3 |
| T | 0.5 | 0.1 | 0.1 | 0.0 | 0.3 | 0.0 | 0.2 | 0.0 | 0.1 | 0.0 | 0.2 | 0.0 | 0.2 |
| N | 0.6 | 0.1 | 0.2 | 0.0 | 0.7 | 0.0 | 0.5 | 0.0 | 0.3 | 0.1 | 1.0 | 0.0 | 0.2 |
| Q | 0.6 | 0.0 | 0.1 | 0.0 | 0.5 | 0.0 | 0.1 | 0.0 | 0.2 | 0.0 | 1.0 | 0.0 | 0.4 |
| Y | 0.1 | 0.0 | 0.1 | 0.0 | 0.7 | 0.1 | 0.2 | 0.0 | 0.1 | 0.0 | 1.0 | 0.0 | 0.1 |
| C(Abu) | 0.1 | 0.0 | 0.1 | 0.0 | 0.5 | 0.0 | 0.1 | 0.0 | 0.1 | 0.0 | 0.1 | 0.0 | 0.2 |
| K | 0.3 | 0.0 | 0.2 | 0.0 | 0.2 | 0.0 | 0.1 | 0.0 | 0.2 | 0.1 | 1.0 | 0.1 | 0.3 |
| R | 0.2 | 0.0 | 0.1 | 0.0 | 0.1 | 0.0 | 0.1 | 0.0 | 0.2 | 0.2 | 1.1 | 0.1 | 0.2 |
| H | 0.3 | 0.1 | 0.1 | 0.0 | 0.3 | 0.0 | 0.1 | 0.0 | 0.2 | 0.0 | 1.1 | 0.1 | 0.3 |
| D | 1.0 | 0.1 | 0.1 | 0.0 | 1.0 | 0.1 | 1.0 | 0.0 | 0.5 | 0.1 | 1.0 | 0.1 | 0.5 |
| E | 0.9 | 0.1 | 0.2 | 0.0 | 1.0 | 0.1 | 0.5 | 0.0 | 0.2 | 0.0 | 1.1 | 0.1 | 0.4 |
| $BC2\text{-}Nb_{(R106S)}$ (r: ratio; e: error) | | | | | | | | | | | | | |
| A | 0.3 | 0.0 | 0.4 | 0.1 | 0.9 | 0.1 | 0.6 | 0.0 | 0.4 | 0.0 | 0.2 | 0.0 | 0.7 |
| G | 0.6 | 0.1 | 0.5 | 0.1 | 1.0 | 0.1 | 0.9 | 0.1 | 0.5 | 0.0 | 0.9 | 0.1 | 0.8 |
| V | 0.4 | 0.0 | 0.2 | 0.0 | 0.7 | 0.1 | 0.2 | 0.0 | 0.2 | 0.0 | 0.6 | 0.0 | 0.3 |
| I/L1 | 0.7 | 0.1 | 0.2 | 0.0 | 0.9 | 0.1 | 0.4 | 0.1 | 0.2 | 0.0 | 0.8 | 0.1 | 0.3 |
| I/L2 | 0.6 | 0.4 | 0.3 | 0.0 | 0.9 | 0.1 | 0.6 | 0.1 | 0.2 | 0.0 | 0.9 | 0.1 | 0.4 |
| M | 0.5 | 0.1 | 0.2 | 0.0 | 0.9 | 0.1 | 0.5 | 0.0 | 0.2 | 0.0 | 0.9 | 0.1 | 0.5 |
| P | 0.2 | 0.0 | 0.8 | 0.1 | 1.0 | 0.1 | 1.0 | 0.1 | 0.4 | 0.0 | 1.0 | 0.1 | 1.0 |
| F | 0.3 | 0.1 | 0.3 | 0.1 | 1.0 | 0.1 | 0.7 | 0.1 | 0.2 | 0.0 | 0.9 | 0.1 | 0.4 |
| W | 0.3 | 0.0 | 0.3 | 0.1 | 1.0 | 0.1 | 0.8 | 0.1 | 0.1 | 0.0 | 1.0 | 0.1 | 0.3 |
| S | 0.6 | 0.1 | 0.3 | 0.1 | 0.9 | 0.1 | 0.7 | 0.0 | 0.4 | 0.0 | 0.8 | 0.0 | 0.4 |
| T | 0.7 | 0.1 | 0.2 | 0.1 | 0.8 | 0.1 | 0.7 | 0.0 | 0.3 | 0.0 | 0.4 | 0.1 | 0.3 |
| N | 0.7 | 0.1 | 0.3 | 0.1 | 1.0 | 0.0 | 0.9 | 0.1 | 0.5 | 0.0 | 1.0 | 0.1 | 0.4 |
| Q | 0.7 | 0.1 | 0.2 | 0.0 | 0.9 | 0.1 | 0.4 | 0.0 | 0.3 | 0.0 | 0.9 | 0.1 | 0.5 |
| Y | 0.3 | 0.0 | 0.2 | 0.0 | 1.0 | 0.1 | 0.5 | 0.0 | 0.2 | 0.0 | 0.9 | 0.1 | 0.3 |
| C* | 0.3 | 0.0 | 0.3 | 0.1 | 0.9 | 0.2 | 0.3 | 0.0 | 0.3 | 0.0 | 0.3 | 0.0 | 0.5 |
| K | 0.5 | 0.1 | 0.2 | 0.1 | 0.5 | 0.1 | 0.2 | 0.0 | 0.2 | 0.0 | 0.8 | 0.1 | 0.3 |
| R | 0.4 | 0.1 | 0.2 | 0.0 | 0.2 | 0.1 | 0.1 | 0.0 | 0.1 | 0.0 | 0.7 | 0.1 | 0.2 |
| H | 0.6 | 0.1 | 0.2 | 0.0 | 0.7 | 0.1 | 0.3 | 0.0 | 0.3 | 0.0 | 0.9 | 0.1 | 0.4 |
| D | 0.8 | 0.1 | 0.3 | 0.1 | 1.0 | 0.0 | 1.0 | 0.0 | 0.9 | 0.1 | 1.0 | 0.1 | 0.9 |
| E | 0.8 | 0.1 | 0.4 | 0.1 | 1.0 | 0.0 | 0.9 | 0.0 | 0.7 | 0.0 | 1.0 | 0.1 | 0.8 |

TABLE 4-continued

| | V error | S ratio | S error | H ratio | H error | W ratio | W error | Q ratio | Q error | Q ratio | Q error |
|---|---|---|---|---|---|---|---|---|---|---|---|
| BC2-Nb$_{(R106E)}$ (r: ratio; e: error) | | | | | | | | | | | |
| A | 0.2 | 0.0 | 0.2 | 0.1 | 1.0 | 0.1 | 0.4 | 0.1 | 0.2 | 0.1 | 0.1 | 0.0 | 0.5 |
| G | 0.5 | 0.0 | 0.4 | 0.1 | 1.0 | 0.1 | 0.9 | 0.1 | 0.4 | 0.1 | 0.8 | 0.1 | 0.7 |
| V | 0.3 | 0.0 | 0.1 | 0.0 | 0.5 | 0.0 | 0.1 | 0.0 | 0.1 | 0.0 | 0.3 | 0.0 | 0.2 |
| I/L1 | 0.6 | 0.1 | 0.1 | 0.0 | 0.9 | 0.2 | 0.3 | 0.1 | 0.1 | 0.0 | 0.7 | 0.1 | 0.1 |
| I/L2 | 0.5 | 0.2 | 0.2 | 0.1 | 0.9 | 0.2 | 0.5 | 0.0 | 0.1 | 0.0 | 0.8 | 0.1 | 0.2 |
| M | 0.4 | 0.1 | 0.1 | 0.0 | 0.9 | 0.1 | 0.3 | 0.1 | 0.1 | 0.0 | 1.0 | 0.1 | 0.3 |
| P | 0.1 | 0.0 | 0.8 | 0.1 | 1.0 | 0.1 | 1.0 | 0.1 | 0.2 | 0.0 | 1.1 | 0.1 | 0.9 |
| F | 0.3 | 0.0 | 0.2 | 0.0 | 1.0 | 0.1 | 0.6 | 0.1 | 0.1 | 0.0 | 1.0 | 0.1 | 0.2 |
| W | 0.2 | 0.0 | 0.1 | 0.0 | 1.1 | 0.2 | 0.7 | 0.1 | 0.0 | 0.0 | 1.0 | 0.1 | 0.2 |
| S | 0.4 | 0.0 | 0.2 | 0.0 | 0.8 | 0.1 | 0.6 | 0.1 | 0.2 | 0.0 | 0.6 | 0.0 | 0.3 |
| T | 0.6 | 0.1 | 0.1 | 0.0 | 0.6 | 0.0 | 0.5 | 0.1 | 0.1 | 0.0 | 0.3 | 0.0 | 0.2 |
| N | 0.7 | 0.1 | 0.2 | 0.1 | 0.9 | 0.0 | 0.8 | 0.1 | 0.3 | 0.1 | 1.0 | 0.1 | 0.4 |
| Q | 0.6 | 0.1 | 0.1 | 0.0 | 0.8 | 0.0 | 0.2 | 0.0 | 0.2 | 0.0 | 1.0 | 0.1 | 0.4 |
| Y | 0.2 | 0.0 | 0.1 | 0.0 | 0.9 | 0.1 | 0.3 | 0.1 | 0.1 | 0.0 | 1.0 | 0.1 | 0.2 |
| C* | 0.2 | 0.0 | 0.2 | 0.1 | 0.9 | 0.1 | 0.2 | 0.0 | 0.1 | 0.0 | 0.1 | 0.0 | 0.3 |
| K | 0.3 | 0.1 | 0.1 | 0.0 | 0.3 | 0.0 | 0.1 | 0.0 | 0.0 | 0.0 | 0.9 | 0.1 | 0.1 |
| R | 0.2 | 0.1 | 0.1 | 0.0 | 0.1 | 0.0 | 0.1 | 0.0 | 0.0 | 0.0 | 0.7 | 0.3 | 0.1 |
| H | 0.4 | 0.0 | 0.1 | 0.0 | 0.5 | 0.0 | 0.2 | 0.0 | 0.2 | 0.0 | 1.0 | 0.1 | 0.3 |
| D | 0.8 | 0.1 | 0.2 | 0.1 | 1.0 | 0.0 | 1.0 | 0.1 | 0.9 | 0.0 | 1.0 | 0.1 | 0.9 |
| E | 0.8 | 0.1 | 0.2 | 0.1 | 1.0 | 0.0 | 0.9 | 0.1 | 0.8 | 0.0 | 1.1 | 0.1 | 0.9 |

| | V | | S | | H | | W | | Q | | Q | |
|---|---|---|---|---|---|---|---|---|---|---|---|---|
| | ratio | error | ratio | error | ratio | error | ratio | error | ratio | error | ratio | error |
| BC2-Nb (r: ratio; e: error) | | | | | | | | | | | | |
| A | 0.0 | 0.0 | 0.0 | 0.0 | 0.2 | 0.0 | 1.0 | 0.1 | 0.1 | 0.1 | 0.1 | 0.0 |
| G | 0.1 | 0.0 | 0.5 | 0.2 | 0.4 | 0.0 | 1.2 | 0.2 | 0.1 | 0.1 | 0.2 | 0.0 |
| V | 0.0 | 0.0 | 0.1 | 0.0 | 0.2 | 0.0 | 1.0 | 0.1 | 0.1 | 0.0 | 0.1 | 0.0 |
| I/L1 | 0.0 | 0.0 | 0.4 | 0.1 | 0.3 | 0.0 | 1.0 | 0.1 | 0.1 | 0.0 | 0.1 | 0.0 |
| I/L2 | 0.0 | 0.0 | 0.7 | 0.2 | 0.1 | 0.0 | 1.0 | 0.0 | 0.1 | 0.0 | 0.1 | 0.0 |
| M | 0.0 | 0.0 | 0.6 | 0.2 | 0.1 | 0.0 | 1.0 | 0.1 | 0.1 | 0.0 | 0.1 | 0.0 |
| P | 0.1 | 0.0 | 0.7 | 0.2 | 0.8 | 0.1 | 1.1 | 0.1 | 0.6 | 0.4 | 0.1 | 0.0 |
| F | 0.0 | 0.0 | 0.7 | 0.2 | 0.1 | 0.0 | 0.9 | 0.0 | 0.0 | 0.0 | 0.2 | 0.0 |
| W | 0.0 | 0.0 | 0.6 | 0.3 | 0.1 | 0.0 | 0.1 | 0.0 | 0.0 | 0.0 | 0.1 | 0.0 |
| S | 0.0 | 0.0 | 0.1 | 0.0 | 0.2 | 0.0 | 1.1 | 0.2 | 0.1 | 0.0 | 0.1 | 0.0 |
| T | 0.0 | 0.0 | 0.1 | 0.0 | 0.2 | 0.0 | 1.0 | 0.1 | 0.1 | 0.0 | 0.1 | 0.0 |
| N | 0.0 | 0.0 | 0.2 | 0.1 | 0.1 | 0.0 | 1.0 | 0.1 | 0.1 | 0.1 | 0.1 | 0.0 |
| Q | 0.0 | 0.0 | 0.7 | 0.2 | 0.2 | 0.0 | 1.1 | 0.1 | 0.1 | 0.1 | 0.1 | 0.0 |
| Y | 0.0 | 0.0 | 0.6 | 0.2 | 0.1 | 0.0 | 1.0 | 0.1 | 0.0 | 0.0 | 0.1 | 0.0 |
| C(Abu) | 0.0 | 0.0 | 0.0 | 0.0 | 0.2 | 0.0 | 1.0 | 0.0 | 0.1 | 0.1 | 0.1 | 0.0 |
| K | 0.0 | 0.0 | 0.8 | 0.2 | 0.2 | 0.0 | 1.0 | 0.1 | 0.0 | 0.0 | 0.0 | 0.0 |
| R | 0.0 | 0.0 | 0.5 | 0.3 | 0.1 | 0.0 | 1.0 | 0.1 | 0.0 | 0.0 | 0.1 | 0.0 |
| H | 0.0 | 0.0 | 0.7 | 0.2 | 0.1 | 0.0 | 1.0 | 0.1 | 0.1 | 0.0 | 0.1 | 0.0 |
| D | 0.0 | 0.0 | 0.8 | 0.2 | 0.1 | 0.0 | 1.0 | 0.1 | 0.2 | 0.1 | 0.6 | 0.1 |
| E | 0.0 | 0.0 | 0.7 | 0.2 | 0.2 | 0.0 | 1.1 | 0.2 | 0.1 | 0.1 | 0.4 | 0.1 |
| BC2-Nb$_{(R106S)}$ (r: ratio; e: error) | | | | | | | | | | | | |
| A | 0.0 | 0.1 | 0.0 | 0.5 | 0.0 | 1.0 | 0.1 | 0.4 | 0.1 | 0.3 | 0.1 | |
| G | 0.0 | 0.9 | 0.1 | 0.8 | 0.0 | 1.1 | 0.2 | 0.5 | 0.0 | 0.4 | 0.1 | |
| V | 0.0 | 0.3 | 0.0 | 0.6 | 0.0 | 1.0 | 0.1 | 0.2 | 0.0 | 0.2 | 0.1 | |
| I/L1 | 0.0 | 0.6 | 0.0 | 0.5 | 0.0 | 1.1 | 0.1 | 0.2 | 0.0 | 0.2 | 0.1 | |
| I/L2 | 0.0 | 0.9 | 0.1 | 0.3 | 0.0 | 1.1 | 0.1 | 0.4 | 0.0 | 0.2 | 0.1 | |
| M | 0.1 | 1.0 | 0.1 | 0.3 | 0.0 | 1.1 | 0.1 | 0.3 | 0.0 | 0.3 | 0.1 | |
| P | 0.1 | 1.0 | 0.1 | 1.0 | 0.0 | 1.1 | 0.1 | 0.9 | 0.1 | 0.2 | 0.1 | |
| F | 0.0 | 0.9 | 0.1 | 0.3 | 0.0 | 1.1 | 0.1 | 0.2 | 0.0 | 0.4 | 0.1 | |
| W | 0.0 | 0.9 | 0.1 | 0.1 | 0.0 | 0.1 | 0.0 | 0.1 | 0.0 | 0.3 | 0.1 | |
| S | 0.0 | 0.2 | 0.0 | 0.5 | 0.0 | 1.1 | 0.2 | 0.2 | 0.0 | 0.2 | 0.1 | |
| T | 0.0 | 0.2 | 0.0 | 0.5 | 0.0 | 1.0 | 0.0 | 0.2 | 0.0 | 0.3 | 0.1 | |
| N | 0.0 | 0.7 | 0.1 | 0.3 | 0.0 | 1.1 | 0.1 | 0.3 | 0.0 | 0.2 | 0.1 | |
| Q | 0.0 | 0.9 | 0.1 | 0.4 | 0.0 | 1.1 | 0.2 | 0.3 | 0.0 | 0.3 | 0.1 | |
| Y | 0.0 | 0.9 | 0.1 | 0.2 | 0.0 | 1.0 | 0.0 | 0.1 | 0.0 | 0.3 | 0.1 | |
| C* | 0.1 | 0.1 | 0.0 | 0.5 | 0.0 | 1.0 | 0.1 | 0.3 | 0.0 | 0.2 | 0.1 | |
| K | 0.0 | 0.9 | 0.1 | 0.3 | 0.0 | 1.1 | 0.1 | 0.1 | 0.0 | 0.1 | 0.0 | |
| R | 0.0 | 0.9 | 0.1 | 0.2 | 0.0 | 1.1 | 0.2 | 0.1 | 0.0 | 0.1 | 0.0 | |
| H | 0.0 | 0.9 | 0.1 | 0.3 | 0.0 | 1.1 | 0.1 | 0.2 | 0.0 | 0.3 | 0.1 | |
| D | 0.1 | 0.9 | 0.1 | 0.5 | 0.0 | 1.0 | 0.1 | 0.6 | 0.0 | 0.9 | 0.1 | |
| E | 0.0 | 1.0 | 0.1 | 0.6 | 0.1 | 1.1 | 0.1 | 0.5 | 0.0 | 0.7 | 0.1 | |
| BC2-Nb$_{(R106E)}$ (r: ratio; e: error) | | | | | | | | | | | | |
| A | 0.0 | 0.1 | 0.0 | 0.3 | 0.0 | 1.1 | 0.1 | 0.3 | 0.1 | 0.1 | 0.0 | |
| G | 0.0 | 0.8 | 0.1 | 0.7 | 0.0 | 1.2 | 0.2 | 0.4 | 0.1 | 0.2 | 0.0 | |
| V | 0.0 | 0.2 | 0.0 | 0.5 | 0.0 | 1.0 | 0.1 | 0.2 | 0.1 | 0.1 | 0.0 | |
| I/L1 | 0.0 | 0.5 | 0.0 | 0.4 | 0.0 | 1.0 | 0.1 | 0.2 | 0.1 | 0.1 | 0.0 | |
| I/L2 | 0.0 | 0.9 | 0.1 | 0.2 | 0.0 | 1.0 | 0.0 | 0.4 | 0.2 | 0.1 | 0.0 | |
| M | 0.0 | 1.0 | 0.1 | 0.2 | 0.0 | 1.1 | 0.1 | 0.2 | 0.1 | 0.2 | 0.0 | |
| P | 0.0 | 1.0 | 0.1 | 0.9 | 0.1 | 1.1 | 0.1 | 0.9 | 0.1 | 0.1 | 0.0 | |

TABLE 4-continued

| | | | | | | | | | | | |
|---|---|---|---|---|---|---|---|---|---|---|---|
| F | 0.0 | 0.9 | 0.1 | 0.2 | 0.0 | 1.0 | 0.1 | 0.1 | 0.1 | 0.3 | 0.1 |
| W | 0.0 | 0.9 | 0.1 | 0.1 | 0.0 | 0.1 | 0.0 | 0.1 | 0.0 | 0.2 | 0.0 |
| S | 0.0 | 0.1 | 0.0 | 0.4 | 0.0 | 1.2 | 0.2 | 0.2 | 0.1 | 0.1 | 0.0 |
| T | 0.0 | 0.1 | 0.0 | 0.4 | 0.0 | 1.1 | 0.1 | 0.2 | 0.1 | 0.1 | 0.0 |
| N | 0.0 | 0.5 | 0.1 | 0.2 | 0.0 | 1.2 | 0.1 | 0.2 | 0.1 | 0.1 | 0.0 |
| Q | 0.0 | 0.9 | 0.1 | 0.3 | 0.0 | 1.2 | 0.2 | 0.3 | 0.1 | 0.1 | 0.0 |
| Y | 0.0 | 0.9 | 0.1 | 0.1 | 0.0 | 1.0 | 0.0 | 0.1 | 0.0 | 0.2 | 0.0 |
| C* | 0.0 | 0.1 | 0.0 | 0.3 | 0.0 | 1.1 | 0.1 | 0.2 | 0.1 | 0.1 | 0.0 |
| K | 0.0 | 0.9 | 0.1 | 0.2 | 0.0 | 1.3 | 0.1 | 0.1 | 0.1 | 0.0 | 0.0 |
| R | 0.0 | 0.9 | 0.1 | 0.1 | 0.0 | 1.3 | 0.2 | 0.1 | 0.0 | 0.0 | 0.0 |
| H | 0.0 | 0.9 | 0.1 | 0.2 | 0.0 | 1.2 | 0.2 | 0.2 | 0.1 | 0.1 | 0.0 |
| D | 0.0 | 1.0 | 0.1 | 0.4 | 0.0 | 1.1 | 0.1 | 0.5 | 0.1 | 0.8 | 0.1 |
| E | 0.0 | 0.9 | 0.1 | 0.5 | 0.0 | 1.2 | 0.1 | 0.4 | 0.1 | 0.6 | 0.0 |

Example 4

Generation of a BC2T-based Capture System

Based on the unusual ligand binding mode of the BC2-Nb it was aimed to develop a BC2T-based affinity system. Purified BC2-Nb were covalently coupled to Sepharose beads and an affinity matrix was generated that is referred to as "BC2 nanotrap". First, the ability of the BC2 nanotrap to precipitate BC2T-tagged proteins directly from crude lysate was tested. Therefore, the soluble protein fractions of *E. coli* cells expressing either C-terminally tagged GFP (GFP$_{BC2T}$) or wtGFP (control) were incubated with the BC2 nanotrap and the input, non-bound and bound fractions were analyzed by SDS-PAGE followed by coomassie staining and immunoblotting (FIG. 3 *a*). The obtained data shows that the BC2 nanotrap quantitatively precipitates GFP$_{BC2T}$. Next, BC2T purification was performed in the presence of various non-denaturing detergents (NP-40, Triton X100, CHAPS or Tween 20, 0.1-1% w/v) or increasing salt concentrations (0-500 mM NaCl, 2-50 mM KCl, 2-20 mM MgCl$_2$). None of these reagents appeared to have an impact on binding efficiency (data not shown). Additionally, antigen binding was tested under denaturing conditions by raising the concentrations of sodium dodecyl sulfate (SDS) or chaotropic agents (GdmCl; Urea) in the binding buffer. It was observed that the BC2 nanotrap efficiently precipitates its antigen in the presence of 2% SDS, 4 M Urea or up to 1.5 M GdmCl (FIG. 3 *b*). This indicates that the BC2 nanotrap remains functionally active under harsh conditions.

Although in some cases such harsh binding and elution conditions might be favorable to obtain highly pure protein, most of the bound protein is presumably denatured and does not maintain biological activity. Hence, more gentle elution conditions were tested using MgCl$_2$ (0.5 M-4 M), sodium thiocyanate (NaSCN, 1-3 M) or pH-mediated release (acidic; pH 1-2.5 or alkaline; pH 10-12). Liberation of bound GFP$_{BC2T}$ was also tested by competitive elution adding increasing concentrations of BC2 peptide (PDR-KAAVSHWQQ (SEQ ID NO: 4), 0.01-1 mM). Incubation with MgCl$_2$ does not elute GFP$_{BC2T}$ (data not shown), whereas treatment with high concentrations of NaSCN or acidic elution (pH 1.5) resulted in the release of 30%-40% of bound protein (FIG. 3*c*, upper panels). In contrast, alkaline elution using higher pH (pH 11 and 12) revealed a more efficient release of 40-80%. Notably, competitive elution was highly efficient as ~60% and ~80% of GFP$_{BC2T}$ was detected in elution fractions after addition of 0.1 mM and 1 mM BC2 peptide, respectively (FIG. 3*c*, lower panel). Moreover, whereas the fluorescence of GFP was drastically affected upon treatment with NaSCN or acidic pH, alkaline pH or peptide elution yielded fully fluorescent GFP (FIG. 8).

These results show that the BC2 peptide can efficiently displace BC2-bound proteins in their natively folded state.

The BC2-capture system was further analyzed for one-step purification of recombinant proteins derived from human cells. Specifically, it was investigated whether the terminal position of the BC2-tag has an impact on binding. To this end, a modified GFP comprising the BC2-tag either on the N- ($_{BC2T}$eGFP) or the C-terminus (eGFP$_{BC2T}$) was expressed in human embryonic kidney (HEK) 293T cells using untagged eGFP as a negative control. Two days after transfection soluble protein fractions were generated and subjected to immunoprecipitation using the BC2 nanotrap. Input, non-bound and bound fractions were analyzed by SDS-PAGE followed by Coomassie staining and immunoblotting (FIG. 3 *d*). The results show that both N- and C-terminally BC2-tagged GFP constructs were efficiently precipitated by the BC2 nanotrap whereas no GFP was detected in the negative control. A slightly smaller GFP fragment appeared in the non-bound fraction of $_{BC2T}$eGFP. Since this band does not appear in the bound lane it is hypothesized that it appears due to protease-mediated removal of the N-terminal BC2-tag during the cellular lysis procedure.

Next, it was tested whether the BC2 nanotrap can precipitate BC2-tagged cellular components of the intermediate filaments or the nuclear replication machinery. BC2T was genetically fused either to mCherry-vimentin (mCherry-VIM$_{BC2T}$) or eGFP-PCNA (eGFP-PCNA$_{BC2T}$) and both constructs were expressed in HEK293T cells. As controls, corresponding constructs without the BC2-tag were used. Soluble protein extracts were incubated with the BC2 nanotrap and whole lysate (input), non-bound and bound fractions were analyzed by immunoblotting using anti-vimentin or anti-PCNA antibodies. The results show that both mCherry-VIM$_{BC2T}$ and eGFP-PCNA$_{BC2T}$ were efficiently precipitated with the BC2 nanotrap, while no signal was detectable in the bound fractions of the untagged proteins (FIG. 9 *a*). The next question was whether the BC2-Nb can also detect BC2-tagged proteins in immunoblotting. Hence, fluorescently labeled BC2-Nb were generated by chemically coupling the purified nanobody to the organic dye Alex-aFluor488 (BC2-Nb$_{AF488}$) and it was used to probe immunoblots with soluble protein fractions of cells expressing eGFP-PCNA, eGFP-PCNA$_{BC2T}$, mCherry-VIM or mCherry-VIM$_{BC2T}$. The results show that BC2-Nb$_{AF488}$ is highly specific for BC2-tagged proteins, whereas untagged proteins were not detected (FIG. 9 *b*). Finally, it was asked whether the BC2-Nb also recognizes endogenous β-catenin in the presence of BC2-tagged proteins. While no signal for β-catenin was detected in Western blot with the BC2-Nb$_{AF488}$ (FIG. 9 *b*) minor amounts of β-catenin compared to the overexpressed BC2-tagged proteins were found in the bound fractions after precipitation with the BC2 nanotrap (FIG. 9 c).

In summary, the results show that the BC2T/BC2-Nb affinity system enables a robust and convenient one-step purification of BC2 tagged recombinant proteins from different expression systems under both native (i.e. non-denaturing) and denaturing conditions. In combination with the observed functionality in immunoblot detection, the system covers the full range of capture and detection of BC2-tagged proteins for a large range of biochemical analyses.

Example 5

Immunocytochemistry Using Fluorescently Labeled BC2-Nb

Numerous nanobodies have been described for molecular imaging of disease-relevant antigens located on cellular surfaces [12-14]. There are very few studies so far which have used nanobodies for cellular imaging [15]. Therefore it was tested whether the fluorescently labeled BC2-Nb (coupled to the organic dyes AlexaFluor488 or ATT0647 (BC2-NbAF488; BC2-NbATTO647)) is suitable to visualize BC2-tagged cellular proteins. To generate relevant cellular target structures the previously described fusion constructs mCherry-VIMBC2T or GFP-PCNABC2T were expressed in human cells (FIG. 4 a). Fluorescent constructs of vimentin become incorporated into the cellular intermediate filament network and visualize vimentin fibers in the cytoplasm upon transient cellular expression [16], whereas GFP-PCNA is found at sites of DNA replication, forming characteristic spot-like structures in the nucleus during the S phase of the cell cycle [17]. The characteristic pattern of the applied fusion proteins allows the performing of co-localization studies using immunocytochemistry with the dye-labeled BC2-Nbs.

By staining of HeLa cells expressing mCherry-VIM$_{BC2T}$ with the BC2-Nb$_{AF488}$ a strong co-localization of the green nanobody signal along cytoplasmic vimentin structures shown in the red channel (FIG. 4 b, FIG. 10 a) was observed. Correspondingly, the BC2-Nb$_{ATTO647}$ revealed a clear co-localization with GFP-PCNA$_{BC2T}$ at replication foci during the S phase. The signals of both GFP-PCNA$_{BC2T}$ and BC2-Nb$_{ATTO647}$ were exclusively found in the nucleus, demonstrating the binding specificity of BC2-Nb. No nanobody signal was detected in cells expressing mCherry-VIM or GFP-PCNA constructs lacking the BC2-tag (FIG. 10 b). These data demonstrate that the fluorescently labeled BC2-Nb specifically binds to ectopically expressed BC2T fusion proteins and can therefore be applied for direct antigen detection in immunocytochemistry.

Example 6

Analysis of the Impact of Multiple Mutations or Truncations within the BC2 Tag on the Binding Efficiency of the BC2-Nb in Pulldown Assays As outlined in Example 3 it was demonstrated that BC2T residues at positions 1, 2, 4, 5, 7, 9, 11 and 12 of SEQ ID NO: 4 can be replaced. This was shown by using positional scanning peptide libraries displaying all 20 proteinogenic amino acids in one single position of the peptide.

To study the impact of multiple exchanges of amino acid residues within the BC2T on the binding performance in more detail, a mutated version of the BC2T was generated by exchanging six amino acid residues simultaneously. Hence, Asp (D) at Position 2 to a Val (V), Lys (K) at Position 4 to a Ser (S); Val (V) at Position 7 to Leu (L); His (H) at Position 9 to Gln (Q); Gln (Q) at Position 11 to Ser (S) and Gln (Q) at Position 12 to Ser (S) were replaced. By this in total 50% of the amino acid residues originally identified as the BC2T sequence (SEQ ID NO:5) were changed. The resulting amino acid sequence is called BC2Tmut. To test whether the simultaneous exchange of these amino acid residues affects the pulldown efficiency of proteins comprising the mutated BC2-tag (BC2mut), the BC2Tmut was genetically fused to GFP (GFP$_{BC2Tmut}$). For pulldown analysis the soluble protein fractions of E. coli cells expressing either wtGFP (control), C-terminally BC2-tagged GFP (GFP$_{BC2T}$) or GFP$_{BC2Tmut}$ were incubated with the BC2 nanotrap and the input, non-bound and bound fractions were analyzed by SDS-PAGE followed by Coomassie staining and immunoblotting (see FIG. 11). The obtained data shows that the BC2 nanotrap quantitatively precipitates GFP$_{BC2T}$ as well as GFP$_{BC2Tmut}$. From that it can be concluded that a multiple exchange of amino acid residues at the indicated positions does not affect the interaction and binding capacity of mutated BC2T to the BC2 nanotrap.

Next, it was analyzed whether N- or C-terminal truncation of the BC2T does affect the binding properties to the BC2-Nb. Therefore two constructs were generated. In the first construct (called BC2T-10) the last two Gln (Q) residues located at the C-terminus of the BC2T were deleted, resulting in the sequence PDRKAAVSHW (SEQ ID NO: 14). For a second construct the first two amino acid residues Pro (P) and Asp (D) located on the N-terminus of the BC2T (BC2T-8; RKAAVSHW) were additionally deleted. For binding studies the BC2T-10 and the BC2T-8 were genetically fused to GFP (GFP$_{BC2T-10}$; GFP$_{BC2T-8}$). For pulldown analysis the soluble protein fractions of E. coli cells expressing either wtGFP (control), C-terminally BC2-tagged GFP (GFP$_{BC2T}$), GFP$_{BC2T-10}$ or GFP$_{BC2T-8}$ were incubated with the BC2 nanotrap and the input, non-bound and bound fractions were analyzed by SDS-PAGE followed by immunoblotting using anti-GFP antibodies (see FIG. 12). The obtained data shows that the BC2 nanotrap precipitates GFP$_{BC2T-10}$ as well as GFP$_{BC2T-8}$ in a comparable manner as GFP tagged with the original BC2T (GFP$_{BC2T}$). This demonstrates that deletion of the two amino acid residues flanking the BC2T either at the N- or the C-terminus does not affect the interaction and binding capacity of the truncated BC2T to the BC2 nanotrap.

Example 7

Development of Improved Variations of BC2T

Using a rational design approach, variations of BC2T were developed with the aim to further improve the affinity of the BC2 tag to the BC2-Nb. To this end, BC2T residues at positions 1, 4, 5, 11 and 12 of SEQ ID NO:4 were substituted based on structural and biochemical data reported in FIG. 1 and Table 4 and on molecular modelling.

Two variations of BC2T, called pTag1 SEQ ID NO:33 and pTag2 SEQ ID NO:34, were designed that were found to display higher affinity to BC2-Nb than the original BC2T sequence (Table 5, FIG. 18). Using biolayer interferometry, the dissociation constant $K_D$ was determined to be 0.7 nM and 1.9 nM for the interaction between BC2-Nb and pTag1 SEQ ID NO:33 and pTag2 SEQ ID NO:34, respectively. In contrast, for original BC2T (SEQ ID NO:4), the $K_D$ for the interaction with BC2-Nb is 2.6 nM (as determined using biolayer interferometry). In particular, the dissociation rate constant $k_{off}$ is 7× slower for pTag1 SEQ ID NO:33 than for original BC2T (Table 5), explaining the unusually high affinity of BC2-Nb for pTag1 SEQ ID NO:34.

These improved variations of BC2T were validated for the application in protein purification and immunoprecipitation (FIG. 19). The protein mCherry was fused with the BC2T variations pTag1 SEQ ID NO:33 and pTag2 SEQ ID NO:34 (and also the original BC2T SEQ ID NO:4 for comparison) either at the N-terminus or the C-terminus and incubated with the BC2 nanotrap (FIG. 19 a). Subsequently, captured fusion protein was eluted using the corresponding peptide at a concentration of 100 μM. SDS-PAGE analysis of fractions of input, non-bound protein, eluted protein and protein still bound to BC2 nanotrap after elution (FIG. 19 a) shows that the improved BC2 tags enable the capture of a fusion protein irrespective of the localisation of the tag. Also, captured protein may be eluted using free peptide, i.e. under native, non-denaturing conditions. Thus, the improved variations of BC2T may be applied to one-step protein purification of a protein of interest fused to such a BC2T variation. Compared to original BC2T, the higher affinity of the improved BC2T variations to BC2-NB leads to a more efficient capture of the tagged protein, with up to 100% protein bound (FIG. 19 a).

A protein of interest fused to an improved variation of BC2T may be precipitated from a range of organisms using the BC2 nanotrap. As is shown in FIG. 19 b, the N-terminal fusion of pTag1 SEQ ID NO:33 to the protein mCherry allows the highly specific recovery of this fusion protein from lysates of the human cell line HEK293T, the *Trichoplusia ni* insect cell line High5 and the yeast *Saccharomyces cerevisiae* using the BC2 nanotrap. This experiment (FIG. 19 b) uses cell lines common in the art, which exemplifies the applicability of the BC2 nanotrap in conjunction with protein-tagging using BC2T variation pTag1 SEQ ID NO:33 to protein purification and precipitation from relevant systems of recombinant expression.

TABLE 5

Binding kinetics of two improved variations of BC2T compared to wildtype BC2T

| Sequence | $K_D$ (nM) | $k_{on}$ (M$^{-1}$s$^{-1}$) | $k_{off}$ (s$^{-1}$) | $\chi^2$ | $R^2$ |
|---|---|---|---|---|---|
| pTag1 | 0.7 | 9.2 ± 0.5 × 10$^4$ | 6.8 ± 0.4 × 10$^{-5}$ | 0.09 | 0.9997 |
| pTag2 | 1.9 | 1.1 ± 0.1 × 10$^5$ | 2.0 ± 0.1 × 10$^4$ | 0.17 | 0.9992 |
| BC2T | 2.6 | 1.9 ± 0.1 × 10$^5$ | 5.0 ± 0.1 × 10$^4$ | 0.18 | 0.9987 |

Table legend:
The binding of BC2-Nb to BC2T (SEQ ID NO: 4) and the two improved variations (pTag1 SEQ ID NO: 33 and pTag2 SEQ ID NO: 34) thereof was analysed using biolayer interferometry (see FIG. 13 for raw data). Listed are the dissociation constant ($K_D$), the association ($k_{on}$) and dissociation ($k_{off}$) rate constants and markers of the quality of fit of a 1:1 binding model ($\chi^2$, $R^2$). The constants reported for original BC2T differ from those listed in Table 1 because kinetics were analysed using a different method.

In summary, a rational design approach enabled the development of improved variations of BC2T that are characterised by higher affinity to BC2-Nb. These improved variations may be fused to the N-terminus or C-terminus of a protein of interest and allow the efficient purification of such a fusion protein from a variety of organisms. Also, like original BC2T, these improved BC2T tags can be eluted with the BC2 nanotrap using native, non-denaturing conditions.

Example 8

Materials and Methods

Expression Plasmids

For bacterial expression of C-terminal BC2-tagged GFP (GFP$_{BC2T}$) pEGFP-C1 (Clontech) was used as template. The sequence encoding GFP$_{BC2T}$ was amplified by polymerase chain reaction (PCR) using the oligonucleotide primers GFP$_{BC2T}$_for (5'-GCA CCA TGG ATG GTG AGC AAG GGC GAG G-3'; SEQ ID NO:15) and GFP$_{BC2T}$_rev (5'-GAC GTC GAC TTA CTG CTG CCA GTG ACT AAC A-3'; SEQ ID NO:16). The PCR fragment was cloned into the NcoI/SalI restriction sites of pTRC2A (Life Technologies). For expression of the C-terminal BC2-tagged GFP with a N-terminal His$_6$-tag (His$_6$-GFP$_{BC2T}$) the sequence encoding GFP$_{BC2T}$ was amplified by PCR using the oligonucleotide primers His$_6$-GFP$_{BC2T}$_for (5'-CAG GGA TCC GAG TGA GCA AGG GC-3'; SEQ ID NO:17) and His$_6$-GFP$_{BC2T}$_rev (5'-CAG GGT ACC TTA CTG CTG CCA GTG ACT AA-3'; SEQ ID NO:18). The PCR fragment was cloned into BamHI/KpnI restriction sites of pRSET B (Invitrogen) adding an N-terminal His$_6$-tag.

To generate a GFP fusion construct comprising a 50% modified BC2tag pEGFP-C1 (Clontech) was used as template. The sequence encoding GFP$_{BC2Tmut}$ was amplified by polymerase chain reaction (PCR) using the oligonucleotide primers GFP$_{BC2Tmut}$_for (5'-GGA TCC GAT GGT GAG CAA GGG CGA G-3'; SEQ ID NO:19) and GFP$_{BC2Tmut}$_rev (5'-GGT ACC TTA GCT GCT CCA CTG GCT CAG CGC CGC GCT CCG GAC CGG CTT GTA CAG CTC GTC CAT GC-3'; SEQ ID NO:20). The PCR fragment was cloned into the BamHI/KpnI restriction sites of the previously generated GFP$_{BC2T}$ expression construct.

To generate a bacterial expression vector encoding GFP with a N-terminal His$_6$-tag and a C-terminal shortened version of the BC2T (BC2T-10 or BC2T-8) the sequence encoding GFP$_{BC2T-10}$ or GFP$_{BC2T-8}$ was amplified by PCR using pEGFP-C1 (Clontech) as template. For PCR the following oligonucleotide primers were used: His$_6$-GFP$_{BC2T-10}$_for: (5'-cccc GGA TCC GAT GGT GAG CAA GGG CGA GG-3'; SEQ ID NO:21) and His$_6$-GFP$_{BC2T-10}$_rev (5'-cccc GGT ACC TTA CCA ATG TGA CAC CGC TGC TTT GCG GTC AGG CTT GTA CAG CTC GTC CAT GCC-3'; SEQ ID NO:22) or His$_6$-GFP$_{BC2T-8}$_for (5'-cccc GGA TCC GAT GGT GAG CAA GGG CGA GG-3'; SEQ ID NO:23) and His$_6$-GFP$_{BC2T-8}$_rev (5'-cccc GGT ACC TTA CCA GTG GGA AAC GGC TGC TTT ACG CTT GTA CAG CTC GTC CAT G-3'; SEQ ID NO:24).

For mammalian expression of C-terminal BC2-tagged GFP pEGFP-C1 was used as template. The sequence encoding the mammalian eGFP$_{BC2T}$ construct was amplified by PCR using the oligonucleotide primers eGFP$_{BC2T}$_for (5'-AAG CTA GCG CTA CCG GTC GCC ACC ATG-3'; SEQ ID NO:25) and eGFP$_{BC2T}$_rev (5'-AAG GTA CCT TAT TGC TGC CAG TGA CTA ACA GCC GCT TTT CTG TCT GGC TTG TAC AGC TCG TC-3': SEQ ID NO:26). The PCR fragment was cloned into the NheI/KpnI site of the pEGFP-C1 vector.

For mammalian expression of N-terminal BC2-tagged GFP ($_{BC2T}$GFP) the nucleotide sequence encoding the BC2-Tag (5'-GCT AGC ATG CCC GAT CGT AAG GCT GCG GTC TCT CAT TGG CAA CAG AGA TCT-3'; SEQ ID NO:27) harboring NheI and BglII restriction sites respectively was synthesized (MWG). Subsequently the tag was cloned into NheI/BglII sites of pEGFP-N1 (Clontech). The obtained plasmid was digested with XhoI and NheI, blunted using the Klenow enzyme (Roche) and re-ligated resulting in the desired construct.

For mammalian expression of mCherry-Vimentin$_{BC2T}$ a mCherry-Vimentin construct [18] was used as template. The nucleotide sequence encoding mCherry-Vimentin$_{BC2T}$ was amplified by PCR using the oligonucleotide primers mCherry-Vimentin$_{BC2T}$_for (5'-AAA AGC TTA GGT GGA GGA GGT TCT TCC ACC AGG TCC GTG TC-3'; SEQ ID NO:28) and mCherry-Vimentin$_{BC2T}$_rev (5'-AAG GTA CCC TAT TGC TGC CAG TGA CTA ACA GCC GCT TTT CTG TCT GGT TCA AGG TCA TCG TG-3'; SEQ ID NO:29). The PCR fragment was cloned into the HindIII/KpnI sites of the mCherry-Vimentin vector.

For mammalian expression of GFP-PCNA$_{BC2T}$ GFP-PCNA [17] was used as template. The sequence encoding GFP-PCNA$_{BC2T}$ was amplified by PCR using the oligonucleotide primers GFP-PCNA$_{BC2T}$_for (5'-GTA TGG CTT CGT GGG GAT CCC CG-3'; SEQ ID NO:30) and GFP-PCNA$_{BC2T}$_rev (5'-GGG GTC TAG ACT AAA GGT ACC CTA TTG CTG CCA GTG ACT AAC AGC CGC TTT TCT GTC TGG AGA TCC TTC TTC ATC CTC-3'; SEQ ID NO:31). The PCR fragment was cloned into the BamHI/XbaI restriction sites of GFP-PCNA vector.

To generate a bacterial expression vector encoding mCherry with an N-terminal His$_6$-tag and a C-terminal BC2T or variations thereof, the sequences encoding BC2T (SEQ ID NO:4) and the variations pTag1 SEQ ID NO:33 and pTag2 SEQ ID NO:34 were synthetized as oligonucleotides, annealed and cloned into the BrsGI and HindIII restriction sites of the plasmid vector pRSET-B_mCherry (ThermoFisher Scientific). To this end, following oligonucleotides were used: mCherry_BC2T_fw (5'-GTA CAG TGG TCC GGA TCG CAA AGC GGC GGT GAG CCA TTG GCA GCA GTA AA-3': SEQ ID NO:35) and mCherry_BC2T_rv (5'-AGC TTT TAC TGC TGC CAA TGG CTC ACC GCC GCT TTG CGA TCC GGA CCA CT-3'; SEQ ID NO:36); mCherry_SEQ33_fw (5'-GTA CAG TGG TCC GGA TCG CGT GCG CGC GGT GAG CCA TTG GAG CAG CTA AA-3'; SEQ ID NO:37) and mCherry_SEQ33_rv (5'-AGC TTT TAG CTG CTC CAA TGG CTC ACC GCG CGC ACG CGA TCC GGA CCA CT-3'; SEQ ID NO:38); mCherry_SEQ34_fw (5'-GTA CAGT GGT GCG GAT CGC GTG CGC GCG GTG AGC CAT TGG AGC AGC TAA A-3'; SEQ ID NO:39) and mCherry_SEQ34_rv (5'-AGC TTT TAG CTG CTC CAA TGG CTC ACC GCG CGC ACG CGA TCC GCA CCA CT-3': SEQ ID NO:40).

To generate a bacterial expression vector encoding mCherry with a C-terminal His$_6$-tag and an N-terminal BC2T or variations thereof, the sequences encoding BC2T (SEQ ID NO:4) and the variations pTag1 SEQ ID NO:33 and pTag2 SEQ ID NO:34 were synthetized as oligonucleotides, annealed and cloned into the NdeI and BamHI restriction sites of a modified variation of the plasmid vector pRSET-B_mCherry (ThermoFisher Scientific) that encodes a C-terminal His$_6$-tag. To this end, following oligonucleotides were used:

```
mCherry_BC2T_fw2
(5'-TAT G CC GGA TCG CAA AGC GGC GGT GAG CCA

TTG GCA GCA GGG CTC G-3'; SEQ ID NO: 41)
and mCherry_BC2T_rv2
(5'-GAT CCG AGC CCT GCT GCC AAT GGC TCA CCG

CCG CTT TGC GAT CCG GCA-3'; SEQ ID NO: 42);

mCherry_SEQ33_fw2
(5'-TAT GCC GGA TCG CGT GCG CGC GGT GAG CCA

TTG GAG CAG CGG CTC G-3'; SEQ ID NO: 43)
and mCherry_SEQ33_rv2
(5'-GAT CCG AGC CGC TGC TCC AAT GGC TCA CCG

CGC GCA CGC GAT CCG GCA-3'; SEQ ID NO: 44);

mCherry_SEQ34_fw2
(5'-TAT GCC GGA TCG CGT GCG CGC GGT GAG CCA

TTG GAG CAG CGG CTC G-3'; SEQ ID NO: 45)
and mCherry_SEQ34_rv2
(5-GAT CCG AGC CGC TGC TCC AAT GGC TCA CCG

CGC GCA CGC GAT CCG CCA-3'; SEQ ID NO: 46).
```

Protein Production and Purification

Expression and purification of the BC2 nanobody was performed as described previously [11]. Expression and purification of wtGFP or modified versions thereof was performed as described previously [19]. Purity of all proteins was evaluated to be at least 95% based upon sodium dodecyl sulfate-polyacrylamide gel electrophoresis (SDS-PAGE) analysis. Protein concentration was spectroscopically determined.

Complex Formation

For complex formation, a BC2-Nb solution at 2 mg/ml was mixed and incubated with a threefold molar excess of peptide in 10 mM Tris/HCl pH 7.4, 100 mM NaCl buffer for 1 h at room temperature. Excess of peptide was removed via size exclusion chromatography (Superdex 200 increase, GE Healthcare). Complex formation was confirmed by liquid chromatography mass spectrometry using a Shimadzu LCMS 2020 with a Phenomenex Kinetex (2.6 u C18 100 Å) column. The complex was concentrated to 13.7 mg/ml and used for crystallization experiments.

Crystallization

Unliganded BC2-Nb was crystallized using hanging drop vapor diffusion by mixing 3.2 mg/ml protein solution with crystallization buffer (0.1 M MES/imidazole pH 6.7, 12.5% [v/v] 2-Methyl-2,4-pentanediol (MPD), 7.5% [w/v] PEG 1000, 7.5% [w/v] PEG 3350, 3 mM alcohol mix) in a 1:1 ratio at 20° C. The BC2-Nb/BC2T complex was crystallized using hanging drop vapor diffusion, mixing 13.7 mg/ml complex solution with crystallization buffer (0.1 M MES/imidazole pH 6.5, 12.5% [v/v] 2-Methyl-2,4-pentanediol (MPD), 12.5% [w/v] PEG 1000, 12.5% [w/v] PEG 3350, 4 mM amino acid mix) in a 1:1 ratio at 20° C. In both cases, crystals were transferred into crystallization solution containing 30% [v/v] MPD for cryoprotection, and flash cooled in liquid nitrogen after incubation for 30 s. One Dataset from BC2-Nb and four dataset from the same crystal of BC2-Nb/BC2T complex at different positions were collected with a beam wavelength of 0.918409 Å at beamline MX 14.2 of BESSY II at the Helmholtz-Zentrum Berlin (HZB).

X-ray data were reduced and in the case of BC2-Nb/BC2T complex, merged using the XDS package [20]. Initial phases for the BC2-Nb data were obtained by molecular replacement using PHASER [21] with a CHAINSAW [22, 23] modified model of a nanobody (PDB ID:2X1O) containing only the core region. The structure of the BC2-Nb/

BC2T complex was then solved using the unliganded BC2-Nb structure as a search model in molecular replacement. Both structures were refined using PHENIX.refine [24], REFMACS [25] and COOT [26]. The two structures were validated with MOLPROBITY [27]. The Ramachandran plot shows 100% (BC2-Nb), 98.1% (BC2-Nb/BC2T complex) in favored and 100% in allowed regions.

Structure Visualization and Analyzation

Superpositions of structures and calculation of RMSD values were conducted using the Phenix structure_comparison. Images of crystal structures were prepared with PyMol.

Mass Spectrometry Analysis of Binding Specificities with Synthetic Positional Scanning Peptide Libraries To investigate the binding specificity of the BC2T and derived mutants peptide libraries for each amino acid position of the sequence PDRKAAVSHWQQ (SEQ ID NO:4) were synthesized with acetyl and amide groups located at the N-termini or C-termini respectively (Intavis). Precipitation studies were carried out incubating 60 pmol peptide of a single position library with 2 µl BC2-Nb immobilized on agarose beads. Incubations were performed in 300 µl PBS/0.01% CHAPS for 1 h on a HulaMixer (Life Technologies). Subsequent to a centrifugation step 10 µl supernatant were analyzed in a LC-MS procedure. Peptides were separated using an UltiMate3000 RSLCnano System (Thermo Scientific), composed of a C18 PepMap100µ-Precolumn (300 µm×5 mm; particle size: 5 µm; pore size: 100 Å—Thermo Scientific) and a C18 analytical column (Acclaim Rapid Separation LC (RSLC) Column: 150 mm×5 mm; particle size: 2.2 µm; pore size: 100 Å—Thermo Scientific). A step gradient was applied starting at 8% and ending after 20 min at 30% eluent B (80% acetonitrile, 20% $H_2O$, 0.1% formic acid). Peptides were analyzed using a FULL-MS-strategy detected by a Q Exactive Plus mass spectrometer (Thermo Scientific). As maximal injection time 100 ms was chosen while setting the AGC target to 3E6. The resolution was set to 70.000. Half-maximal signal areas were referenced to control precipitation approaches using a GFP-specific nanobody immobilized on agarose beads. All experiments were done in triplicates.

Cell Culture and Transfection

HEK293T and HeLa cells were cultivated in DMEM (high glucose, pyruvate) supplemented with 10% FCS, 2 mM L-glutamine and Pen Strep (all from Gibco, Life Technologies). Cells were cultivated at 37° C. in a humidified chamber with a 5% $CO_2$ atmosphere and were trypsinized for passaging. To generate DNA/PEI complexes for transient transfection in P100 dishes, 24 µg DNA were mixed with 108 µl polyethyleneimine (PEI, Sigma Aldrich) prediluted with 750 µl Opti-MEM (Gibco, Life Technologies) and incubated for 10 min at RT. For transfection of cells in a 96-well plate, 200 ng of DNA and 1.5 µl of PEI was used.

Generation of Soluble Protein Fraction from Bacterial Cells

Pellets of $E.\ coli$ cells expressing GFP or $GFP_{BC2T}$ derived from 1 L culture were homogenized for 90 min at 4° C. in 500 µl PBS containing 0.1 mg/ml lysozyme, 5 µg/ml DNaseI, 50 µg/ml PMSF and 1× protease inhibitor mix B (Serva) followed by sonication (10×10 sec pulses). After a centrifugation step (10 min at 18.000×g, 4° C.), the soluble protein fraction was transferred into a new cup and the protein concentration of each lysate was determined using Coomassie Plus according to the manufacturer's protocol (Thermo Fisher Scientific).

Surface Plasmon Resonance

The affinity measurements of the BC2 nanobody and the indicated mutants thereof to $GFP_{BC2T}$ were performed using surface plasmon resonance spectroscopy with a Biacore 3000 instrument (GE-Healthcare). $GFP_{BC2T}$ was covalently coupled on dextran fibers of a CMS sensorchip (GE Healthcare) to a response level of 500 RU. One flow cells was activated and blocked in the absence of protein to determine background, another was loaded with untagged GFP as a control against unspecific binding. For kinetic measurement, six concentrations ranging from 7.8125 nM to 250 nM of either BC2-Nb, $BC2-Nb_{R106S}$ or $BC2-Nb_{R106E}$ were injected. Each measurement was done in duplicates. As running/dilution buffer 10 mM HEPES pH 7.4, 150 mM NaCl, 0.5% surfactant Tween was used. Measurements were performed at 25° C. For the association of BC2-Nb a flow rate of 50 µl/min for 15 s and for the dissociation a flow rate of 50 µl/min for 600 s was applied. The regeneration was induced by injection of 23 µl regeneration solution at a flow rate of 30 µl/min. As regeneration solution 10 mM glycine-HCl pH 2.0 was used. The data was evaluated using the software Bia evaluation 4.1 and the 1:1 Langmuir binding model with mass transfer.

SDS-PAGE and Immunoblotting

Denaturing polyacrylamide gel electrophoresis (SDS-PAGE) was performed according to standard procedures. Protein samples were boiled in 2×SDS-sample buffer (60 mM Tris/HCl, pH 6.8; 2% (w/v) SDS; 5% (v/v) 2-mercaptoethanol, 10% (v/v) glycerol, 0.02% bromophenol blue). For immunoblotting proteins were transferred on nitrocellulose membranes (Bio-Rad Laboratories).

Antibodies

For immunoblotting the following primary antibodies were used: anti-GFP clone 3H9 (ChromoTek), anti-PCNA clone 16D10 (ChromoTek), anti-Vimentin clone V9 (Sigma Aldrich), anti-GAPDH (abcam), anti-β-catenin clone 14 (BD-Biosciences). For detection fluorophore-labeled species-specific secondary antibodies (Alexa-647, goat-anti-rabbit, goat-anti-rat; goat-anti-mouse Life Technologies) were used. Blots were scanned on the Typhoon-Trio laser scanner (GE Healthcare).

Immunoprecipitation of BC2-tagged Proteins

HEK293T cells transiently expressing eGFP, $eGFP_{BC2T}$ or $B_{C2T}eGFP$, eGFP-PCNA, $eGFP-PCNA_{BC2T}$, mCherry-Vimentin, $mCherry-Vimentin_{BC2T}$ were washed and harvested in phosphate buffered saline (PBS), snap-frozen in liquid nitrogen and stored at −20° C. Cell pellets were homogenized in 200 µl lysis buffer (10 mM Tris/Cl pH 7.5, 150 mM NaCl, 0.5% NP40, 1 µg DNaseI, 2 mM $MgCl_2$, 2 mM PMSF, 1× protease inhibitor mix M (Serva) by repeated pipetting for 40 min on ice. After a centrifugation step (10 min at 18.000×g) the protein concentration of each lysate was determined using a Pierce BCA Protein Assay Kit (Thermo Fisher Scientific) according to manufacturer's protocol and the protein solutions were adjusted with dilution buffer (10 mM Tris/Cl pH 7.5, 150 mM NaCl, 2 mM PMSF) to a concentration of 1 mg/ml. 2% of the supernatant were added to SDS-containing sample buffer (referred to as input). 50 µl BC2 nanotrap (slurry) per 100 µl supernatant were added followed by incubation for 1 h on an end-over-end rotor at 4° C. After a centrifugation step (2 min, 2500×g) the precleared supernatant was transferred to a new cup. 2% were added to SDS-containing sample buffer (referred to as non-bound). After four washing steps, BC2 nanotrap bound proteins were eluted by boiling the beads in 50 µl SDS-sample buffer or by incubation with indicated elution buffers. Samples were analyzed by SDS-PAGE followed by immunoblotting. Immunoblots were probed with indicated antibodies.

Immunoprecipitation at Harsh Conditions

For each condition, 50 µl bead-slurry were mixed with 100 µl of soluble protein fraction from *E. coli* lysate (c=1 mg/ml) and 150 µl of a solution containing either a detergent or a chaotropic agent, resulting in a final concentration as indicated below. As chaotropic agents urea (0 M, 1 M, 2 M, 4 M) and guanidinium chloride (0 M, 0.375 M, 0.75 M, 1.5 M, 3 M) were used and as a detergent SDS (0%, 0.1%, 0.5%, 1%, 2%) was used. After incubation on an end-over-end rotor for one hour at 4° C. and a centrifugation step (2 min, 2500×g, 4° C.) the supernatants were discarded and the remaining beads were washed twice in PBS before boiling in 50 µl 2× sample buffer. 10% of each bead bound (B) fraction were analyzed by SDS-PAGE and immunoblotting using an anti-GFP antibody.

Elution of Bound BC2-Tagged Protein

For the elution experiments 40 µl of BC2 nanotrap (slurry) were incubated with 400 µl soluble protein extract (c=1 mg/ml) derived from *E. coli* cells expressing $GFP_{BC2T}$ for 1 h at 4° C. on an end-over-end rotor. After a centrifugation step (2500×g, 4° C., 2 min) the supernatant was discarded and the beads were washed four times in ice-cold PBS including a cup change after the second washing step. Subsequently, beads were pelleted and incubated with 80 µl of the indicated elution conditions for 15 min at RT. The following elution conditions have been tested: peptide elution: 0 mM, 0.01 mM, 0.1 mM or 1 mM BC2-peptide dissolved in in 0.2 M Tris/Cl pH 7.4, 150 mM NaCl; acidic elution: 0.2 M Glycine-HCl adjusted to pH 1, pH 2 or pH 3; alkaline elution: 0 mM, 1 mM, 10 mM or 100 mM NaOH; elution with sodium thiocyanate: 0 M, 1 M, 2 M, or 3 M NaSCN. The eluates were collected and boiled in 1×SDS containing sample buffer and the remaining beads were washed twice in PBS before boiling in 40 µl 2× sample buffer. 10% of each elution (release, R) and bead bound (bound, B) fraction were analyzed by SDS-PAGE and immunoblotting using an anti-GFP antibody.

Immunofluorescent Staining with Fluorescently Labeled Nanobody

Purified BC2 nanobody (1 mg) was labeled with the NHS-activated fluorescent dyes Alexa488 (Life technologies) or Atto647 (Atto-Tec) according to manufacturer's guidelines. After coupling, unbound dye was removed by separation on PD-10 Desalting Columns (GE Healthcare). For immunoblot analysis, 5 µg of $BC2-Nb_{AF488}$ was diluted in 4 ml 3% BSA diluted in TBS, 0.05% Tween20 and Western blots were incubated for 1 h at RT.

For immunocytochemistry 5-10×10³ adherent HeLa cells per well of a µClear 96 well plate (Greiner) were transfected with plasmids coding for C-terminally BC2-tagged vimentin or PCNA. After 24 h, cells were washed once with PBS and fixed with 4% w/v paraformaldehyde (PFA) in PBS for 15 min at RT or with methanol for 15 min at −20° C. After removal of the fixative and washing twice with PBS, cells were blocked and permeabilized with 3% w/v BSA and 0.1% v/v Triton X-100 in PBS for 1 h at RT. Subsequently, labeled BC2 nanobody was added with a final concentration of 10-15 µg/ml and 4',6-diamidino-2-phenylindole (DAPI, Sigma Aldrich) with a final concentration of 1 µg/ml for overnight incubation at 4° C. Unbound nanobody and DAPI were removed by washing 3 times with a mixture of PBS and 6% v/v 5 M NaCl in H$_2$O. Images of FIG. 4 *b* and FIG. 10 *b* were acquired with an Image Xpress micro XL system. Confocal images of FIG. 10 *a* were acquired with an ImageXpress Micro Confocal.

Fluorescence Spectroscopy

Fluorescence assays were performed by scanning a 96 well microplate (Nunc) on a Typhoon Trio (GE Healthcare Life Sciences), excitation: 488 nm, emission filter settings: 520 nm BP 40

Biolayer Interferometry

The affinity measurements of BC2-Nb to BC2T and improved variations pTag1 and pTag2 were performed using biolayer interferometry using a BLItz system instrument (fortéBIO). Biotinylated peptides of BC2T and its variations were immobilised on Streptavidin biosensors (fortéBIO). The loaded sensor was sequentially dipped into BLItz buffer (phosphate buffered saline, 0.1% (m/v) BSA, 0.02% (v/v) Tween20) for 120 s to determine base line signal, in a solution of BC2-Nb in BLItz buffer (concentration of 5-50 nM) for 120 s to determine association and in BLItz buffer for 600 s to determine dissociation. The shaking rate was 1200 rpm. As a reference, each peptide was also incubated with BLItz buffer only according to the protocol above. In a control experiment, Streptavidin biosensors were incubated with BC2-Nb without prior peptide immobilisation. The sensor was regenerated by sequential dips into 10 mM glycine pH 2.0 and BLItz buffer (repeated three times). Raw data were analysed using the software BLItz Pro (fortéBio) and a 1:1 binding model.

Example 9

BC2 Nanobody Generation

Identification of BC2-nanobody

Material & Methods $V_HH$ Libraries

Alpaca immunizations with purified β-catenin protein and $V_HH$-library construction were carried out as described previously in Rothbaueret et al., (2006) (*Targeting and tracing antigens in live cells with fluorescent nanobodies. Nature methods* 3, 887-889). Animal immunization has been approved by the government of Upper Bavaria (Permit number: 55.2-1-54-2531.6-9-06). In brief, six weeks after immunization of two animals (*Vicugna pacos*) with either GST-β-catenin or C-terminal histidine-tagged β-catenin (β-catenin-His$_6$), ~100 ml blood were collected and lymphocytes were isolated by Ficoll gradient centrifugation using the Lymphocyte Separation Medium (PAA Laboratories GmbH). Total RNA was extracted using TRIzol (Life Technologies) and mRNA was reverse transcribed to cDNA using a First-Strand cDNA Synthesis Kit (GE Healthcare). The $V_HH$ repertoire was isolated in 3 subsequent PCR reactions using following primer combinations (1) CALL001 (5'-GTC CTG GCT GCT CTT CTA CA A GG-3'; SEQ ID NO:47) and CALL002 (5'-GGT ACG TGC TGT TGA ACT GTT CC-3'; SEQ ID NO:48) (2) SM017 and SM018 (5'-CCA GCC GGC CAT GGC TCA GGT GCA GCT GGT GGA GTC TGG-3'; SEQ ID NO:49, and 5'-CCA GCC GGC CAT GGC TGA TGT GCA GCT GGT GGA GTC TGG-3', SEQ ID NO:50, respectively) and reverse primer CALL002 and (3) A4short (5'-CAT GCC ATG ACT CGC GGC CAC GCC GGC CAT GGC-3'; SEQ ID NO:51) and reverse Primer 38 (5'-GGA CTA GTG CGG CCG CTG GAG ACG GTG ACC TGG GT-3'; SEQ ID NO:52) introducing SfiI and NotI restriction sites. The $V_HH$ library was subcloned into the SfiI/NotI sites of the pHEN4 phagemid vector (for reference see Arbabi Ghahroudi, et al., (1997)

*Selection and identification of single domain antibody fragments from camel heavy-chain antibodies. FEBS Lett* 414, 521-526)

V$_H$H Screening

The V$_H$H domains were expressed on phages after infecting the cells of the 'immune' library in pHEN4 with M13K07 helper phages. V$_H$H with specificity for β-catenin were enriched by two consecutive rounds of in vitro selection using full-length β-catenin coated on microtiter plates (10 µg/well). Bound phages were eluted with 100 mM tri-ethylamine, TEA (pH 10.0). The eluate was immediately neutralized with 1 M Tris/HCl (pH 7.4) and used to infect exponentially growing TG1 cells. The enrichment of phage particles carrying the antigen-specific V$_H$H domains was monitored by comparing the number of phages eluted from wells with captured versus non-captured antigen. Following panning 96 individual clones of each antigen were screened by standard ELISA procedures using a horseradish peroxidase-labeled anti-M13 monoclonal antibody (GE-Healthcare)

Expression Plasmids

For bacterial expression of V$_H$H domains (nanobodies, Nbs), sequences were cloned into the pHEN6 vector (for reference see Arbabi Ghahroudi et al., (1997) *Selection and identification of single domain antibody fragments from camel heavy-chain antibodies. FEBS Lett* 414, 521-526), thereby adding a C-terminal 6×His-tag for IMAC purification as described previously (for reference see Rothbauer et al., (2008) *A versatile nanotrap for biochemical and functional studies with fluorescent fusion proteins. Molecular & cellular proteomics: MCP* 7, 282-289). Expression and purification of β-catenin-specific Nbs was carried out as described previously in Rothbauer et al., (2008) *Molecular & cellular proteomics: MCP* 7, 282-289).

The expression plasmids for the β-catenin fusions have been described previously in Aberle et al., (1994) Assembly of the cadherin-catenin complex in vitro with recombinant proteins. Journal of cell science 107 (Pt 12), 3655-3663; and Luckert et al., (2011) Snapshots of protein dynamics and post-translational modifications in one experiment-beta-catenin and its functions. *Molecular & cellular proteomics*: MCP 10, M110 007377). For protein production, *E. coli* BL21(DE3) CodonPlus-RIL cells (Stratagene) were used.

Microsphere-based Sandwich Immunoassays (See FIG. 13)

BC2-Nb was covalently immobilized on microspheres using a modified manufacturer's protocol described in Poetz et al., ((2009) Microsphere-based co-immunoprecipitation in multiplex. *Analytical biochemistry* 395, 244-248). Immobilized BC2-Nb was incubated with purified proteins representing full-length β-catenin or the following domains of β-catenin: N-terminus aa 1-119, armadillo domain aa 120-683 and C-terminus aa 683-781. Purified Glutathion-S-transferase (GST) was used as a negative control. Concentrations range from 0.25 µg/ml to 2 µg/ml. Bound proteins were detected with domain-specific antibodies including ABC antibody clone 8E7 (Merck Millipore) specific for the N-terminus, anti-β-catenin 9G10 (Merck Millipore) targeting the armadillo domain and anti-β-catenin clone 14 (Becton Dickinson) specifically recognizing the C-terminus. To detect unspecific binding of the BC2-Nb to GST an antibody against GST (6G9, ChromoTek) was used. Secondary species-specific antibodies (anti-mouse, anti-rat, anti-rabbit) tagged with phycoerythrin (PE) (Dianova) were used for immunodetection of antibody/protein complexes. The microspheres were measured in a FlexMap 3D instrument (Luminex). The evaluation of the data was done with Excel (Microsoft).

Surface Plasmon Resonance

The affinity measurement of the BC2-Nb was performed using surface plasmon resonance spectroscopy with a Biacore 3000 instrument (GE-Healthcare). Recombinant β-catenin was covalently coupled on dextran fibers of a CM5-chip (GE-Healthcare) according to the manufacturer's protocol. β-catenin was coupled to a response ranging from 1200 to 3000 RU. One flow cells was activated and blocked in the absence of protein to determine background. For kinetic measurement five concentrations ranging from 0.625 nM to 5 µM of the BC2-Nb were injected. Each measurement was done in duplicates. As running/dilution buffer 10 mM HEPES pH 7.4, 150 mM NaCl, 0.5% surfactant P20 was used. Measurements were performed at 25° C.: For the association of the BC2-Nb a flow rate of 30 µl/min for 3 minutes and for the dissociation a flow rate of 60 µl/min for 5 minutes was applied. The dissociation was induced by two injections of regeneration solution of 15 µl each at the identical flow rates. As regeneration solution was used BC2: 100 mM $H_3PO_4$. The data was evaluated using the software Bia evaluation 4.1 and the 1:1 Langmuir binding model.

Immobilization of Peptides onto OVA-microspheres

MagPlex microspheres (Luminex), with varying IDs per peptide (n=29), were coated with Imject ovalbumin (OVA) (Thermo Fisher Scientific). Coating procedure was done according to a modified manufacturer's protocol (see Poetz et al., ((2009) Microsphere-based co-immunoprecipitation in multiplex. *Analytical biochemistry* 395, 244-248). Subsequently, 250.000 microspheres of each ID were washed one time with 1×PBS, the OVA was activated with 1660 µM sulfosuccinimidyl 4-[p-maleimidophenyl] butyrate (sulfo-SMPB) (Thermo Fisher Scientific) dissolved in dimethyl sulfoxide (Roth) and diluted to the final concentration with 1×PBS. The activation of OVA-microspheres was done for 1 h at RT on a plate incubator (Eppendorf) at 650 rpm. In parallel, the 29 peptides were reduced with tris(2-carboxyethyl)phosphine (TCEP). Each peptide was diluted in 1×PBS containing 40% (v/v) acetonitrile to a final concentration of 600 µM. An equimolar solution of TCEP in PBS was prepared and one volume of each the peptide solutions and the TCEP-solution were mixed and incubated for 20 min at RT at 250 rpm on a plate incubator. After activation, the OVA-microspheres were washed two times with 1×PBS 0.005% Triton X-100 to remove excess sulfo-SMPB and solubilized in reduced peptide solutions. Coupling procedure of the peptides to OVA was done for 1 h at RT with continuous shaking at 650 rpm. Afterwards, the microspheres were again washed two times with 1×PBS 0.005% Triton X-100 and transferred into a blocking buffer containing 10 mg/ml BSA dissolved in 1×PBS to block all free activated OVA. The blocking of OVA was done for 10 min at room temperature at 850 rpm followed by an additional washing step with 1×PBS containing 0.005% Triton and transferred into 1× Roche-buffer (Roche) containing 0.05% sodiumazid for storage.

Epitope Mapping

For the epitope mapping, BC2-Nb was biotinylated with sulfo-NHS-LC-biotin (Thermo Fisher Scientific) using manufacturer's protocol. The biotinylated BC2-Nb was then used as detection reagent in a sandwich-immunoassay similar to the domain mapping procedure using the peptide coated OVA-microspheres to screen for specific epitopes. As negative controls, microspheres comprising Ovalbumin and the Myc-peptide (EQKLISEEDL) covalently coupled to OVA-microspheres were used. The biotinylated BC2-Nb was applied at a concentration of 1 µg/ml. Peptide-bound BC2-Nb was detected with 2.5 µg/ml streptavidin-phycoerythrin (PE) solution (Prozyme) dissolved in 1× Roche buffer 0.05% Tween. Evaluation of the PE-signals were done in a Flexmap 3D (Luminex).

Results

To generate β-catenin-specific nanobodies, two alpacas (*Vicugna pacos*) were immunized with purified recombinant human β-catenin. A phagemid library was generated comprising ~2×10$^7$ clones representing the full repertoire of the variable heavy chains of heavy chain antibodies (V$_H$Hs or nanobodies, Nbs) derived from one animal. The library was subjected to phage display and biopanning was performed using full-length β-catenin. Two subsequent phage display cycles revealed an enrichment of 14 unique nanobody sequences which were positively tested for antigen binding in a solid-phase phage ELISA.

Individual Nbs were cloned with a C-terminal 6×His-tag, expressed in *Eschericha coli* (*E. coli*) and purified using immobilized metal ion affinity chromatography (IMAC) followed by size exclusion chromatography. It was tested whether the β-catenin-specific Nbs are functional as capture molecules in a microsphere-based sandwich immunoassay system. To this end, the Nbs were immobilized on magnetic microspheres (MagPlex) and were incubated with decreasing amounts of β-catenin. Bound β-catenin was detected with a C-terminus-specific antibody (clone 14/BD).

With BC2-Nb one of the best-performing nanobody was chosen. In combination with the C-terminal β-catenin-specific antibody as detector, bound β-catenin was detectable down to ~1 ng/ml when using BC2 as capture molecule (see FIG. 14).

For further characterization of the selected BC2-Nb, its affinity to recombinant β-catenin was determined using surface plasmon resonance (SPR). After immobilizing β-catenin, the association/dissociation rates were measured by injecting serial dilutions of five different concentrations for BC2-Nb. By this, we determined affinities ($K_D$ values) in the low nanomolar range of ~3.1 nM, which is in accordance with the strong binding signal observed in the microsphere-based sandwich immunoassay experiments (See FIG. 15).

Domain and Epitope Mapping of β-catenin Binders

Structural analysis of β-catenin revealed a tripartite structure: a negatively charged N-terminus (aa 1-aa 140), the core domain (aa 141-aa 664) composed of 12 Armadillo repeats and a short C-terminus (aa 665-aa 781). The amino acid sequence of human β-catenin is available in GenBank under Accession Number NP_001091679.1, Version Number GI: 148233338. To test whether the selected BC2-Nb recognize these individual domains of β-catenin, a microsphere-based sandwich immunoassay was performed capturing either full-length β-catenin or the indicated domains with the selected Nbs. With this approach, it could be shown that BC2 exclusively recognizes the N-terminal domain (aa 1-119) of β-catenin (see FIG. 16).

To determine the minimal linear epitope of BC2-Nb a pepscan analysis was performed. For this purpose, 29 synthetic 15-mer peptides with a 11 amino acids overlap between consecutive peptides representing aa 1-127 of the β-catenin N-terminus were used. All peptides were immobilized via an additional cysteine at the N-terminus of the peptide on individual microsphere particles and incubated with biotinylated BC2-Nb in increasing concentrations (for reference see Bauer et al., (2012) Identification and quantification of a new family of peptide endocannabinoids (Pep-cans) showing negative allosteric modulation at CB1 receptors. *The Journal of biological chemistry* 287, 36944-36967)

For BC2-Nb, the analysis showed strong binding to two consecutive peptides comprising the residues 13-31 (FIG. 17 A). Further truncation revealed that BC2-Nb recognizes the amino acid sequence PDRKAAVSHWQQ (SEQ ID NO: 4) (aa 16-27) (FIG. 17 B). This observation is quite notable since only very few nanobodies are known to bind short linear peptide sequences (for reference see Muyldermans, S. (2013) Nanobodies: natural single-domain antibodies. *Annual review of biochemistry* 82, 775-797). For further analyses of the BC2-Nb epitope specificity, binding studies were performed using the identified peptide with a phosphorylated Ser23 residue. This modification completely abolishes binding of BC2 suggesting that this nanobody recognizes β-catenin only when Ser23 is not phosphorylated (FIG. 17 C). In summary, the data shows that BC2-Nb binds a linear peptide at the very N-terminus of β-catenin in a phosphorylation-dependent manner.

REFERENCES

1 De Genst, E. et al. Molecular basis for the preferential cleft recognition by dromedary heavy-chain antibodies. *Proceedings of the National Academy of Sciences of the United States of America* 103, 4586-4591, doi:10.1073/pnas.0505379103 (2006).

2 Muyldermans, S. Single domain camel antibodies: current status. *Journal of biotechnology* 74, 277-302 (2001).

3 Govaert, J. et al. Dual beneficial effect of interloop disulfide bond for single domain antibody fragments. *The Journal of biological chemistry* 287, 1970-1979, doi:10.1074/jbc.M111.242818 (2012).

4 Rothbauer, U. et al. A versatile nanotrap for biochemical and functional studies with fluorescent fusion proteins. *Molecular & cellular proteomics: MCP* 7, 282-289, doi:10.1074/mcp.M700342-MCP200 (2008).

5 Muyldermans, S. Nanobodies: natural single-domain antibodies. *Annu Rev Biochem* 82, 775-797, doi:10.1146/annurev-biochem-063011-092449 (2013).

6 Lee, S. Y. et al. Ube3a, the E3 ubiquitin ligase causing Angelman syndrome and linked to autism, regulates protein homeostasis through the proteasomal shuttle Rpn10. *Cellular and molecular life sciences: CMLS* 71, 2747-2758, doi:10.1007/s00018-013-1526-7 (2014).

7 Schembri, L. et al. The HA tag is cleaved and loses immunoreactivity during apoptosis. *Nature methods* 4, 107-108, doi:10.1038/nmeth0207-107 (2007).

8 Wegner, G. J., Lee, H. J. & Corn, R. M. Characterization and optimization of peptide arrays for the study of epitope-antibody interactions using surface plasmon resonance imaging. *Analytical chemistry* 74, 5161-5168 (2002).

9 Hilpert, K. et al. Anti-c-myc antibody 9E10: epitope key positions and variability characterized using peptide spot synthesis on cellulose. *Protein Eng* 14, 803-806 (2001).

10 De Genst, E. J. et al. Structure and properties of a complex of alpha-synuclein and a single-domain camelid antibody. *Journal of molecular biology* 402, 326-343, doi:10.1016/j.jmb.2010.07.001 (2010).

11 Traenkle, B. et al. Monitoring interactions and dynamics of endogenous beta-catenin with intracellular nanobodies in living cells. *Molecular & cellular proteomics: MCP*, doi:10.1074/mcp.M114.044016 (2015).

12 Huang, L. et al. SPECT imaging with 99mTc-labeled EGFR-specific nanobody for in vivo monitoring of EGFR expression. *Molecular imaging and biology: MIB: the official publication of the Academy of Molecular Imaging 10, 167-175, doi:10.1007/s11307-008-0133-8 (2008).

13 Vaneycken, I. et al. Preclinical screening of anti-HER2 nanobodies for molecular imaging of breast cancer. *FASEB journal: official publication of the Federation of American Societies for Experimental Biology* 25, 2433-2446, doi: 10.1096/fj.10-180331 (2011).

14 Broisat, A. et al. Nanobodies targeting mouse/human VCAM1 for the nuclear imaging of atherosclerotic lesions. *Circulation research* 110, 927-937, doi:10.1161/CIRCRESAHA.112.265140 (2012).

15 Ries, J., Kaplan, C., Platonova, E., Eghlidi, H. & Ewers, H. A simple, versatile method for GFP-based super-resolution microscopy via nanobodies. *Nature methods* 9, 582-584, doi:10.1038/nmeth.1991 (2012).

16 Yoon, M., Moir, R. D., Prahlad, V. & Goldman, R. D. Motile properties of vimentin intermediate filament networks in living cells. *The Journal of cell biology* 143, 147-157 (1998).

17 Leonhardt, H. et al. Dynamics of DNA replication factories in living cells. *The Journal of cell biology* 149, 271-280 (2000).

18 Maier, J., Traenkle, B. & Rothbauer, U. Real-time analysis of epithelial-mesenchymal transition using fluorescent single-domain antibodies. *Scientific reports* 5, 13402, doi:10.1038/srep13402 (2015).

19 Kirchhofer, A. et al. Modulation of protein properties in living cells using nanobodies. *Nature structural & molecular biology* 17, 133-138, doi:10.1038/nsmb.1727 (2010).

20 Kabsch, W. Xds. *Acta crystallographica. Section D, Biological crystallography* 66, 125-132, doi:10.1107/S0907444909047337 (2010).

21 McCoy, A. J. et al. Phaser crystallographic software. *Journal of applied crystallography* 40, 658-674, doi: 10.1107/S0021889807021206 (2007).

22 Winn, M. D. et al. Overview of the CCP4 suite and current developments. *Acta crystallographica. Section D, Biological crystallography* 67, 235-242, doi:10.1107/S0907444910045749 (2011).

23 Stein, N. CHAINSAW: a program for mutating pdb files used as templates in molecular replacement. *Journal of applied crystallography* 41, 641-643, doi:Doi 10.1107/S0021889808006985 (2008).

24 Adams, P. D. et al. PHENIX: a comprehensive Python-based system for macromolecular structure solution. *Acta crystallographica. Section D, Biological crystallography* 66, 213-221, doi:10.1107/S0907444909052925 (2010).

25 Murshudov, G. N., Vagin, A. A. & Dodson, E. J. Refinement of macromolecular structures by the maximum-likelihood method. *Acta crystallographica. Section D, Biological crystallography* 53, 240-255, doi:10.1107/S0907444996012255 (1997).

26 Emsley, P. & Cowtan, K. Coot: model-building tools for molecular graphics. *Acta crystallographica. Section D, Biological crystallography* 60, 2126-2132, doi:10.1107/S0907444904019158 (2004).

27 Chen, V. B. et al. MolProbity: all-atom structure validation for macromolecular crystallography. *Acta crystallographica. Section D, Biological crystallography* 66, 12-21, doi:10.1107/S0907444909042073 (2010).

What is claimed is:

1. An isolated epitope peptide consisting of 8 to 25 amino acids, wherein the epitope peptide comprises an amino acid sequence as defined in SEQ ID NO: 1 ($RX_4X_5AX_7SX_9W$),
   wherein $X_4$ can be K or a substitution;
   wherein $X_5$ can be A or R or a conservative substitution of A or R;
   wherein $X_7$ can be V or a conservative substitution of V, and
   wherein $X_9$ can be H or a conservative substitution of H.

2. The isolated epitope peptide of claim 1, wherein the epitope peptide comprises a sequence as defined by SEQ ID NO: 32 ($X_1X_2RX_4X_5AX_7SX_9WX_{11}X_{12}$),
   wherein $X_1$ can be P or A;
   wherein $X_2$ can be D or a conservative substitution of D;
   wherein $X_4$ can be K or a substitution;
   wherein $X_5$ can be A or R or a conservative substitution of A or R;
   wherein $X_7$ can be V or a conservative substitution of V, and
   wherein $X_9$ can be H or a conservative substitution of H; and
   wherein $X_{11}$ and $X_{12}$ can be Q or a conservative substitution of Q.

3. The isolated epitope peptide of claim 1, having an amino acid sequence as defined by SEQ ID NO: 3 (RKAAVSHW); or having an amino acid sequence as defined by SEQ ID NO:4 (PDRKAAVSHWQQ); or having an amino acid sequence as defined by SEQ ID NO: 5 (PVRSAALSQWSS), or having an amino acid sequence as defined by SEQ ID NO:33 (PDRVRAVSHWSS), or having an amino acid sequence as defined by SEQ ID NO: 34 (ADRVRAVSHWSS).

* * * * *